US008846763B2

(12) United States Patent
Barbanti et al.

(10) Patent No.: US 8,846,763 B2
(45) Date of Patent: *Sep. 30, 2014

(54) HIGH PURITY 2-[4-(3- OR 2-FLUOROBENZYLOXY)BENZYLAMINO] PROPANAMIDES AND METHODS OF USE THEREOF

(71) Applicant: Newron Pharmaceuticals S.p.A., Bresso (IT)

(72) Inventors: Elena Barbanti, Cologno Monzese (IT); Laura Faravelli, Garbagnate Milanese (IT); Patricia Salvati, Arese (IT); Renato Canevotti, Chignolo d'Isola (IT); Francesco Ponzini, Chignolo d'Isola (IT)

(73) Assignee: Newron Pharmaceuticals, S.p.A., Bresso (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/961,693

(22) Filed: Aug. 7, 2013

(65) Prior Publication Data

US 2014/0051758 A1 Feb. 20, 2014

Related U.S. Application Data

(63) Continuation of application No. 12/747,008, filed as application No. PCT/EP2008/066559 on Dec. 1, 2008, now Pat. No. 8,530,701.

(30) Foreign Application Priority Data

Dec. 11, 2007 (EP) .................................... 07023937

(51) Int. Cl.
| | | |
|---|---|---|
| *A61K 31/165* | (2006.01) | |
| *C07C 231/12* | (2006.01) | |
| *C07C 233/09* | (2006.01) | |
| *A61K 31/198* | (2006.01) | |
| *C07C 231/24* | (2006.01) | |
| *C07C 251/24* | (2006.01) | |
| *A61K 31/197* | (2006.01) | |
| *A61K 45/06* | (2006.01) | |

(52) U.S. Cl.
CPC ............. *C07C 251/24* (2013.01); *A61K 31/198* (2013.01); *C07C 231/12* (2013.01); *C07C 231/24* (2013.01); *A61K 31/197* (2013.01); *A61K 31/165* (2013.01); *A61K 45/06* (2013.01)
USPC ............................ 514/620; 564/165; 564/167

(58) Field of Classification Search
USPC ................... 564/165, 167; 514/620
See application file for complete search history.

(56) References Cited

U.S. PATENT DOCUMENTS

| | | | |
|---|---|---|---|
| 5,236,957 A | 8/1993 | Dostert et al. | |
| 8,076,515 B2 * | 12/2011 | Barbanti et al. | ............... 564/165 |
| 8,530,701 B2 * | 9/2013 | Barbanti et al. | ............... 564/165 |
| 2008/0096965 A1 | 4/2008 | Barbanti et al. | |

FOREIGN PATENT DOCUMENTS

| | | |
|---|---|---|
| EP | 1423168 | 6/2004 |
| EP | 1655029 A | 5/2006 |
| WO | WO-90/14334 | 11/1990 |
| WO | WO-99/35125 | 7/1999 |
| WO | WO-03/020273 | 3/2003 |
| WO | WO-2004/062655 | 7/2004 |
| WO | WO-2004/066987 | 8/2004 |
| WO | WO-2004/089353 | 10/2004 |
| WO | WO-2005/018627 | 3/2005 |
| WO | WO-2005/070405 | 8/2005 |
| WO | WO-2005/102300 | 11/2005 |
| WO | WO-2006/027052 | 3/2006 |
| WO | WO-2007/147491 | 12/2007 |

OTHER PUBLICATIONS

Cattabeni, F., 2004, "Ralfinamide," *IDrugs, Current Drugs Ltd.* 7(10):935-939.
Mealy et al., 2002, "Neurologic Drugs," *Drugs of the Future* 27(9):879-915.
PCT International Search Report from PCT/EP2008/066559 dated Feb. 12, 2009.
Pevarello et al., 1996, "Reductive Alkylation of α-Aminoamides," *Organic Preparations and Procedures Int.* 28(2):179-183.
Pevarello et al., 1998, "Synthesis and Anticonvulsant Activity of a New Class of 2-[(Arylalkyl)amino] alkanamide Derivatives," *J. Med. Chem.* 41:579-590.
Stummann et al., 2005 "The anti-nociceptive agent ralfinamide inhibits tetrodotoxin-resistant and terodotoxin-sensitive Na+ currents in dorsal root ganglion neurons," *European Journal of Pharmacology* 510:197-208.

* cited by examiner

Primary Examiner — Shailendra Kumar
(74) Attorney, Agent, or Firm — Dechert LLP

(57) ABSTRACT

A process for obtaining therapeutically active 2-[4-(3- and 2-(fluorobenzyloxy)benzylamino]propanamides, and their salts with pharmaceutically acceptable acids with high purity degree, in particular, with a content of dibenzyl derivatives impurities lower than 0.03%, preferably lower than 0.01% by weight. The process is carried out by submitting the Schiff bases intermediates 2-[4-(3- and 2-fluorobenzyloxy)benzylideneamino]propanamides to a reduction reaction with a reducing agent selected from sodium borohydride and potassium borohydride in an appropriate amount of an organic solvent selected from $C_1$-$C_5$ lower alkanols, allowing the formation and presence during a substantial position of the reduction reaction course of a suspension of the Schiff base into the saturated solution of the Schiff base into the same organic solvent.

40 Claims, 2 Drawing Sheets

HIGH PURITY 2-[4-(3- OR 2-FLUOROBENZYLOXY)BENZYLAMINO] PROPANAMIDES AND METHODS OF USE THEREOF

CROSS REFERENCE TO RELATED APPLICATIONS

This application is a continuation of U.S. application Ser. No. 12/747,008, filed on Sep. 1, 2010, now U.S. Pat. No. 8,530,701, which is the national stage under 35 U.S.C. §371 of Application Serial No. PCT/EP2008/066559, filed Dec. 1, 2008, which claims the benefit under 35 U.S.C. §§119(a) and 365(b) of European Patent Application No. 07023937.1, filed Dec. 11, 2007, the contents of all of which are incorporated herein by reference in their entireties.

BACKGROUND OF THE INVENTION

The present invention relates to a new process for the production of a 2-[4-(3- or 2-fluorobenzyloxy)benzylamino] propanamide compound selected from (S)-2-[4-(3-fluorobenzyloxy)benzylamino]propanamide, i.e. safinamide (Ia), (S)-2-[4-(2-fluorobenzyloxy)benzylamino]propanamide, i.e. ralfinamide (Ib),

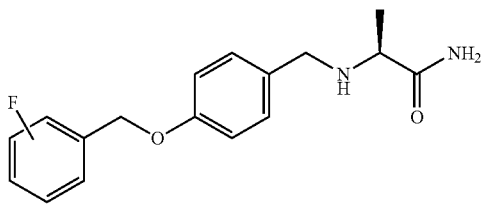

safinamide (Ia): 3-F
ralfinamide (Ib): 2-F the respective R-enantiomers (I'a) and (I'b), the respective racemic mixtures (Ia, I'a) and (Ib, I'b) and the salts thereof with pharmaceutically acceptable acids, (Ic), (Id), (I'c), (I'd) and their racemic mixtures (Ic, I'c) and (Id, I'd) in high yields and very high enantiomeric and chemical purity.

This method is also very useful for their production in large quantities. Safinamide (NW-1015, FCE-26743A, PNU-151774E) is a sodium channel blocker, a calcium channel modulator, a monoamino oxidase B (MAO-B) inhibitor, a glutamate release inhibitor and a dopamine metabolism modulator.

Safinamide is useful in the treatment of CNS disorders, in particular of epilepsy, Parkinson's disease, Alzheimer's disease, depression, restless legs syndrome and migraine (WO 90/14334, WO 2004/089353, WO 2005/102300 and WO 2004/062655).

Ralfinamide (NW-1029, FCE-26742A, PNU-0154339E) is a sodium channel blocker useful in the treatment of pain conditions, including chronic pain and neuropathic pain, migraine, bipolar disorders, depressions, cardiovascular, inflammatory, urogenital, metabolic and gastrointestinal disorders (WO 99/35125, WO 03/020273, WO 2004/062655, WO 2005/018627, WO 2005/070405, WO 2005/102300).

In particular, safinamide is specifically described in WO 90/14334. Safinamide, its R-enantiomer, their racemic mixture and their salts with pharmaceutically acceptable acids and the use thereof for the preparation of pharmaceutical compositions active as anti-epileptic, anti-Parkinson, neuroprotective, antidepressant, antispastic and/or hypnotic agents are specifically claimed in WO 90/14334.

Ralfinamide is specifically described in WO 90/14334. Ralfinamide, its R-enantiomer, their racemic mixture and their salts with pharmaceutically acceptable acids and their use thereof for the preparation of pharmaceutical compositions active as anti-epileptic, anti-Parkinson, neuroprotective, antidepressant, antispastic and/or hypnotic agent are comprised by the claims of WO 90/14334.

Moreover, the use as analgesics of safinamide, ralfinamide, the respective R-enantiomers, the respective racemic mixtures and their salts with pharmaceutically acceptable acids is claimed in WO 99/035125.

WO 2006/027052 A2 specifically discloses and claims the use of the single R-enantiomer of ralfinamide i.e., (R)-2-[4-(2-fluorobenzyloxy)benzylamino]propanamide (I'b), and its salts with pharmaceutically acceptable acids as a selective sodium and calcium channel modulator for the selective treatment of pathological affections wherein sodium or calcium channel mechanism(s) play(s) a pathological role, including pain, migraine, inflammatory processes affecting all body systems, disorders affecting skin and related tissue, disorders of the respiratory system, disorders of the immune and endocrinological systems, gastrointestinal, and urogenital disorders, wherein the therapeutic activity of said compound is substantially free from any MAO inhibitory side effect or exhibits significantly reduced MAO inhibitory side effect.

It has now been discovered that the large scale preparations of safinamide and ralfinamide according to the methods described in the prior art, contain two undesired impurities, i.e., respectively, (S)-2-[3-(3-fluorobenzyl)-4-(3-fluorobenzyloxy)-benzylamino]propanamide (IIa) and (S)-2-[3-(2-fluorobenzyl)-4-(2-fluorobenzyloxy)-benzylamino]propanamide (IIb), and their salt, in particular the respective methanesulfonates (IIc) and (IId)

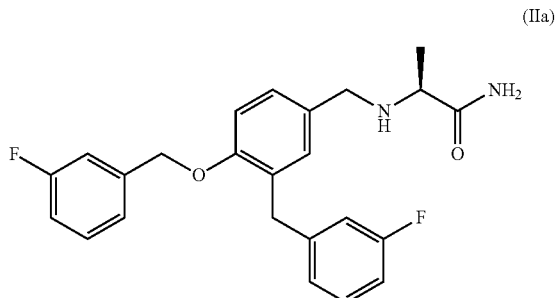

(IIa)

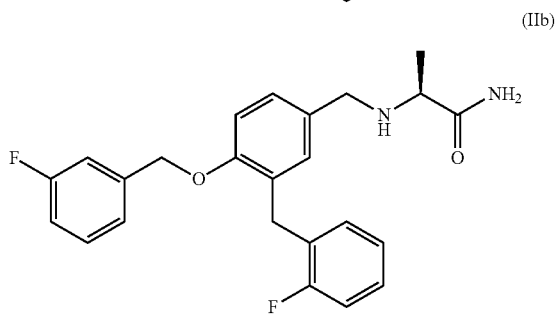

(IIb)

The same situation occurs with the preparation according the prior art methods for the R-enantiomers (I'a) and (I'b) of, respectively, safinamide and ralfinamide, the respective racemic mixtures (Ia, I'a) and (Ib, I'b), and the salts thereof with pharmaceutically acceptable acids, (I'c), (I'd) and the respective racemic mixtures (Ic, I'c) and (Id, I'd) in particular the methanesulfonates, which result to be contaminated by the respective R isomers (II'a), (II'b), (II'c), and (II'd) of the above identified impurities (IIa), (IIb), (IIc) and (Iid) or the respective racemic mixtures (IIa, II'a), (IIb, II'b), (IIc, II'c) and (IId, II'd).

This fact is of particular relevance because it has been found that the impurities mentioned above show a very high toxicity against enzymes of the cytochrome P450 system.

Many of the drug candidates fail in clinical trials because of unforeseen effects on human metabolism, or toxicity, due to unwanted impurities and, therefore, the elimination of such impurities in early pre-clinical phase is important and strongly desirable.

At preclinical level, the "drugability" of new compounds can be assessed using a very well established battery of in vitro assays, such as interaction with drug-metabolizing enzymes, cytotoxicity, metabolic stability and profiling, membrane permeability, intrinsic clearance and human ether-a-go-go related gene (HERG) channel blockade etc.

The Cytochrome P450 (CYP 450) system is the principal enzyme system for the metabolism of lipophilic xenobiotics, including drugs, carcinogens, and environmental pollutants. CYP 450 is a heme-containing, membrane bound, multienzyme system that is present in many tissues but is present at the highest level in liver. In human liver, it is estimated that there are 15 to 20 different xenobiotic-metabolizing CYP 450 forms. So far, more than fourteen CYP gene families have been identified in mammals. Despite the existing high homology, extensive studies have revealed that each CYP family and subfamily has distinct roles in xenobiotic metabolism. Three CYP families CYP1, CYP2 and CYP3 account for about 70% of human hepatic microsomes CYPs with CYP3 accounting for approximately 30%. These CYPs are the major responsible for the metabolism of most marketed drugs.

The CYP1 family contains several members that include CYP1A1, CYP1A2 and CYP1B1 and they are involved in the metabolism of acetaminophen, clomipramine and imipramine.

The CYP2 family contains several subfamilies including CYP2A, CYP2B, CYP2C, CYP2D and CYP2E. The CYP2C subfamily contains at least seven members. CYP2C9 is responsible for the metabolism of ibuprofen, diclofenac, tolbutamide and torsemide. CYP2C19 is the major isoenzyme metabolizing diazepam and omeoprazole. CYP2D6 has been shown to be responsible for metabolizing over 30% of the drugs on the market, including, antidepressants and cardiovascular and anti-psychotic drugs.

In the CYP3 family, three isoforms have been identified in human liver. Human CYP3A4 has been recognized to be the most important isoform in drug metabolism. To date, metabolism catalyzed by CYP3A4 is the major elimination route for nearly 50% of marketed drugs.

Because of their importance in drug metabolism, both CYP3A4 and CYP2D6 are often involved in drug-drug interactions and several clinically used compounds have been identified as potent inhibitor of these CYP 450 isoforms such as ketoconazole, terfenadine, erythromycin, miconazole propanolol and quinidine, respectively. This imposes a clear limitation on the use of these drugs.

A further problem consists in sudden death as a side effect of the action of non antiarrhytmic drugs is a major pharmacological safety concern facing the pharmaceutical industry and the health regulatory authorities. In recent years, at least five blockbusters drugs (astemizole, sertindole, terfenadine, cisapride, grepafloxacin) have been withdrawn from the market due to reports of sudden death. In all cases, long QT syndrome (LQTS), an abnormality of cardiac muscle repolarization, that is characterized by the prolongation of the QT interval in the electrocardiogram, was implicated as a predisposing factor for "torsades de pointes", a polymorphic ventricular tachycardia that can spontaneously degenerate to ventricular fibrillation and cause sudden death. Congenital LQTS can be traced back to several possible mutations resulting in defects in sodium channels, and two different potassium channels: the rapidly activating delayed rectifier ($T_{Kr}$) and the slowly activating delayed rectifier ($I_{Ks}$). Importantly, virtually every case of a prolonged duration of cardiac action potential related to drug exposure (acquired LQTS) can be traced to one specific mechanism: blockade of $I_{Kr}$ current in the heart. This current, a major contributor to phase 3 repolarization at the end of QT interval, is conducted by tetrameric pores, with the individual subunits encoded by HERG. With blockade of HERG $K^+$ channels widely regarded as the predominant cause of drug-induced QT prolongation, early detection of compounds with this undesirable side effect has become an important objective in the pharmaceutical industry.

Compounds with strong inhibition of drug-metabolizing enzymes, in particular CYP 450 enzymes, and HERG channel blocking properties have a high probability to be toxic and that their development has to be stopped at an early-stage.

As shown in the Table 1 the impurities (IIa), (IIb), (II'a), (II'b) and the respective racemates (IIa, II'a) and (IIb, II'b), as the methanesulfonate salt (IIc), (II'c), (IId), (II'd) and respective racemates (IIc, II'c) and (IId, II'd), strongly inhibit in the micro and submicromolar range CYP3A4, CYP2D6, CYP2C19, CYP2C9 and HERG currents and are highly cytotoxic, compared with safinamide methanesulfonate (Ic) and ralfinamide methanesulfonate (Id) with high purity degrees, containing less than 0.03% by weight of the above said impurities.

TABLE 1

| Compound | HERG $IC_{50}$, µM | Cytotoxicity $IC_{50}$, µM | CYP3A4 $IC_{50}$, µM | CYP2D6 $IC_{50}$, µM | CYP2C19 $IC_{50}$, µM | CYP2C9 $IC_{50}$, µM | CYP1A2 $IC_{50}$, µM |
|---|---|---|---|---|---|---|---|
| Impurity (IIc) | 1.20 | 6.70 | 0.05 | 0.77 | 0.42 | 7.29 | >40 |
| Impurity (II'c) | <1 | 8.81 | 0.09 | 0.15 | 0.15 | 4.94 | 29.24 |
| Impurity (IIc, II'c) | <1 | 11.84 | 0.06 | 0.31 | 0.17 | 5.57 | 28.03 |
| Safinamide methanesulfonate (Ic) | 27.0 | 248.0 | >40 | >40 | 23.85 | >40 | >40 |

TABLE 1-continued

| Compound | HERG IC$_{50}$, µM | Cytotoxicity IC$_{50}$, µM | CYP3A4 IC$_{50}$, µM | CYP2D6 IC$_{50}$, µM | CYP2C19 IC$_{50}$, µM | CYP2C9 IC$_{50}$, µM | CYP1A2 IC$_{50}$, µM |
|---|---|---|---|---|---|---|---|
| Impurity (IId) | 2.66 | 15.00 | 0.05 | 0.92 | 1.89 | 8.01 | >40 |
| Impurity (II'd) | <1 | 11.46 | 0.07 | 0.62 | 0.03 | 4.34 | >40 |
| Impurity (IId, II'd) | <1 | 14.34 | 0.06 | 1.19 | 0.03 | 4.96 | 39.44 |
| Ralfinamide methanesulfonate (Id) | 18.0 | >300 | >40 | >40 | >40 | >40 | >40 |

Table 2 shows comparative results (IC$_{50}$) about the inhibition of the cytocrome CYP3A4 using samples of highly pure safinamide and ralfinamide methanesulfonate containing less than 0.03% by weight of the above said impurities in comparison with the same samples of highly pure safinamide and ralfinamide doped with 0.3% by weight of the impurity (IIc) and (IId), respectively.

When 0.3% by weight of the impurities (IIc) and (IId) are added to highly pure safinamide and ralfinamide methanesulfonate, a significant decrease in IC$_{50}$ on CYP3A4 is observed in both cases meaning that the impurities contribute to a strong inhibition of the enzyme activity.

TABLE 2

| Compound | CYP3A4 IC$_{50}$, µM |
|---|---|
| Safinamide methanesulfonate | >40 |
| Safinamide methanesulfonate plus 0.3% (IIc) impurity | 18 |
| Ralfinamide methanesulfonate | >40 |
| Ralfinamide methanesulfonate plus 0.3% (IId) impurity | 7.76 |

As shown in Table 3 the impurity (IIc) increases, starting from 3 mg/kg ip, the mortality in the mice Maximal Electroshock (MES) test without any pharmacological activity, i.e. protection from convulsions.

TABLE 3

| | MES | | | | | |
|---|---|---|---|---|---|---|
| | 3 mg/kg ip | | 10 mg/kg ip | | 30 mg/kg ip | |
| Compound | % protection | dead/live | % protection | dead/live | % protection | dead/live |
| Safinamide methanesulfonate | 50 | 0/10 | 100 | 0/10 | 100 | 0/10 |
| Impurity IIc | 0 | 5/10 | 0 | 4/10 | 0 | 4/10 |

Table 4 reports that the impurity (IId), when given p.o. at 10 and 20 mg/kg, in the Maximal Electroshock test (MES) doesn't protect mice from convulsions if compared with the same doses of ralfinamide methanesulfonate.

TABLE 4

| | MES | | | |
|---|---|---|---|---|
| | 10 mg/kg p.o. | | 20 mg/kg p.o. | |
| Compound | Protection % | Dead/live | | Dead/live |
| Ralfinamide methanesulfonate | 60% | 0/10 | 90% | 0/10 |
| Impurity (IId) | 0% | 0/10 | 0% | 0/10 |

Based on all these data, the impurities (IIc), (II'c), (IId) and (II'd), and the respective racemic mixtures (IIc, II'c) and (IId, II'd) which are present in undesirable amount in safinamide, ralfinamide, their R-isomers and the respective racemic mixtures respectively, synthesized with the process described in WO 90/14334 and by Pevarello et al in J. Med. Chem, 1998, 41, 579-590, or in WO2006/027052, show in vitro some undesirable features, such as cellular toxicity, strong inhibition of some isoform of CYP 450, HERG channel blockade and no protective activity in an "in vivo" model of epilepsy.

One of the important aspects of CYP is the variation among different population groups. Variations in drug metabolism are of great importance in clinical studies. Considerable variation in the enzymatic activity of CYP3A4 and CYP2D6 has been demonstrated between different ethnic groups and even among different individuals in the same ethnic group. The difference in the CYP activity among individuals varies significantly, depending upon different isoenzymes. Changes in the CYP expression level of different individuals can cause variations in drug metabolism. More importantly, polymorphism can also result in CYP enzyme variants with lower or higher enzymatic activity that leads to variations in drug metabolism. CYP2D6 polymorphism is a well-studied topic in drug metabolism. In clinical studies, pronounced variations between individuals were first found in the metabolism of antihypertensive and antiepileptic drugs. Elimination of CYP2D6 metabolized drugs is slower in those individuals who carry defective CYP2D6 alleles. Individuals with slow metabolism are classified as poor metabolizers (PM), while catalytically competent individuals are called extensive metabolizers (EM): The incidence of the PM phenotype in population of different racial origin varies: approximately 5 to 10% of Caucasians are of the PM phenotype, but only 1% in Asian population. CYP2C19 is another important polymorphic isoform that has clinical implications.

Taken into account these observations, a compound that does not interfere with CYP450 isoforms (neither inhibition nor induction) has a very low risk for drug-drug interactions in clinical practice and can be simply and safely prescribed by physicians.

In particular, drugs that not interfere with the cytochromes of the CYP450 system are particularly indicated for the therapeutical treatment of individuals that are classified as poor metabolizers (PM) or for the therapeutical treatment of patients who are concomitantly assuming other drugs which are known to interfere with said cytochromes, such as ketoconazole, terfenadine, erythromycin, miconazole, propanolol and quinidine, and/or are known to have HERG channel blocking properties.

According to the common clinical practice, safinamide and ralfinamide methanesulfonates (Ic) and (Id) are usually administered to the patient in need thereof for a long period of time, subdivided in several daily dose. This is particularly the case of therapeutical applications wherein the disease to be treated is: Parkinson's disease, Alzheimer's disease and restless legs syndrome (for the use of safinamide) or chronic or neuropathic pain, cardiovascular or inflammatory disorders (for the use of ralfinamide). Although the daily dosage may vary according to the specific conditions and needs of the patients, the safinamide methanesulfonate daily dosage may usually range from 10 mg/day to 800 mg/day, while ralfinamide methanesulfonates daily dosage may usually range from 10 mg/day to 1 g/day. Under these conditions, and in consideration of the data reported above, it is highly advisable to keep the level of the impurities (IIa) and (IIb) or the salts thereof, in particular the methanesulfonate salts (IIc) and (IId) in the pharmaceutical dosage forms of safinamide and ralfinamide, or the salts thereof, as low as possible, in any case lower than 0.03%, preferably lower than 0.01% by weight with respect to the amount of, respectively, safinamide and ralfinamide, or the salts thereof, in particular the methanesulfonate salts.

The same considerations apply to the R-enantiomers of safinamide and ralfinamide (I'a) and (I'b), the respective racemic mixture (Ia, I'a) and (Ib, I'b) and the salts thereof with pharmaceutically acceptable acids with regards to the respective impurities (II'a), (II'b), the respective racemic mixtures (IIa, II'a) and (IIb, II'b) and the salts thereof with pharmaceutically acceptable acids.

Investigations and experimental studies carried out by the inventors have shown that safinamide, ralfinamide, the respective R-enantiomers, the respective racemic mixtures or the salts thereof with pharmaceutically acceptable acids, when prepared according to the prior art methods contain an amount of the respective impurities (IIa), (IIb), their R-enantniomers (II'a) and (II'b), the respective racemic mixtures (IIa, II'a) and (IIb, II'b), or the salts thereof with pharmaceutically acceptable acids, (such as (IIc), (IId), (II'c) and (II'd) or the respective racemic mixtures (IIc, II'c) and (IId, II'd)) that are higher than 0.03% by weight. Therefore, the above said products are unsuitable for wide and safe therapeutical applications. In particular, pharmaceutical preparations containing safinamide, ralfinamide, the respective R-enantiomer (I'a) or (I'b), the respective racemic mixture (Ia, I'a) and (Ib, I'b) or the salt thereof with pharmaceutically acceptable acids, wherein the content of the respective impurities (IIa), (IIb), (II'a), (II'b), their racemic mixture (IIa, II'a) and (IIb, II'b), or the salts thereof with pharmaceutically acceptable acids is not lower than 0.03%, preferably than 0.01%, by weight with respect to the above said therapeutically active substances, are not suitable for use as medicaments in particular groups of patients as described above.

In particular, pharmaceutical preparations containing safinamide, ralfinamide, the respective R-enantiomers (I'a) or (I'b) or the respective racemic mixtures (Ia, I'a) and (Ib, I'b), or the salt thereof with pharmaceutically acceptable acids, wherein the content of the respective impurities (IIa), (IIb), (II'a), (II'b), the respective racemic mixtures (IIa, II'a) and (IIb, II'b), or the salts thereof with pharmaceutically acceptable acids is not lower than 0.03%, preferably than 0.01%, by weight with respect to the above said active substances, are not suitable for use in the therapeutical treatment of a wide population of patients including those individuals that are classified as poor metabolizers (PM) or who are concomitantly assuming other drugs that are known to interfere with the cytochromes of the CYP 450 system.

In this specification and claims the values of the above indicated limits, unless as otherwise specified, are to be intended as expressing the percent ratio by weight of the "active substances", i.e., the effective content of the toxicologically active impurity (IIa), (IIb), (II'a), (II'b), or the respective racemic mixtures (IIa, II'a) and (IIb, II'b) measured with respect to the effective content of the therapeutically active substance (Ia), (Ib), (I'a), (I'b) or the respective racemic mixtures (IIa, II'a) and (IIb, II'b).

The expressions such as "high purity", "high purity degree", "high chemical purity", "highly pure" etc, when referred to safinamide, ralfinamide the respective R-enantiomers, the respective racemic mixtures, or the salts thereof with pharmaceutically acceptable acids, in this description and claims identify products containing not less than 98.5 percent (evaluated as area percent by HPLC methods) of safinamide (Ia), ralfinamide (Ib), the respective R-enantiomers (I'a) and (I'b), the respective racemic mixtures (Ia, I'a) and (Ib, I'b) or the salts thereof with pharmaceutically acceptable acids wherein the content of the respective impurity (IIa), (IIb), (II'a), (II'b), the respective racemic mixtures (IIa, II'a) and (IIb, II'b), or the salts thereof with pharmaceutically acceptable acids is lower than 0.03 percent, preferably lower than 0.01 percent, by weight (referred to the "active substances") determined by HPLC methods.

Other impurities, barely detectable, derive from the very small quantities of benzyl, 2- and 4-fluorobenzyl chloride and of 3- and 4-fluorobenzyl chloride which are contained in the commercially available 3-fluorobenzyl chloride and 2-fluorobenzyl chloride respectively, used for the synthesis of 4-(3-fluorobenzyloxy)benzaldehyde (IVa) and 4-(2-fluorobenzyloxy)benzaldehyde (IVb) intermediates for the preparation of, respectively, compounds (Ia), (Ib), (I'a), (I'b) (Ia, I'a) and (Ib, I'b) and their salts with pharmaceutically acceptable acids.

Analogously, the above mentioned terms, "high purity", "high purity degree", "high chemical purity", "highly pure", when referred to the 4-(3- or 2-fluorobenzyloxy)benzaldehyde intermediates (IVa) and (IVb), identify products containing not less than 98.5 percent (evaluated as area percent by GC methods) of each of the above named compounds and wherein the content of the respective di-benzylated impurity (VIa) or (VIb) is lower than 0.03 percent, preferably lower than 0.01 percent by weight (evaluated by GC methods).

The process described in this invention, by strongly reducing the impurities, provides products with high chemical purity and safer biological profile.

According to the process described in the present invention safinamide, ralfinamide, the respective R-enantiomers (I'a) and (I'b), the respective racemic mixtures (Ia, I'a) and (Ib, I'b) and the salts thereof with pharmaceutically acceptable acids, in particular with methanesulfonic acid, are obtained with high yields and high purity where the content of the respective impurities (S)-2-[3-(3-fluorobenzyl)-4-(3-fluorobenzyloxy) benzylamino]propanamide (IIa), (S)-2-[3-(2-fluorobenzyl)-4-(2-fluorobenzyloxy)benzylamino]propanamide (IIb), the respective R-enantiomers (II'a) and (II'b), the respective racemic mixtures (IIa, II'a) and (IIb, II'b) and the salt thereof with pharmaceutically acceptable acids, in particular with methanesulfonic acid (generically named "dibenzyl derivatives") is lower than 0.03%, preferably than 0.01% (by weight), referred to the "active substances".

A further object of this invention is to provide safinamide, ralfinamide, the respective R-enantiomers, the respective racemic mixtures or the salts thereof with a pharmaceutically acceptable acid, preferably methanesulfonic acid, with a high purity degree, in particular with a content of the respective dibenzyl derivatives of the formula (IIa), (IIb) (II'a), (II'b), their racemic mixtures (IIa, II'a) and (IIb, II'b), or the salts thereof with a pharmaceutically acceptable acid, e.g. the methanesulfonic acid, lower than 0.03%, preferably lower than 0.01% by weight (referred to the "active substances"), which is suitable for their safe use as medicaments.

Another object of this invention is to provide pharmaceutical formulations comprising safinamide, ralfinamide, the respective R-enantiomers (I'a) and (I'b), the respective racemic mixtures (Ia, I'a) and (Ib, I'b) or a salt thereof with a pharmaceutically acceptable acid, preferably methanesulfonic acid, as the active agents wherein the content of the respective dibenzyl derivatives (IIa), (IIb), their R-enantiomers (II'a) and (II'b), the respective racemic mixtures (IIa, II'a) and (IIb, II'b) or the salt thereof with a pharmaceutically acceptable acid, e.g. methanesulfonic acid, is lower than 0.03%, preferably lower than 0.01% by weight (referred to the "active substances").

More particularly, according to a preferred embodiment of this invention, the process herein disclosed allows the production of a medicament containing highly pure (i) safinamide, its R-enantiomer (I'a) their racemic mixture or a salt thereof with a pharmaceutically acceptable acid, preferably methanesulfonic acid, or (ii) ralfinamide, its R-enantiomer (I'b), their racemic mixture (IIa, II'a) and (IIb, II'b) or a salt thereof with a pharmaceutically acceptable acid, preferably methanesulfonic acid, for the treatment of, respectively, (i) epilepsy, Parkinson's disease, Alzheimer's disease, depression, restless legs syndrome pain and migraine, or (ii) pain conditions including chronic and neuropathic pain, migraine, bipolar disorders, depressions, cardiovascular, inflammatory, urogenital, metabolic and gastrointestinal disorders, under conditions that are not interfering with the cytochromes of the CYP450 system, in particular CYP3A4, CYP2D6, CYP2C19, CYP2C9 and do not exhibit HERG channel blocking properties.

Moreover, according to a further preferred embodiment of this invention, the process herein disclosed allows the preparation of a medicament containing highly pure ralfinamide single R-enantiomer, or a salt thereof with a pharmaceutically acceptable acid, preferably methanesulfonic acid, for the selective (i.e., where the therapeutical activity of the active substance which is administered to the patient is substantially free from any MAO inhibitory side effect or exhibits significantly reduced MAO inhibitory side effect) treatment of the pathological affections where sodium and/or calcium channel mechanism(s) play(s) a pathological role that are identified in WO 2006/027052 A2, such as, pain, migraine, inflammatory processes affecting all body systems, disorders affecting skin and related tissues, disorders of the respiratory system, disorders of the immune and endocrinological system, gastrointestinal, and urogenital disorders, under conditions that are not interfering with the cytochromes of the CYP450 system, in particular CYP3A4, CYP2D6, CYP2C19, CYP2C9 and do not exhibit HERG channel blocking properties.

Therefore, the process of this invention allows the manufacture of pharmaceutical formulations containing safinamide, its R-enantiomer (I'a), ralfinamide, its R-enantiomer (I'b), the respective racemic mixtures, (Ia, I'a) and (Ib, I'b) or a salt thereof with a pharmaceutically acceptable acid, preferably methanesulfonic acid, which are suitable for the treatment of the above mentioned disorders in patients that are classified as poor metabolizers (PM) or for the therapeutical treatment of patients who are concomitantly assuming other drugs which are known to interfere with the cytochromes of the CYP450 system and/or are known to have HERG channel blocking properties.

All these new pharmaceutical formulations were neither suggested nor achievable by applying the pharmaco-toxicological knowledge regarding safinamide and ralfinamide nor by using these active agents prepared according to the methods available in the state of the art. The above said pharmaceutical formulations may optionally comprise one or more additional active agents, besides safinamide, ralfinamide, the resptective R-enantiomers, the respective racemic mixtures or the salts thereof with a pharmaceutically acceptable acid, preferably methanesulfonic acid, having the above described high purity degree. For instance, a new pharmaceutical formulation useful for the adjunctive treatment of Parkinson's disease or restless legs syndrome may comprise one or more adjunctive Parkinson's disease active agent(s) such as those described in WO 2004/089353 and WO 2005/102300, preferably a dopamine agonist and/or levodopa and/or a catechol-O-methyltransferase (COMT) inhibitor, in addition to safinamide, its R-enantiomer, their racemic mixture, or a salt thereof with a pharmaceutically acceptable acid, preferably methanesulfonic acid, obtained according to the process of this invention and having the above said high purity degree.

As a further example, a new pharmaceutical formulation according to this invention useful for the treatment of pain conditions, including chronic pain and neuropathic pain, and migraine may optionally contain a further active agent such as gabapentin and pregabalin, or a pharmaceutically acceptable salt thereof as described in EP 1423168, in addition to ralfinamide, its R-enantiomer, their racemic mixture, or a salt thereof with a pharmaceutically acceptable acid, preferably methanesulfonic acid, obtained according to the process of this invention and having the above said high purity degree.

Similarly, a new pharmaceutical formulation according to this invention, useful as a medicaments selectively active as sodium and/or calcium channel modulator for the selective treatment of pathological affections where sodium and/or calcium channel mechanism(s) play(s) a pathological role according to WO 2006/027052 A2, such as, pain, migraine, inflammatory processes affecting all body systems, disorders affecting skin and related tissues, disorders of the respiratory system, disorders of the immune and endocrinological system, gastrointestinal, and urogenital disorders may optionally contain a further active agent. For instance, a pharmaceutical formulation for treating pain conditions may contain gabapentin or a gabapentin related agent in addition to the single R-enantiomer of ralfinamide (I'b) or a salt thereof with a pharmaceutically acceptable acid, preferably methanesulfonic acid, obtained according to the process of this invention and having the above said high purity degree.

The pharmaceutical compositions containing high purity degree safinamide, ralfinamide, the respective R-enantiomers, the respective racemic mixtures, or the salts thereof with pharmaceutically acceptable acids according this invention can be prepared by conventional procedures known in the art, for instance by mixing the active compounds with pharmaceutically, therapeutically inert organic and/or inorganic carrier materials. The compositions of the invention can be in liquid form, e.g. in the form of a solution, suspension, emulsion; or in solid form, e.g. tablets, troches, capsules, patches.

Suitable pharmaceutically, therapeutically inert organic and/or inorganic carrier materials useful in the preparation of the composition of the present invention include, for example, water, gelatine, arabic gum, lactose, starch, cellulose, magnesium stearate, talc, vegetable oils, polyalkyleneglycols, cyclodextrins and the like. The pharmaceutical compositions of the invention can be sterilized and may contain, besides the active ingredient(s), further components well known to the skilled in the art, such as, for example, preservatives, stabilizers, wetting or emulsifying agents, e.g. paraffin oil, mannide monooleate, salts to adjust osmotic pressure, buffers and the like.

A further object of this invention is to provide a method for treating CNS disorders, in particular epilepsy, Parkinson's disease, Alzheimer's disease and restless legs syndrome, which method comprises administering to a patient in need thereof an effective amount of high purity degree safinamide, its R-enantiomer, their racemic mixture, or a salt thereof with a pharmaceutically acceptable acid, preferably methanesulfonic acid, having a content of the respective dibenzyl derivatives (IIa), (IIa), their racemic mixture (IIa, II'a) or a salt thereof with a pharmaceutically acceptable acid, preferably methanesulfonic acid, lower than 0.03%, preferably lower than 0.01% by weight (referred to the "active substance"). Said method includes treating Parkinson's disease or restless legs syndrome by administering to a patient in need thereof an effective amount of the high purity degree safinamide its R-enantiomers (I'a), their racemic mixture (Ia, I'a) or a salt thereof, as described above, optionally in conjunction with one or more Parkinson's disease active agent(s) as described in WO 2004/089353, such as, for instance, a dopamine agonist and/or levodopa and/or a catechol-O-methyltransferase (COMT) inhibitor.

Moreover, a further object of this invention is to provide a method for treating pain conditions including chronic pain and neuropathic pain, migraine, bipolar disorders, depressions, cardiovascular, inflammatory, urogenital, metabolic and gastrointestinal disorders which method comprises administering to a patient in need thereof an effective amount of high purity degree of ralfinamide, its R-enantiomer, their racemic mixture, or a salt thereof with a pharmaceutically acceptable acid, preferably methanesulfonic acid, having a content of dibenzyl derivative (IIb), (II'b), their racemic mixture (IIb, II'b), or a salt thereof with a pharmaceutically acceptable acid, preferably methanesulfonic acid, lower than 0.03%, preferably lower than 0.01% by weight (referred to the "active substance"). The above said method includes treatment of pain conditions, comprising chronic pain and neuropathic pain, and migraine with high purity degree ralfinamide, its R-enantiomer, their racemic mixture or a salt thereof with a pharmaceutically acceptable acid, preferably methanesulfonic acid, optionally in conjuction with gabapentin or pregabalin.

Additionally, a further object of this invention is to provide a method for the selective treatment of a pathological affection wherein sodium or calcium channel mechanism(s) play(s) a pathological role, including pain, migraine, inflammatory processes affecting all body systems, disorders affecting skin and related tissues, disorders of the respiratory system, disorders of the immune and endocrinological systems, gastrointestinal, and urogenital disorders, wherein the therapeutical activity of said compound is substantially free from any MAO inhibitory side effect or exhibits significantly reduced MAO inhibitory side effect, which method comprises administering to a patient in need thereof a therapeutically effective amount of ralfinamide single R-enantiomer (R)-2-[4-(2-fluorobenzyloxy)benzylamino]propanamide, or a salt thereof with a pharmaceutically acceptable acid, preferably a salt with methanesulfonic acid, which has a content of impurity (R)-2-[3-(2-fluorobenzyl)-4-(2-fluorobenzyloxy)benzylamino]propanamide (II'b), or a salt thereof with a pharmaceutically acceptable acid, preferably with methenesulfonic acid, lower than 0.03%, preferably lower than 0.01% (by weight), optionally in conjunction with a further active agent, for instance in the case of the treatment of pain conditions, gabapentin or a gabapentin related substance.

The above mentioned methods of treatment are particularly useful in patients affected by the diseases listed above who are classified as poor metabolizers (PM) or who are concomitantly assuming other drugs which are known to interfere with the cytochromes of the CYP 450 system. In this description and claims the terms "treatment" or "treating" include prevention, alleviation and cure.

PRIOR ART

In WO 90/14334, in the paper by Pevarello et al. in J. Med. Chem., 1998, 41, 579-590 a two steps process for the preparation of benzyloxy-benzylamino-alkanamides is described:

a) synthesis of the intermediate 4-benzyloxybenzaldehydes by O-benzylation of the corresponding 4-hydroxybenzaldehydes with the suitable benzyl chlorides b) reductive alkylation of α-amino-amides with 4-benzyloxy-benzaldehydes using sodium cyanoborohydride or sodium borohydride as a reducing agent as schematically shown here below

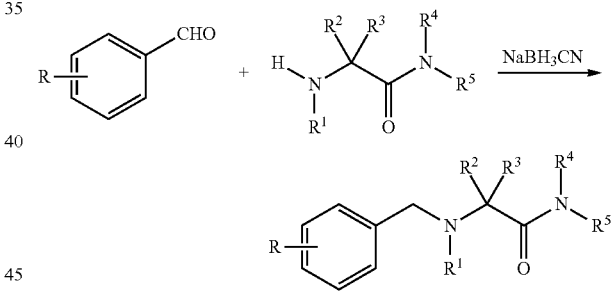

where R represents, among other substituents, 3-F and 2-F; $R^1$ represents, among other substituents, hydrogen; $R^2$ represents, among other substituents, hydrogen; $R^3$ represents, among other substituents, $CH_3$; both $R^4$ and $R^5$ represent, among other substituents, hydrogen.

In particular, as far as safinamide and rafinamide preparation is concerned, the reductive alkylation is the reductive alkylation of L-alaninamide with 4-(3-fluorobenzyloxy)benzaldehyde and 4-(2-fluorobenzyloxy)benzaldehyde respectively as shown here below

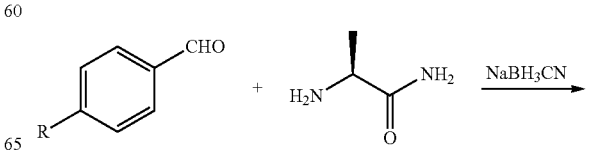

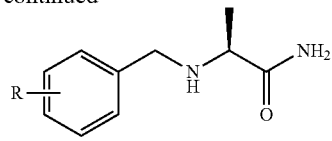

R = 3-F-benzyloxy = safinamide (Ia)
R = 2-F-benzyloxy = ralfinamide (Ib)

In J. Med. Chem. (Pevarello et al.), 1998, 41, 579-590 yields of 45% and 60% for the preparation of safinamide and ralfinamide methanesulfonate respectively, are reported, starting from the corresponding (fluorobenzyloxy)benzaldehydes.

The process described in WO 90/14334 and in the above cited paper is the same and provides a one-pot system where the iminoalkylation and the reduction are made in the same reactor. The suitable aldehyde is added all at once to a mixture of L-alaninamide hydrochloride, sodium cyanoborohydride, methanol and powdered molecular sieves.

According to Pevarello et al., in Org. Prep. Proc. Int. 1996, 28, 179-183 (where the synthesis of some α-benzylaminoamide derivatives by reductive alkylation is described), use of an α-aminoamide as hydrochloride is important for the formation of the iminium ion in place of the corresponding imine, as the iminium ion reacts more easily with sodium cyanoborohydride than with the aldehyde carbonyl group.

According to above authors, the one-pot procedure seems to avoid Schiff-base racemization problems and the molecular sieves speed up the reaction (although the yields are poor).

The cyanoborohydride is claimed to be the preferred agent utilized, and it seems that this choice is due to its selectivity (see Review "Sodium Cyanoborohydride—A Highly Selective Reducing Agent for Organic Functional Groups"—C. F. Lane, Synthesis 1975, 132-146), which makes it able to distinguish between the protonated Schiff base and the starting aldehyde.

The synthesis described in the paper by Pevarello et al. provides the isolation of the products by column chromatography, followed by conversion into the corresponding salts by treatment with acids. No information is provided about the enantiomeric and/or chemical purity of both safinamide and ralfinamide and/or their salts.

The method described in the prior art suffers from many drawbacks, that limit its use on large scale; here below some examples of said drawbacks are listed:
  formation of cyanides and cyanoderivatives;
  use of powdered molecular sieves which are physically changeable and expensive;
  yields generally lower than 70%;
  reaction products of low purity and difficult to purify
  use of large amounts of the solvent (about 5 L to 7 L of per mole) employed in the reductive alkylation reaction resulting in low final product concentration in the final reaction mixture (about 4-6% weight/volume);
  isolation of the reaction product by column chromatography, which is considered a troublesome and expensive isolation method when large scale preparations of active agents through chemical synthesis are involved.

The procedure for the manufacture of (R)-2-[4-(2-fluorobenzyloxy)benzylamino]propanamide (I'b) described in WO 2006/027052 A2 is based on the reduction with sodium borohydride of the product resulting from the reaction of (R)-alaninamide hydrochloride with 4-(2-fluorobenxyloxy)benzaldehyde (no data regarding the purity degree of this reactant is given) and triethylamine in dry methanol in the presence of molecular sieves for 4 hours. No data regarding the purity of the obtained end compound are given. Also in this case, the drawbacks of the procedure, when applied to large scale preparations, are the use of powered or pellets molecular sieves, the use of large amounts of solvent, and, in spite of the purification operations, the presence in the final product (I'b) of the undesired impurity (II'b) in an amount higher than 0.03% by weight which makes the active substance (I'b) obtained by said method unsuitable for a therapeutical use with no or low risk of side effects due to the interference with the cytochromes of the CYP 450 system. The low purity degree and the low yields (30%-32%, molar) of the end product of the process disclosed in WO 2006/027052 has been demonstrated through several reproductions in different scale of the process described therein, a representative example of which is described in Example 23.3 of this application.

One of the principal features that distinguishes the process disclosed in WO 2006/027052 from the process of this invention and that has been found to be responsible of the remarkably low yields of said prior art process is that the amount of the organic solvent (methanol) which is employed in said process with respect to the molar amount of the Schiff base is of the order of about 5 L per mole of the Schiff base. It has now been discovered that these conditions cause the increase of undesired impurities in the final product, deriving from the species involved into the equilibrium between the Schiff's base and its precursors such as the same starting aldehyde, its acetals and aminoacetals.

The illustrative examples which follow this description, confirm that the products obtained according to the methods described in the prior art contain an amount of the impurities (IIa), (IIb), (IIc), (IId), (II'a), (II'b), (II'c), (II'd) (IIa, II'a), (IIb, II'b), (IIc, II'c) or (IId, II'd) which is higher than 0.03% by weight with respect to the respective therapeutically active substances (Ia), (Ib), (Ic), (Id, (I'a), (I'b), (I'c), (I'd), (Ia, I'a), (Ib, I'b), (Ic, I'c) or (Id, I'd). In addition, it shown that it is difficult to eliminate said impurities present in the final product safinamide, ralfinamide, the respective R-enantiomers, the respective racemic mixtures, or their salts with pharmaceutically acceptable acids, by using commonly known purification methods based on crystallization from solvents or chromatography, which, in any case, imply a reduction of yields.

SUMMARY OF THE INVENTION

The object of this invention is a method for preparing a high purity degree 2-[4-(3- or 2-fluorobenzyloxy)benzylamino]propanamide compound selected from (S)-2-[4-(3-fluorobenzyloxy)benzylamino]propanamide (safinamide, Ia), (S)-2-[4-(2-fluorobenzyloxy)benzylamino]propanamide (ralfinamide, Ib)

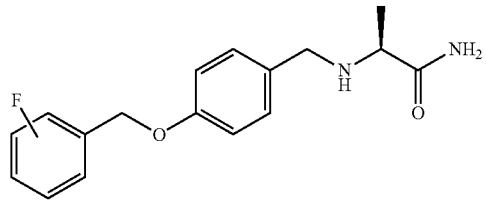

safinamide (Ia): 3-F
ralfinamide (Ib): 2-F the respective R-enantiomers (I'a) and (I'b), the respective racemic mixtures (Ia, I'a) and (Ib, I'b), and the salts thereof with pharmaceutically acceptable acids wherein safinamide, ralfinamide, the respective R-enantiomer (I'a) or (I'b), or the respective racemic mixture (Ia, I'a) and (Ib, I'b) or a salt thereof with a pharmaceutically acceptable acid has a content of the respective impurity, (S)-2-[3-(3-fluorobenzyl)-4-(3-fluorobenzyloxy)-benzylamino]propanamide (IIa), (S)-2-[3-(2-fluorobenzyl)-4-(2-fluorobenzyloxy)-benzylamino]propanamide (IIb),

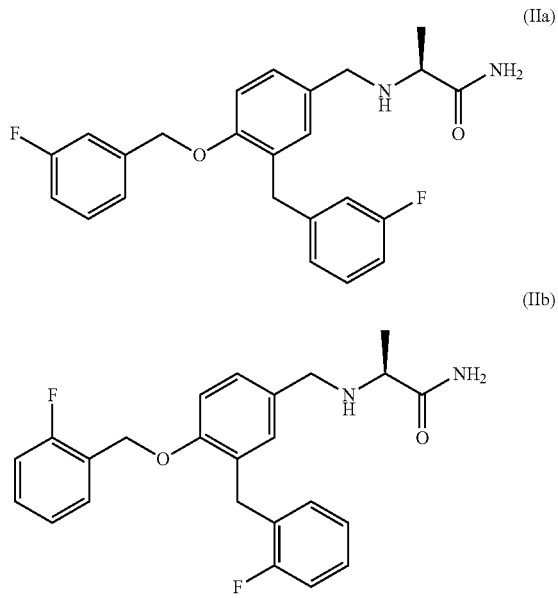

the respective R-enantiomer (II'a) or (II'b), or the respective racemic mixture (IIa, II'a) or (IIb, II'b) or a salt thereof with a pharmaceutically acceptable acid, which is lower than 0.03%, preferably lower than 0.01% (by weight), characterized in that a Schiff base intermediate of formula (IIIa), (IIIb)

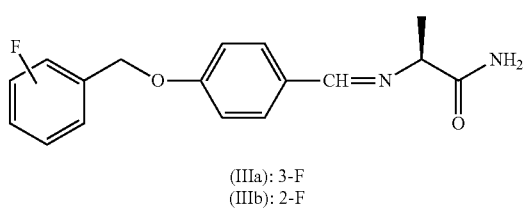

(IIIa): 3-F
(IIIb): 2-F the respective R-enantiomer (III'a) or (III'b) or the respective racemic mixture (IIIa, III'a) or (IIIb, III'b) which is obtained by an iminoalkylation reaction of 4-(3- or 2-fluorobenzyloxy) benzaldehyde with L-alaninamide or D-alaninamide or their racemic mixture, after completion of the iminoalkylation reaction is submitted to a to a reduction reaction with a reducing agent selected from sodium borohydride and potassium borohydride in a selected amount of an organic solvent chosen from ($C_1$-$C_5$) lower alkanols or a mixture thereof, optionally with a small amount water, wherein the ratio of the organic solvent to the Schiff base allows the formation and the presence during a substantial portion of the reduction reaction course of a suspension of the Schiff base into the saturated solution of the Schiff base in the same organic solvent and ranges from 0.5 L to 3.0 L, preferably from 0.7 L to 2.5 L, most preferably from 0.8 L to 2.0 L per each mole of Schiff base, whereby safinamide, ralfinamide, the respective R-enantiomer (I'a) or (I'b) or the respective racemic mixture (Ia, I'a) or (Ib, I'b) is obtained in a free base form and, optionally, converting said free base form in a salt thereof with a pharmaceutically acceptable acid.

According to a preferred embodiment of the invention, the method is further characterized in that the 4-(3- or 2-fluorobenzyloxy)benzaldehyde starting material employed for the generation of the Schiff base intermediate (IIIa), (IIIb), (III'a), (III'b) or the respective racemic mixture (IIIa, III'a) or (IIIb, III'b) has a content of 3-(3- or 2-fluorobenzyl)-4-(3- or 2-fluorobenzyloxy)benzaldehyde impurity lower than 0.03%, preferably lower than 0.01% by weight.

The formulas (IIIa) and (IIIb) as represented in this description and claims identify the Schiff base intermediate in both the E and Z configuration. According to a preferred embodiment of this invention, the process object of the present invention involves the three following steps:

a) preparation of the highly pure starting material 4-(3- or 2-fluorobenzyloxy)benzaldehyde starting material through O-benzylation of 4-hydroxybenzaldehyde with derivatives of the following general formula 3- or 2-F—$C_6H_4$—$CH_2$—Y (Va) or (Vb), where Y is a leaving group (Cl, Br, I, $OSO_2CH_3$ etc.); this O-benzylation is carried out under conditions which are highly selective for O-alkylation and gives 4-(3-fluorobenzyloxy)benzaldehyde or 4-(2-fluorobenzyloxy)benzaldehyde of high purity;

b) Complete formation of the Schiff base intermediate by condensation of 4-(3- or 2-fluorobenzyloxy)benzaldehyde starting material with L-alaninamide, D-alaninamide or its racemic mixture in the form of base or salt without any use of molecular sieves;

c) Treatment of the Schiff base with a reducing system selected from sodium borohydride and potassium borohydride in the presence of an organic solvent selected from ($C_1$-$C_5$)alkanols in an appropriate ratio to the Schiff base allowing the simultaneous presence of the Schiff base in solid form and of a saturated solution of the Schiff base into said solvent (i.e. a suspension of the Schiff base into a saturated solution of the Schiff base into said organic solvent) during a substantial portion of the reduction reaction course for obtaining, after work up and crystallization, respectively, safinamide, ralfinamide, the respective R-enantiomers or the respective racemic mixture in very high yield and with the above defined chemical purity; and, optionally, preparation of the salts thereof with pharmaceutically acceptable acids by common salification procedures. Pharmaceutically acceptable acids are, for instance, selected from nitric, hydrochloric, hydrobromic, sulphuric, perchloric, phosphoric, methanesulfonic, p-toluensulfonic, acetic, trifluoroacetic, proprionic, glycolic, lactic, oxalic, malonic, malic, maleic, tartaric, citric, benzoic, cinnamic, mandelic and salicylic acid.

SYNTHESIS OF THE 4-(3- OR 2-FLUOROBENZYLOXY)BENZALDEHYDE STARTING MATERIALS

Figure 1:
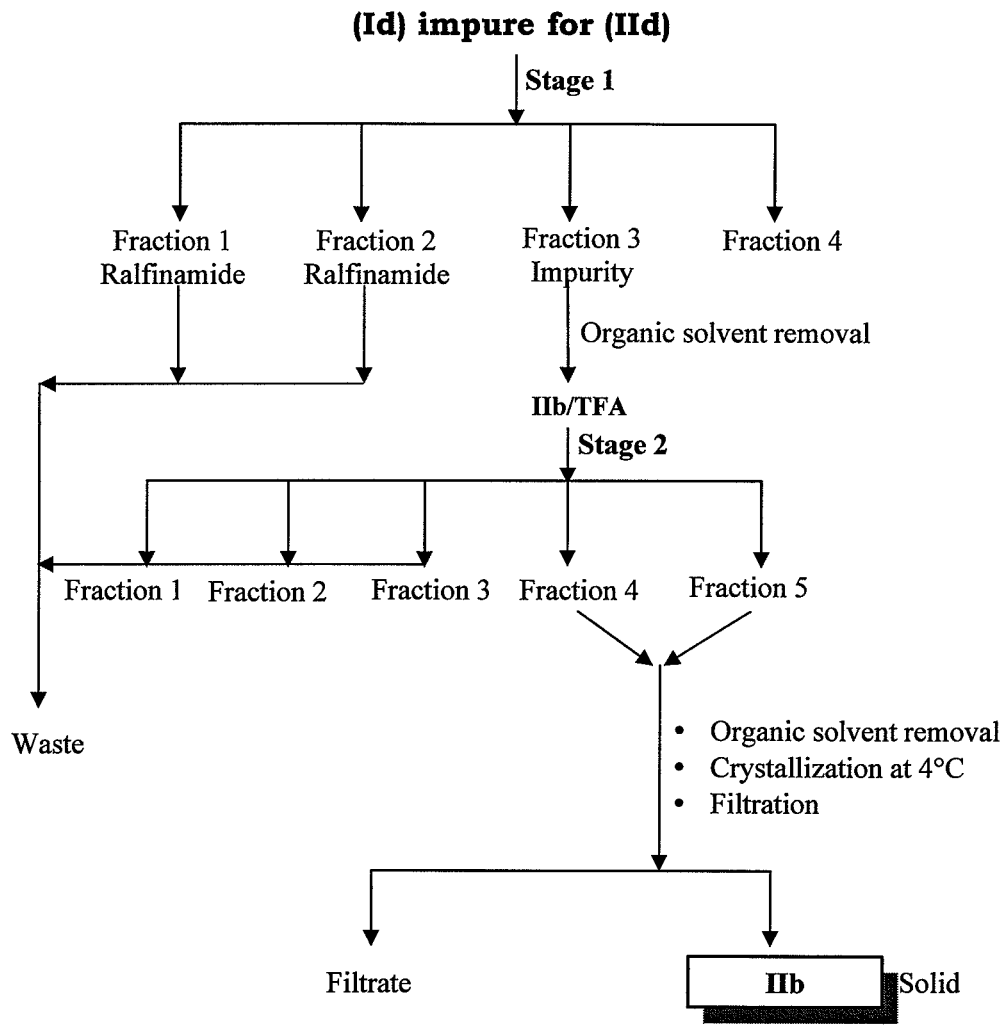
FIG. 1 depicts a two stage isolation procedure of (IIb) as described in Example 8d.

According to the known methods, the (fluorobenzyloxy) benzaldehydes starting materials necessary for the preparation of the Schiff base intermediates (IIIa), (III'a), (III'b), and the respective racemic mixtures (IIIa, III'a) and (IIIb, III'b), which are employed for the synthesis of, respectively, safinamide, ralfinamide, the respective R-enantiomers and the respective racemic mixtures according to this invention, are obtained by benzylation of 4-hydroxybenzaldehyde in a basic medium. The benzylation of phenol salts, which are being ambident nucleophiles, gives two different products, i.e. the desired O-alkylated derivatives and the undesired C-alkylated derivatives.

It has been effectively found that the fluorobenzylation of 4-hydroxybenzaldehyde with 3-fluorobenzyl chloride, performed according to the prior art, gives the 4-(3-fluorobenzyloxy)benzaldehyde (IVa) as the main product together with 3-(3-fluorobenzyl)-4-(3-fluorobenzyloxy)benzaldehyde (VIa) that derives from the alkylation of both the hydroxy group in position 4 and the carbon atom in position 3 of the 4-hydroxybenzaldehyde. The same happens in the fluorobenzylation of 4-hydroxybenzaldehyde with 2-fluorobenzyl chloride according to the following scheme:

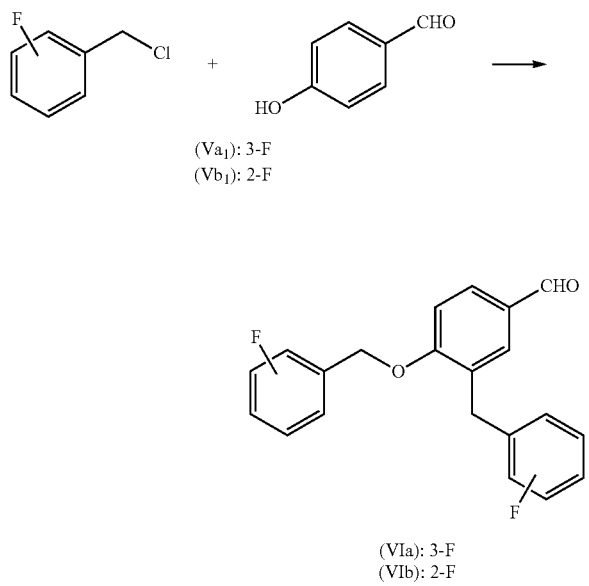

(Va₁): 3-F
(Vb₁): 2-F (VIa): 3-F
(VIb): 2-F

The reduction of a Schiff base formed by iminoalkylation of 4-(3- or 2-fluorobenzyloxy)benzaldehyde with L- or D-alaninamide or the racemic mixture thereof with an aldehyde starting material which contains the di-alkylated impurity gives an end product of formula (Ia), (Ib), (I'a), (I'b) or the respective racemic mixture (Ia, I'a) or (Ib, I'b) which is also impure of the respective di-alkylated compound, the di-benzyl derivative, (IIa), (IIb), (II'a), (II'b) or the respective racemic mixture (IIa, II'a) or (IIb, II'b), whether as a free base or a salified compound, preferably with methanesulfonic acid, (IIc), (IId), (II'c), (II'd) or the respective racemic mixture (IIc, II'c) or (IId, II'd), as shown in the following scheme which show the production the dibenzylate impurities (IIc) e (IId) related to, respectively, safinamide and ralfinamide.

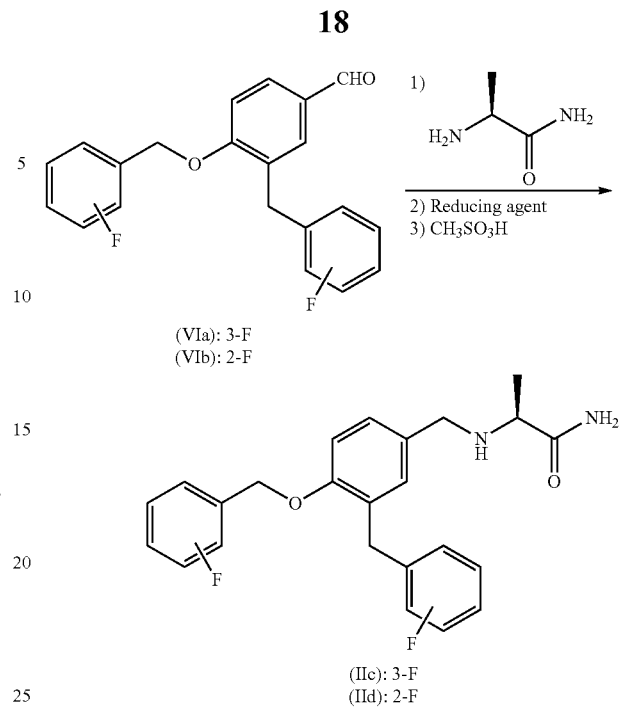

(VIa): 3-F
(VIb): 2-F (IIc): 3-F
(IId): 2-F

In an analogue way are produced the respective R-enantiomer (II'c), (II'd) and the respective racemic mixtures. Other pharmaceutically acceptable acids, e.g. nitric, hydrochloric, hydrobromic, sulphuric, perchloric, phosphoric, methanesulfonic, p-toluensulfonic, acetic, trifluoroacetic, proprionic, glycolic, lactic, oxalic, malonic, malic, maleic, tartaric, citric, benzoic, cinnamic, mandelic and salicylic acid can be used in the place of the preferred methanesulfonic acid.

The mono-alkylated derivative (safinamide, ralfinamide, the respective R-enantiomers and the respective racemic mixtures) and the corresponding di-alkylated impurities have similar chemical-physical properties and this makes difficult the purification of safinamide and ralfinamide with traditional methods.

Furthermore the known benzylation methods, and among them fluorobenzylation, suffer from these additional drawbacks:
1) the use of a lower alcohol as a solvent; in basic conditions, the solvent, for example methanol, can act itself as a nucleophilic reagent and gives, with 3- or 2-fluorobenzyl chloride a certain amount of methyl-fluorobenzyl-ether;
2) the extraction of the final product with a water-immiscible organic solvent is possible only after the alcoholic reaction solvent has been eliminated from the reaction mixture.

It has now been found that by using the above said prior art methods, in order to obtain a final product of formula (Ia), (Ib), (I'a), (I'b) or the respective racemic mixture (Ia, I'b) or (Ib, I'b) wherein the content of the impurity (IIa), (IIb), (II'a), (II'b) or the respective racemic mixture (IIa, II'a) or (IIb, II'b) is lower than 0.03% (by weight), it is necessary to drastically purify the intermediate 4-(3-fluorobenzyloxy)benzaldehyde (IVa) or 4-(2-fluorobenzyloxy)benzaldehyde (IVb) to reduce the content of the respective impurities of formula (VIa) and (VIb).

Said purification is preferably carried out by submitting the reaction products to crystallization, more preferably by adding to a solution of the crude compound (IVa) or (IVb) in an inert organic solvent a miscible inert organic non-solvent. The organic inert solvent is preferably selected from the aromatic hydrocarbons and, more preferably, is toluene. The miscible inert organic non-solvent is preferably selected from the lower aliphatic hydrocarbons, more preferably is n-hexane. A further crystallization procedure may consist in dissolving the above said compounds (IVa) or (IVb) in a hot solvent, e.g. cyclohexane or a di($C_3$-$C_4$)alkyl ether, such as diisopropyl ether at reflux, and then cooling the solution to room temperature, preferably at 10-15° C., most preferably, with inducing crystallization by addition of pure crystals of the pure compound (IVa) or (IVb).

According to one aspect of this invention, the 4-(3- or 2-fluorobenzyloxy)benzaldehyde starting material necessary for the preparation of the Schiff's base intermediates is obtained through a reaction between an alkylating agent of formula (Va) or (Vb) (see the scheme below where the F atom is in position 2 or 3 and Y is a leaving group such as, for example, Cl, Br, I, $OSO_2CH_3$, $OSO_2C_6H_4$-$pCH_3$, etc.) and 4-hydroxybenzaldehyde, which is carried out under phase-transfer conditions. Under said conditions the corresponding 4-(3- or 2-fluorobenzyloxy)benzaldehydes are obtained in high yields and with very low level of C,O-bis-alkylated impurities, preferably, after crystallization.

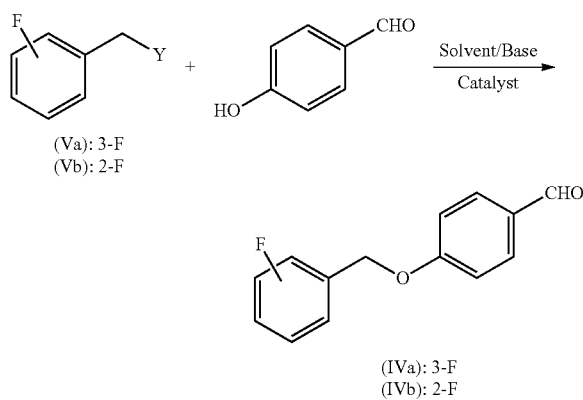

(Va): 3-F
(Vb): 2-F (IVa): 3-F
(IVb): 2-F

This new fluorobenzylation of 4-hydroxybenzaldehyde under phase-transfer conditions can be made both in a solid/liquid system, where in the liquid organic phase the reagents and the phase-transfer catalyst are dissolved and the solid phase is constituted by the inorganic base or the 4-hydroxybenzaldehyde salt (possibly generated in situ from 4-hydroxy-benzaldehyde and the inorganic base itself), and in a liquid/liquid organic/aqueous system where the inorganic base is dissolved in the aqueous phase.

A preferred system is the solid/liquid system wherein the inorganic base is preferably selected from $Na_2CO_3$, $K_2CO_3$, KOH and NaOH.

The organic solvents used in the reaction, both in the case of the liquid/liquid system and of the solid/liquid system, can be dialkyl ethers such as, for example, di-tert-butyl ether, ethyl-tert-butyl ether, or aromatic hydrocarbons such as, for example, toluene, ethylbenzene, isopropylbenzene and xylenes. All these solvents can be easily recovered by distillation.

The phase-transfer catalysts employed can be quaternary ammonium or phosphonium salts such as, for example, tetrabutyl ammonium bromide, tetradecyltrimethyl ammonium bromide, hexadecyltributyl phosphonium bromide, tricaprilylmethyl ammonium chloride (Aliquat), methyltrialkyl ($C_8$-$C_{10}$)ammonium chloride (Adogen), the tetradecyltrimethyl ammonium bromide being the preferred one.

Also polyethyleneglycols of low molecular weight can be used as phase-transfer catalysts such as, for example, PEG-200 (CAS 25322-68-3) or PEG-400 (CAS 25322-68-3).

The quantity of phase-transfer catalyst used is between 0.02-1 mol per mole of 4-hydroxybenzaldehyde, preferably between 0.1-1 mol per mole of 4-hydroxybenzaldehyde as, in these conditions, the quantity of the C,O-bis-fluorobenzylated impurities may result to be less than 0.03%, preferably equal to 0.01% or less by weight.

The ratio between the alkylating agents of formula (V) and 4-hydroxybenzaldehyde is comprised between 0.6 and 1.5, the preferred one being between 0.9 and 1.1.

The reaction temperature is comprised between 60° C. and 160° C., the preferred interval being between 80° C. and 120° C.

The reaction time is generally comprised between 4 and 8 hours.

The reaction yields are very high, as a rule, more than 90%.

The reaction productivity, i.e. the concentration of the reaction products in the reaction mixture is very high in the reaction condition described, normally is more or equal to 25% (weight/volume).

Synthesis of Safinamide and Ralfinamide their R-Enantiomers and of the Respective Racemic Mixtures by Reduction of the Schiff Bases Formed by Reaction of 4-(3- or 2-Benzyloxy)Benzaldehyde with L-Alaninamide or D-Alaninamide or their Racemic Mixture and the Salts Thereof The process, object of the present invention, comprises two steps a) complete formation of the Schiff base intermediate b) reduction of the Schiff base with a reducing agent selected from sodium borohydride and potassium borohydride The two steps can be performed in succession in the same reactor (one pot reaction) either with, or without, isolation of the Schiff base, in both cases with high yields.

The formation of the Schiff base intermediates involves the condensation of the 4-(3- or 2-fluorobenzyloxy)benzaldehyde with L-alaninamide, D-alaninamide, or their racemic mixture or a salt thereof with an acid ("alaninamide compound"), preferably an inorganic acid such as hydrochloric, hydrobromic, sulphuric, methanesulfonic acid etc. A racemic mixture of 4-(3- or 2-benzyloxy)benzylaminopropanamide is obtained when racemic alaninamide is employed instead of its L- or D-enantiomer.

In the case of isolation of the Schiff base, the experimental conditions applied for its formation allow to obtain the isolated Schiff base in the form of a precipitate in high yields and very pure form.

The Schiff base preparation is suitably performed in an organic protic solvent that must be inert vs. the reagents and the products and also inert vs. the reduction conditions of the iminic double bond. If it is desired to carry out the successive reduction step in the same reaction medium, suitable solvents are, for example, ($C_1$-$C_5$) lower alkanols, preferably methanol, ethanol and isopropanol.

The formation of the Schiff base intermediate must be complete and this is a relevant factor for obtaining high yields in the subsequent reduction step. According to a method of carrying out the process of this invention the Schiff base intermediate (IIIa), or (IIIb)

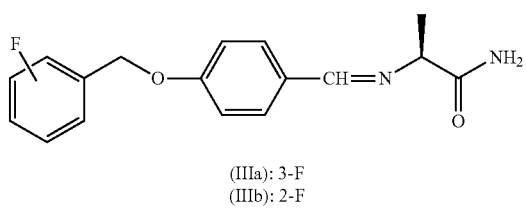

(IIIa): 3-F
(IIIb): 2-F the respective R-enantiomer (III'a) or (III'b), or the respective racemic mixture, resulting from the condensation reaction between the 4-(3- or 2-fluorobenzyloxy)benzaldehyde and L-alaninamide, D-alaninamide or its racemic mixture is isolated before performing the reduction of the iminic double bond.

Alternatively, one can favour the iminoalkylation reaction completion by operating under such conditions as to cause the precipitation of the intermediate imino compounds (IIIa), (IIIb), the respective R-enantiomer (III'a) or (III'b), or the respective racemic mixture (IIIc, III'a) or (IIIb, III'b), into the reaction solvent and then to submit the suspension containing said intermediate imino derivative to the reduction step.

The ratio between L-alaninamide, D-alaninamide or their racemic mixture (base or salt) and 4-(3- or 2-fluorobenzyloxy)benzaldehyde can be 1:1 but also a 10% excess of alaninamide compound can be advantageously used. The alaninamide compound may be introduced either as a free base or as an acid addition salt thereof. Preferably, it is introduced in the reaction mixture as a salt, most preferably as the hydrochloride salt, together with the stoichiometric amount of a base, preferably a tertiary amine such as, for example, triethylamine or diisopropylethylamine.

The reaction temperature in the preparation of the Schiff base is comprised between 0° C. and 60° C., preferably between 20° C. and 30° C.

The reaction time is usually comprised between 1 hour and 15 hours, preferably between 2 and 6 hours.

Under certain conditions, when D- or L-alaninamide is used as a free base and the iminoalkylation reaction time exceeds 8 hours, the resulting Schiff base may undergo racemisation at the chiral center. This is particularly true when the Schiff base does not crystallize during the iminoalkylation reaction.

The reduction of the Schiff base with the reducing agent selected from sodium borohydride and potassium borohydride is started only when the Schiff base formation is completed: if it is started before, secondary reactions become important, sometimes prevalent, with loss in yields and purity. One of these secondary reactions, the more important, causes the formation of benzylic alcohols by reduction of the carbonyl group of the (fluorobenzyloxy)benzaldehyde of choice.

The completion of the Schiff base formation can be maintained under control by analytical methods known in the art, e.g. by GC quantitative analysis of mother liquors.

The reduction of the Schiff base is the most important step of the process of this invention and its performance requires some specific conditions. The sodium or potassium borohydride reducing agent is employed in a molecular amount which ranges from 0.5 to 1.4 with respect to the Schiff base.

Use of sodium borohydride is preferred in view of its commercial availability and cost. The reaction is usually carried out in a solvent which can be the same solvent wherein the Schiff base is present in form of a suspension after the condensation reaction with alaninamide has been completed.

A ($C_1$-$C_5$) lower alkanol, such as methanol, ethanol, 1-propanol and 2-propanol, preferably methanol is usually employed as a reaction solvent in such case. Alternatively, when the Schiff base is isolated from the reaction medium (e.g. by filtration or centrifugation) the isolated Schiff base product is added to the selected amount of an organic solvent, preferably a protic organic solvent such as a lower ($C_1$-$C_5$) alkanol, preferably methanol, or a mixture of said protic organic solvent, optionally in the presence of a small amount of water (preferably, less than 1.5 percent by weight with respect to the amount of the organic solvent).

If the condensation reaction of the 4-(3- or 2-fluorobenzyloxy)benzaldehyde with the alaninamide compound is carried out by introducing this latter into the reaction mixture as a salt with an acid, then the addition of an appropriate amount of a base such as sodium or potassium hydroxide, tertiary ($C_1$-$C_4$)alkylamines, pyrrolidine, 4-methylmorpholine and the like to adjust the pH value to between 7 to 9. If, at the end of the iminoalkylation reaction the value of the pH of the reaction mixture has decreased below this interval, a further addition of an appropriate amount of the above mentioned base is made to the reaction mixture containing the Schiff base, in order to readjust the pH to the above value before any addition of the sodium or potassium borohydride reducing agent is made. The sodium or potassium borohydride reducing agent is usually added to the mixture of the Schiff base and the reaction solvent in several subdivided portions (usually in 15 to 20 portions) in a solid form, such as a powder or fine crystals under controlled conditions during the reaction course. Alternatively, the sodium or potassium borohydride is added portion wise or by dropping to the reaction mixture in the form of a methanolic solution stabilized by addition of sodium hydroxide (usually about 15 percent by weight of sodium hydroxide with respect to the sodium borohydride) or potassium hydroxide.

According to a preferred method of carrying out the Schiff base reduction, the stabilized methanolic solution of sodium or potassium borohydride is added in 15 to 25 potions or by dropping during 1 to 2 hours to the reaction mixture containing the Schiff base and the selected amount of reaction solvent, preferably methanol.

In order to carry out the reduction step under conditions wherein the ratio of the selected solvent to the Schiff base allows simultaneous presence of a saturated solution of the Schiff base into said solvent and of the Schiff base in solid form wherein the amount of the Schiff base out of the solvent phase is maximized, the amount of the solvent employed must be appropriately chosen.

Accordingly, the total amount of organic solvent used in the reduction step may range from 0.5 L to 3.0 L, preferably from 0.7 L to 2.5 L, most preferably from 0.8 L to 2.0 L per each mole of Schiff base. Under these conditions a significant portion of the Schiff base present in the reaction medium undergoing the reduction step is in the form of a solid during a substantial part of the reaction course. Under these conditions the productivity of the end product is very high and this has a positive economic impact in industrial scale production.

The pH of the reaction mixture which is submitted to the reduction step is adjusted at a value between 7 and 9, preferably between 8 and 8.5 (determined directly on the reaction mixture by means of a pHmeter) by addition of an appropriate amount of a base such as sodium or potassium hydroxide, tertiary (C1-C4)alkylamines, pyrrolidine, 4-methylmorpholine and the like, if needed, when the condensation between the aldehyde and the alaminamide derivate has been carried out with a salt thereof.

The reaction temperature during the reduction step is maintained between −10° C. and 30° C., preferably between 5° C. and 15° C.

The reduction time can vary from 0.5 to 5 hours, according to the solvent employed, the temperature, the concentration, etc., all factors well known to those skilled in the art.

The best results are obtained with reaction times of about three hours by using sodium borohydride as the reducing agent, methanol as the solvent in a proportion between 0.8 L and 2.0 L per each molar amount of the Schiff base at a temperature between 5° C. and 10° C.

At the end of the reaction, the reaction solvent is distilled under reduced pressure, the residue is dissolved in a water-immiscible organic solvent and the inorganic salts are removed by washing with water.

The final raw product, i.e. safinamide, ralfinamide, the respective R-enantiomer or the respective racemic mixture, is recovered by removing by distillation the organic solvent wherein the reaction product is dissolved. The raw safinamide, ralfinamide, the respective R-enantiomers or the respective racemic mixture is then purified by crystallization. The crystallization may be carried out by adding to a solution of the respective crude compound of formula (Ia), (Ib), (I'a), (I'b), (Ia, I'a) or (Ib, I'b) in an inert organic solvent a miscible inert organic non-solvent. The organic inert solvent is preferably selected from aromatic hydrocarbons such as benzene, toluene, dimethylbenzene and ethylbenzene and lower alkyl acetates and, more preferably, is ethyl acetate. The miscible inert organic non-solvent is preferably selected from the lower aliphatic hydrocarbons, such as hexane and heptane, and cyclohexane, more preferably is n-hexane.

Alternatively, the crystallization is carried out by dissolving the final raw product in a hot organic solvent, preferably toluene or cyclohexane, and then cooling the solution at room temperature, and recovering the pure product by filtration.

The bases, are then transformed into the desired salts according to known methods, in particular they are transformed into methanesulfonate salt, which has the physical/chemical properties (stability, granulometry, flowability etc.) suitable for the subsequent formulation into a pharmaceutical preparation for use as medicament.

EXAMPLE 1

Preparation of purified
4-(2-fluorobenzyloxy)benzaldehyde (Mb) by phase
transfer catalysis A mixture of 2-fluorobenzyl chloride (6.0 kg, 41.50 mol), 4-hydroxy-benzaldehyde (4.7 kg, 38.33 mol), potassium carbonate (5.2 kg, 37.33 mol) and tetradecyl trimethylammonium bromide (0.49 kg, 1.46 mol) in toluene (11.4 kg) is slowly brought, under stirring and under nitrogen, to reflux temperature and refluxed for 6 h.

The solution is then concentrated at atmospheric pressure, 3.6 kg of toluene are added and distilled off and this procedure is repeated once again.

The heterogeneous mixture is then cooled to room temperature and the solid is eliminated by filtration. The residual solvent is then eliminated under reduced pressure and to the oily residue 1.4 kg of toluene are added.

The mixture is heated to about 30-35° C. and seeded with a few grams of pure 4-(2-fluorobenzyloxy)benzaldehyde.

The heterogeneous mixture is stirred for 30 min at 30-35° C. and then n-hexane (11 kg) is added in 30 min. to the mixture kept under stirring at 30-35° C.

After cooling to 0-5° C. and stirring for a further hour at this temperature the solid is collected by filtration and dried under reduced pressure to give 8.0 kg (89% yield) of 4-(2-fluorobenzyloxy)benzaldehyde; m.p. 56.7° C. (DSC, 5° C./min), having a GC purity of 98.2 (area %, see Example 24A) and a 3-(2-fluorobenzyl)-4-(2-fluorobenzyloxy)benzaldehyde (VIb) content 0.01% by weight determined by GC (see Example 24B).

(*) The yields reported in this and in the following Examples, when no otherwise specified, are intended as molar yields.

1.1 Further purification of
4-(2-fluorobenzyloxy)benzaldehyde (IVb) by
Crystallization One kilogram of the product prepared according to the procedure described in Example 1 is dissolved in 2 kg of diisopropyl ether at reflux under stirring.

The solution is cooled to 50-55° C. in 10-15 min and seeded with 5 g of highly pure 4-(2-fluorobenzyloxy)benzaldehyde (GC purity 99.9 area %; see Example 24A, and a content of (VIb) lower than 0.005%).

The suspension is cooled to 10-15° C. during 45-60 min and stirred for an additional hour.

The precipitate is finally collected by filtration, washed with cool diisopropyl ether (0.2 Kg) and dried under reduced pressure to give 0.93 kg of 4-(2-fluorobenzyloxy)benzaldehyde with GC purity of 99.8 (area %, see Example 24A) and a content of 3-(2-fluorobenzyl)-4-(2-fluorobenzyloxy)benzaldehyde (VIb) of 0.005% by weight determined by GC according to Example 24B.

1.2 Preparation of
4-(2-fluorobenzyloxy)benzaldehyde (IVb) by Phase
Transfer Catalysis (PTC) Using Different Catalysts 4-(2-Fluorobenzyloxy)benzaldehyde is prepared by alkylation of 4-hydroxybenzaldehyde (0.39 g) with 2-fluorobenzyl chloride by following the same procedure of Example 1, but using three different phase transfer catalysts.

The results are reported in the following Table 5

TABLE 5

| Experiment | Phase Transfer Catalyst PCT | % (VIb) ** | % Yield |
|---|---|---|---|
| 1.2 (a) | Tetrabutyl fosphonium bromide | 0.02 | 85.0 |
| 1.2 (b) | Aliquat 336* | 0.04*** | 88.8 |
| 1.2 (c) | PEG 400 | 0.16*** | 96.0 |

*Aliquat 336: tricaprylylmethylammonium chloride
** % (VIb): content of 3-(2-fluorobenzyl)-4-(2-fluorobenzyloxy)benzaldehyde (GC: % by weight) Example 24B.
***The product may be further purified according to the procedure of Example 1.1 to lower the content of impurity (VIb) below 0.03% by weight (see Example 24B).

1.3 Preparation of
4-(2-fluorobenzyloxy)benzaldehyde (Mb) by Phase
Transfer Catalysis (PTC) in Xylene 4-(2-Fluorobenzyloxy)benzaldehyde is prepared in 87.2% yield with a content of 3-(2-fluorobenzyl)-4-(2-fluorobenzyloxy)benzaldehyde of 0.02% by weight determined by GC (see Example 24B) by reacting 4-hydroxybenzaldehyde (47 g) with 2-fluorobenzyl chloride according to the same procedure of Example 1, but replacing toluene with xylene as the solvent.

1.4 Preparation of 4-(2-fluorobenzyloxy)benzaldehyde (IVb) by Phase Transfer Catalysis Using Potassium Hydroxide as a Base 4-(2-Fluorobenzyloxy)benzaldehyde is prepared in 88% yield with a content of 3-(2-fluorobenzyl)-4-(2-fluorobenzyloxy)benzaldehyde of 0.49% by weight determined by GC (see Example 24B) by reacting 4-hydroxybenzaldehyde (121 g) with 2-fluorobenzyl chloride, according to the same procedure of Example 1, but using potassium hydroxide (108.6 g) instead of potassium carbonate.

This product is further purified by crystallization according to Example 1.1 to lower the content of the impurity (VIb) below 0.03% by weight (see Example 24B).

1.5 Preparation of 4-(2-fluorobenzyloxy)benzaldehyde (IVb) by Phase Transfer Catalysis Using 2-fluorobenzyl bromide 4-(2-Fluorobenzyloxy)benzaldehyde is prepared in 89.2% yield with a content of 3-(2-fluorobenzyl)-4-(2-fluorobenzyloxy)benzaldehyde (VIb) of 0.06% by weight determined by GC (see Example 24B) by reacting 4-hydroxybenzaldehyde (161 g) with 2-fluorobenzyl bromide instead of 2-fluorobenzyl chloride according to the same procedure of Example 1. This product is further purified by crystallization according to Example 1.1 to lower the content of the impurity (VIb) below 0.03% by weight (see Example 24B).

1.6 Preparation of 4-(2-fluorobenzyloxy)benzaldehyde (IVb) in isopropanol

In a reactor, isopropanol (206 kg), potassium carbonate (29.4 kg, 0.21 kmol), potassium iodide (11.4 kg, 0.068 kmol) and 4-hydroxybenzaldehyde (26 kg, 0.21 kmol) are charged. The mixture is stirred at 20-25° C. for 15 min. Then, 2-fluorobenzyl chloride (33 kg, 0.23 kmol) is added. The mixture is heated at reflux under stirring for 3 hours.

The solvent is removed under vacuum to 70 l residual volume. Cyclohexane (70 kg) and water (95 kg) are added, the mixture is heated to 50° C. and stirred at this temperature for 30 min. Stirring is stopped and the phases are allowed to separate.

The organic phase is washed with water (48 Kg) at 50° C. The separated organic phase is concentrated under vacuum to 60 l residual volume.

The heterogeneous mixture is cooled to 20° C. in about 2 hours and stirred at this temperature for 30 min.

The mixture is centrifuged and the solid is washed with cyclohexane.

The wet solid is dried under vacuum to provide the product of the title: 40.2 kg (0.18 kmol); yield: 82% with GC purity of 99.87 (area %, see Example 24A) and a content of 3-(2-fluorobenzyl)-4-(2-fluorobenzyloxy)benzaldehyde (VIb) of 0.063% by weight determined by GC according to Example 24B.

This product is further purified by crystallization according to Example 1.1 to lower the content of the impurity (VIb) below 0.03% by weight (see Example 24B).

1.7 Preparation of 4-(2-fluorobenzyloxy)benzaldehyde (IVb) in ethanol

In a reactor 4-hydroxybenzaldehyde (30.3 g, 248 mmol), ethanol (400 mL), 2-fluorobenzyl chloride (28.92 g; 198 mmol), potassium carbonate (103.8 g, 751 mmol), sodium iodide (1.34 g, 0.05 mmol) are charged. The mixture is heated to reflux under stirring and under nitrogen atmosphere and kept under these conditions for 5 hours.

The mixture is cooled to room temperature and extracted with ethylacetate and washed with 2M sodium hydroxide aqueous solution (3×300 mL). The solvent is evaporated under vacuum to provide the title compound as a yellow oil (40.75 g) having GC purity of 91.77 (area %, see Example 24A) and, 3-(2-fluorobenzyl)-4-(2-fluorobenzyloxy)benzaldehyde (VIb) content of 0.346% by weight determined according to Example 24B.

This product is further purified by crystallization according to Example 1.1 to lower the content of the impurity (VIb) below 0.03% by weight (see Example 24B).

EXAMPLE 2

Preparation of (S)-2-[4-(2-fluorobenzyloxy)benzylamino]propanamide (Ib) of High Purity Degree (One Pot Reaction)

a) A reactor is loaded under stirring with methanol (25 L) and L-alaninamide hydrochloride (2.0 kg) and the mixture is stirred at 23° C. for 15 min (pH value 3.8); then, triethylamine (1.65 kg) and 4-(2-fluorobenzyloxy)benzaldehyde (3.32 kg), prepared according to Example 1.1, are added to the previously prepared solution adjusting the pH value to 8.3. The mixture is stirred at 25° C. for 3 hours (pH 8 of the heterogeneous mixture) and cooled under stirring to 8° C. Sodium borohydride (0.53 kg) is added, subdivided in twenty small portions in 3 hrs to the mixture under stirring, which is maintained for additional 30 min. The reaction mixture is concentrated under vacuum at 40° C. until a residue (5.2 L) is obtained. Toluene (13.9 kg) and water (23.0 L) are added to the reaction mixture with stirring under nitrogen atmosphere. The mixture is heated up to 60° C. and kept at this temperature under stirring for 30 min. After separation of the phases, the organic phase is washed with water (6.4 L) at 60° C. and the water is discharged. The organic phase is cooled to 18° C. in two hours and kept under these conditions for 1 hour.

The heterogeneous mixture is filtered and the solid is washed with toluene (3×1.0 L) and dried at about 40° C. under vacuum to yield 3.96 Kg of the (5)-2-[4-(2-fluorobenzyloxy)benzylamino]propanamide (ralfinamide, Ib) with a HPLC purity of 99.4 (area %) determined according to the method of Example 25A and a C,O-dialkylated (S)-2-[3-(2-fluorobenzyl)-4-(2-fluorobenzyloxy)-benzylamino]propanamide content less than 0.005% by weight determined by HPLC, according to the method of Example 25B.

b) The reaction is carried out under the same conditions described above with the exception that the sodium borohydride is previously dissolved in a mixture of methanol (about 5.8 g of methanol for each gram of sodium borohydride) and 30% sodium hydroxide (about 0.5 g of 30% sodium hydroxide for each gram of sodium borohydride) and then dropped in about 30 min. into the Schiff base blend keeping the temperature at 8° C.

The obtained product has a HPLC purity degree of 99.5% determined according to Example 25A and a content of C,O- dialkylated impurity less than 0.005% by weight determined by HPLC according to Example 25B.

c) Anhydrous triethylamine (19.8 kg, 0.20 kmol) is added at room temperature, under stirring, to a mixture of methanol (275 L) and L-alaninamide hydrochloride (24.4 kg, 0.20 kmol).

4-(2-fluorobenzyloxy)benzaldehyde (40.0 kg, 0.17 kmol), prepared in Example 1.6, is added in about 20 min to the above mixture and the reaction mixture is stirred for 3 hours at 25° C. whereupon the temperature is lowered to 8° C. (mixture A).

In a second reactor, methanol (50 l) and sodium hydroxide 30% in water (3.2 kg) are mixed at 0-5° C. Sodium borohydride powder (6.6 kg, 0.17 kmol) is added to the above mixture, in portions, at 0-5° C. The mixture is stirred for 2 hours at 0-5° C. under nitrogen (mixture B).

The mixture B is added, under stirring and under nitrogen, in about 4 hours to the above reaction mixture A, keeping the temperature at 8° C. The reaction mixture is concentrated under vacuum to a 70 l residual volume. Toluene (170 kg) and water (280 kg) are added, under stirring and under nitrogen, to the residue and the mixture is heated up to 60-65° C. The organic phase is separated and added with water (70 kg) and the two phases mixture is stirred at 60-65° C.

The organic phase is separated and cooled gradually to 20° C. The mixture is centrifuged and the solid is washed with toluene to provide, after drying at reduced pressure, the product of the title (48.4 Kg, 0.16 kmol), yield: 92%.

The HPLC purity of the product is 99.87 (area %, see Example 25A) and the content of C,O-dialkylated (S)-2-[3-(2-fluorobenzyl)-4-(2-fluorobenzyloxy)-benzylamino]propanamide is less than 0.005% by weight (see Example 25B); m.p. 109.5° C. (capillary).

The enantiomeric composition of ralfinamide determined with a chiral HPLC column consists of 100% of S-enantiomer (area %, see Example 26A).

EXAMPLE 3

Preparation of (S)-2-[4-(2-fluorobenzyloxy)benzylamino]propanamide methanesulfonate (Id) of High Purity Degree a) Ralfinamide (2.8 kg, 9.26 mol), prepared as described in Example 2a), is dissolved in 2-propanol (19.5 kg) and kept at 65-70° C. and under stirring under inert atmosphere.

After treatment with charcoal (150 g) and filtration, the solution is seeded with pure ralfinamide methanesulfonate and, methanesulfonic acid (900 g, 9.36 mol) is added in 30 min, under stirring at 50-55° C. The suspension is then cooled to 15-20° C. in 2 hours and the stirring is continued for an additional hour. The solid is finally collected by filtration and dried under reduced pressure to give 3.46 kg (94.0% yield) of ralfinamide methanesulfonate.

The HPLC purity of the obtained product is 99.7 (area %, see Example 25A) and the content of C,O-dialkylated (S)-2-[3-(2-fluorobenzyl)-4-(2-fluorobenzyloxy)-benzylamino]propanamide methanesulfonate is 0.005% by weight (see Example 25B); m.p. 240.9° C. by DSC (5° C./min).

The enantiomeric purity of ralfinamide methanesulfonate determined with a chiral HPLC column is higher than 99.9 (area %, see Example 26A).

b) Ralfinamide (2.8 kg, 9.26 mol), prepared as described in Example 2b), is converted into its methanesulfonate salt by the procedure described above. The yield is 95.8%.

The HPLC purity of the obtained product is 99.6 (area %, see Example 25A) and a content of C,O-dialkylated (S)-2-[3-(2-fluorobenzyl)-4-(2-fluorobenzyloxy)-benzylamino]propanamide methanesulfonate is less than 0.005% by weight (see Example 25B); m.p. 240.6° C. by DSC (5° C./min). The enantiomeric purity of ralfinamide methanesulfonate determined with a chiral HPLC column is higher than 99.8 (area %, see Example 26A).

c) A mixture of 2-propanol (385 kg) and (S)-2-[4-(2-fluorobenzyloxy)benzylamino]propanamide (ralfinamide, 48.1 kg, 0.16 kmol), prepared in Example 2c), is heated under stirring to 60° C. and kept under these conditions until a clear solution is obtained.

Anhydrous methanesulfonic acid is added slowly to the solution at 60° C. The heterogeneous mixture is cooled to 20° C. and stirred at this temperature for 2 hours.

The mixture is centrifuged and the solid is washed with 2-propanol to provide, after drying under vacuum, 61 kg (0.15 kmol) of the product of the title; yield 96%; having HPLC purity 99.83 (area %, see Example 25A) and less than 0.005% by weight of C,O-dialkylated (S)-2-[3-(2-fluorobenzyl)-4-(2-fluorobenzyloxy)-benzylamino]propanamide methanesulfonate (see Example 25B); m.p. 237° C. (capillary).

The enantiomeric composition of ralfinamide methanesulfonate determined with a chiral HPLC column consists of 100% of S-enantiomers (area %, see Example 26A).

EXAMPLE 4

Preparation of (R,S)-2-[4-(2-fluorobenzyloxy)benzylamino]propanamide methanesulfonate (Id, I'd) of High Purity Degree by Using L-alaninamide Base (One Pot Reaction)

a) (R,S)-2-[4-(2-Fluorobenzyloxy)benzylamino]propanamide (Ib,I'b)

L-alaninamide free base, is prepared by adding an equimolar amount of sodium methylate to a solution of L-alaninamide hydrochloride (30 g) in ethanol (351 mL). The mixture is stirred for 30 min under nitrogen at room temperature. The solid is filtered and the solvent is completely removed under vacuum to provide 21.1 g of L-alaninamide.

In a round bottom flask 21.1 g of L-alaninamide is dissolved in 320 g (about 405 mL) of methanol.

After 15 min. at 20° C., 48.8 g of 4-(2-fluorobenzyloxy)benzaldehyde, prepared according to Example 1.1, is added and the mixture is stirred at room temperature for 20 hours.

The mixture is cooled to 8±2° C. and 8 g of solid $NaBH_4$ are added portion wise to the mixture keeping the temperature at 8±2° C.

The reaction mixture is stirred for at least 12 hours then concentrated to a minimum volume.

Toluene (248 mL) and water (355 mL) are added and the biphasic mixture is stirred at 70° C. and then the organic layer is separated.

The organic solution is washed with water (70. mL) at 70° C. then cooled at room temperature obtaining a suspension which is filtered and washed with toluene.

The solid is dried at 40° C. under vacuum, yielding 47.7 g (74.4% yield) of the title product, as white powder.

The HPLC purity of the obtained product is 95.85 (area %, see Example 25A) and a content of C,O-dialkylated (S)-2-[3-(2-fluorobenzyl)-4-(2-fluorobenzyloxy)-benzylamino]propanamide less than 0.005% by weight (see Example 25B).

The R/S enantiomeric ratio of ralfinamide determined with a chiral HPLC column is 52.5/47.5 (area %, see Example 26A).

A further control of the iminoalkylation reaction course shows that the racemization occurs during this step.

b) (R,S)-2-[4-(2-Fluorobenzyloxy)benzylamino]propanamide methanesulfonate (Id,I'd)

In a round bottomed flask 129.5 g of 2-propanol and 16.5 g of the product from step a) are added and heated at 70±3° C. under stirring until a complete solution is obtained.

Keeping the temperature at 70±3° C., 5.2 g of methanesulfonic acid is added drop wise. After stirring for 30 min at 70±3° C., the mixture is cooled slowly to 20±3° C. and then stirred for one hour.

The product is filtered, washed with 2-propanol and dried under vacuum at 40° C., yielding 19.4 g of the title product, as white powder.

Yield: 92%; having HPLC purity 99.74 (area %, see Example 25A) and less than 0.005% by weight of C,O-dialkylated (R,S)-2-[3-(2-fluorobenzyl)-4-(2-fluorobenzyloxy)-benzylamino]propanamide methanesulfonate (see Example 25B). (R,S)ralfinamide thus obtained is shown to be a mixture of enantiomers, S:R=53.8:47.0 (area %, see Example 26A) by a chiral HPLC column.

EXAMPLE 5

Preparation of (R)-2-[4-(2-fluorobenzyloxy)benzylamino]propanamide methanesulfonate (I'd) of High Purity Degree (One Pot Reaction)

a) (R)-2-[4-(2-Fluorobenzyloxy)benzylamino]propanamide (I'b)

A reactor is loaded under stirring with methanol (28 L) and D-alaninamide hydrochloride (2.1 kg) and the mixture is stirred at 23° C. for 15 min; then, triethylamine (1.65 kg) and 4-(2-fluorobenzyloxy)benzaldehyde (3.30 kg), prepared according to Example 1.1, are added to the previously prepared solution. The mixture is stirred at 25° C. for 3 hours and cooled under stirring to 8° C. Sodium borohydride (0.50 kg) is added in small portion in 3 hours under stirring and the mixture is stirred for additional 30 min. The reaction mixture is concentrated under vacuum at 40° C. until a residue (5.0 L) and then toluene (14 kg) and water (25.0 L) are added to the reaction mixture under stirring under nitrogen. The mixture is heated up to 60° C. and kept at this temperature under stirring for 30 min. After separation of the phases, the organic phase is washed with water (7.0 L) at 60° C. and the water is discharged. The organic phase is cooled to 18° C. in two hours and kept under these conditions for 1 hour.

The heterogeneous mixture is filtered and the solid is washed with toluene (3×1.2 L) and dried at about 40° C. under vacuum to provide 3.90 Kg of (R)-2-[4-(2-fluorobenzyloxy)benzylamino]propanamide (I'b) with a HPLC purity of 99.9 (area %) determined according to the method of Example 25A and a $C_{1-10}$-dialkylated (R)-2-[3-(2-fluorobenzyl)-4-(2-fluorobenzyloxy)-benzylamino]propanamide content less than 0.005% by weight determined by HPLC, according to the method of Example 25B.

b) (R)-2-[4-(2-Fluorobenzyloxy)benzylamino]propanamide methanesulfonate (I'd)

The R-enantiomer of ralfinamide obtained according to the above Example 5a) is converted into the methanesulfonate salt by following the same procedure of Example 3a.

The HPLC purity of the obtained product is 99.9 (area %, see Example 25A) and the content of C,O-dialkylated (R)-2-[3-(2-fluorobenzyl)-4-(2-fluorobenzyloxy)-benzylamino]propanamide methanesulfonate is less than 0.005% by weight (see Example 25B); m.p. 241.0° C. by DSC (5° C./min).

The enantiomeric purity of (I'd) determined with a chiral HPLC column is higher than 99.9 (area %, see Example 26B).

EXAMPLE 6

Preparation of (S)-2-[4-(2-fluorobenzyloxy)benzylamino]propanamide methanesulfonate (Id) of High Purity Degree, with Isolation of the Intermediate Schiff Base (S)-2-[4-(2-fluorobenzyloxy)benzylideneamino]propanamide (III b)

a) (S)-2-[4-(2-Fluorobenzyloxy)benzylideneamino]propanamide (IIIb)

To a suspension of 4-(2-fluorobenzyloxy)benzaldehyde (60.0 g, 0.26 mol), prepared as in the Example 1.1 and L-alaninamide hydrochloride (35.7 g, 0.29 mol) in methanol (280 mL), triethylamine (29.1 g, 0.29 mol) is added at room temperature with stirring under nitrogen atmosphere. Stirring is maintained for one additional hour.

The solution is then seeded with a few mg of (S)-2-[4-(2-fluorobenzyloxy)benzylideneamino]propanamide, the temperature is lowered to 5-10° C. and the stirring continued for 2 hours.

The solid is collected by filtration and washed with methanol at 0° C.

After drying at reduced pressure, the title compound, with m.p. 122° C. (capillary), is obtained in 90% yield $^1$H-NMR: (CDCl$_3$, 300 MHz, 298K) δ (ppm, with respect to TMS): 1.46 (3H, d, J=7.0 Hz, CH$_3$); 3.91 (1H, q, J=7.0 Hz, CH—CO); 5.17 (2H, s, O—CH$_2$); 7.02 (2H, d, J=8.9 Hz aromatic H ortho to O—CH$_2$); 7.09 (1H, ddd, J$_{H-F}$=9.78 Hz J$_{orto}$=8.55 Hz J$_{meta}$=1.23 Hz aromatic H ortho to F); 7.15 (1H, dt, J$_{orto}$=7.35 Hz J$_{meta}$=1.23 Hz aromatic H para to F); 7.27-7.40 (1H, m, aromatic H para to CH$_2$); 7.48 (1H, dt, J$_{orto}$=J$_{H-F}$=7.35 Hz J$_{meta}$=1.53 Hz aromatic H ortho to CH$_2$); 7.71 (2H, d, J=8.9 Hz aromatic H ortho to CH=N); 8.17 (1H, s, C=N)

$^{13}$C-NMR: (CDCl$_3$, 75.4 MHz, 298K) δ (ppm): 21.4 (CH$_3$); 63.8 (OCH$_2$); 68.4 (H$_2$NCOCH); 115.0 (d, J$_{C-F}$=22.4 Hz, aromatic CH), 115.5 (d, J$_{C-F}$=20.7 Hz, aromatic CH); 123.7 (d, J$_{C-F}$=14.4 Hz, quaternary aromatic C); 124.5 (bd, aromatic CH); 129.0 (quaternary aromatic C); 129.8 (bd, aromatic CH); 130.1 (bd, 2 aromatic CH); 160.5 (d, J$_{C-F}$=246.4 Hz, quaternary aromatic C); 161.1 (aromatic C—O); 161.1 (C=N); 176.9 (CONH$_2$)

b) (S)-2-[4-(2-Fluorobenzyloxy)benzylamino]propanamide (Ib)

A mixture of (S)-2-[4-(2-fluorobenzyloxy)benzylideneamino]propanamide (IIIb) prepared as described above (30 g) and methanol (180 mL) is cooled under stirring to 2-5° C. Sodium borohydride (3.8 g) is added in eighteen small portions in 90 min to the previously prepared cold mixture keeping the temperature below 5° C. The mixture is then stirred for additional 10 min at 5° C. The reaction mixture is concentrated under vacuum and worked up as described in Example 2 to provide 28.75 g (95% yield) of (S)-2-[4-(2-fluorobenzyloxy)benzylamino]propanamide (ralfinamide, Ib) with a HPLC purity of 99.5 (area %) determined according to the method of Example 25A and a C,O-dialkylated (S)-2-[3-(2-fluorobenzyl)-4-(2-fluorobenzyloxy)-benzylamino]propanamide content less than 0.005% by weight determined by HPLC, according to the method of Example 25B.

c) (S)-2-[4-(2-Fluorobenzyloxy)benzylamino]propanamide methanesulfonate (Id)

Ralfinamide obtained as described in the above Example 6b) is reacted with methanesulfonic acid as described in the Example 3 to provide the methanesulfonate salt (Id) in 95% yield.

The HPLC purity of the obtained product is 99.9 (area %, see Example 25A) and the content of C,O-dialkylated (S)-2-[3-(2-fluorobenzyl)-4-(2-fluorobenzyloxy)-benzylamino] propanamide methanesulfonate is less than 0.005% by weight (see Example 25B); m.p. 240.6° C. by DSC (5° C./min). The enantiomeric purity of ralfinamide methanesulfonate determined with a chiral HPLC column is higher than 99.9 (area %, see Example 26A).

EXAMPLE 7

Preparation of (R)-2-[4-(2-fluorobenzyloxy)benzylamino]propanamide methanesulfonate (I'd) of High Purity Degree, with isolation of the Intermediate Schiff Base (R)-2-[4-(2-fluorobenzyloxy)benzylideneamino]propanamide (III'b)

a) (R)-2-[4-(2-Fluorobenzyloxy)benzylideneamino] propanamide (III'b)

To a suspension of 4-(2-fluorobenzyloxy)benzaldehyde (60.0 g, 0.26 mol), prepared as in the Example 1.1 and D-alaninamide hydrochloride (35.7 g, 0.29 mol) in methanol (280 mL), triethylamine (29.1 g, 0.29 mol) is added at room temperature with stirring under nitrogen atmosphere. Stirring is maintained for one additional hour.

The solution is then seeded with a few mg of (R)-2-[4-(2-fluorobenzyloxy)benzylideneamino]propanamide, the temperature is lowered to 5-10° C. and the stirring continued for 2 hours.

The solid is collected by filtration and washed with methanol at 0° C.

After drying it at reduced pressure, the title compound is obtained in 91% yield with m.p. 121° C. (capillary).

$^1$H-NMR: (CDCl$_3$, 300 MHz, 298K) δ (ppm, with respect to TMS): 1.46 (3H, d, J=7.0 Hz, CH$_3$); 3.91 (1H, q, J=7.0 Hz, CH—CO); 5.17 (2H, s, O—CH$_2$); 7.02 (2H, d, J=8.9 Hz aromatic H ortho to O—CH$_2$); 7.09 (1H, ddd, J$_{H-F}$=9.78 Hz J$_{orto}$=8.55 Hz J$_{meta}$=1.23 Hz aromatic H ortho to F); 7.15 (1H, dt, J$_{orto}$=7.35 Hz J$_{meta}$=1.23 Hz aromatic H para to F); 7.27-7.40 (1H, m, aromatic H para to CH$_2$); 7.48 (1H, dt, J$_{orto}$=J$_{H-F}$=7.35 Hz J$_{meta}$=1.53 Hz aromatic H ortho to CH$_2$); 7.71 (2H, d, J=8.9 Hz aromatic H ortho to CH═N); 8.17 (1H, s, C═N)

$^{13}$C-NMR: (CDCl$_3$, 75.4 MHz, 298K) δ (ppm): 21.4 (CH$_3$); 63.8 (OCH$_2$); 68.4 (H$_2$NCOCH); 115.0 (d, J$_{C-F}$=22.4 Hz, aromatic CH), 115.5 (d, J$_{C-F}$=20.7 Hz, aromatic CH); 123.7 (d, J$_{C-F}$=14.4 Hz, quaternary aromatic C); 124.5 (bd, aromatic CH); 129.0 (quaternary aromatic C); 129.8 (bd, aromatic CH); 130.1 (bd, 2 aromatic CH); 160.5 (d, J$_{C-F}$=246.4 Hz, quaternary aromatic C); 161.1 (aromatic C—O); 161.1 (C═N); 176.9 (CONH$_2$)

b) (R)-2-[4-(2-Fluorobenzyloxy)benzylamino]propanamide (I'b)

A mixture of (R)-2-[4-(2-fluorobenzyloxy)benzylideneamino]propanamide (III'b) (30 g) and of methanol (180 mL) is cooled under stirring to 2-5° C. Sodium borohydride (3.8 g) is added in twenty small portions in 90 min to the previously prepared cold mixture keeping the temperature below 5° C. The mixture is then stirred for additional 10 min at 5° C. The reaction mixture is concentrated under vacuum and worked up as described in Example 2 to provide 28.44 g (94% yield of (R)-2-[4-(2-fluorobenzyloxy)benzylamino]propanamide (I'b) with a HPLC purity of 99.8 (area %) determined according to the method of Example 25A and a C,O-dialkylated (R)-2-[3-(2-fluorobenzyl)-4-(2-fluorobenzyloxy)-benzylamino]propanamide content less than 0.005% by weight determined by HPLC, according to the method of Example 25B.

c) Preparation of (R)-2-[4-(2-fluorobenzyloxy)benzylamino]propanamide methanesulfonate (I'd)

The R-enantiomer of ralfinamide obtained according to the above Example 7b is reacted with methanesulfonic acid as described in the Example 3a to give the methanesulfonate salt (I'd) in 95% yield.

The HPLC purity of the obtained product is 99.9 (area %, see Example 25A) and the content of C,O-dialkylated (R)-2-[3-(2-fluorobenzyl)-4-(2-fluorobenzyloxy)-benzylamino] propanamide methanesulfonate is less than 0.005% by weight (see Example 25B); m.p. 240.6° C. by DSC (5° C./min). The enantiomeric purity of ralfinamide methanesulfonate determined with a chiral HPLC column is higher than 99.8 (area %, see Example 26B).

EXAMPLE 7 A (R,S) 2-[4-(2-Fluorobenzyloxy)benzylamino]propanamide Methanesulfonate (Id,I'd)

a) Methanol (54 mL) and (R,S)alaninamide hydrochloride (10.09 g, 82 mmol) are charged into a 250 mL glass reactor and anhydrous triethylamine (11.36 mL, 96 mmol) is added drop wise at 25° C. 4-(2-fluorobenzyloxy)benzaldehyde (15.99 g, 69 mmol) prepared in Example 1.6 is added in about 10 min and the mixture is stirred for 12 hours at 25° C. (mixture A).

In a second reactor (50 mL), methanol (20 mL) and sodium hydroxide 30% in water (1.3 g) are mixed under stirring and the temperature is lowered to 0.6° C. Sodium borohydride powder (2.61 g, 69 mmol) is added, in portions, to the solution at 1° C. The mixture is stirred for 2 hours at 1° C. under nitrogen (mixture B).

Mixture B is added, under stirring and under nitrogen, in about 30 min to the above mixture A, keeping the temperature at 10° C.

The reaction mixture is stirred for 30 min at 10° C. and concentrated under vacuum to a 20 mL residual volume. Toluene (70 mL) and water (120 mL) are added, under stirring and under nitrogen, to the residue and the mixture is heated up to 60-65° C.

The organic phase is separated and added with water (20 mL) and the mixture stirred at 60-65° C.

The organic phase is separated and cooled gradually to about 7° C. and kept under these conditions for 3 hours.

The mixture is filtered and the solid is washed with toluene (3×5 mL) to provide, after drying at reduced pressure, (R,S) 2-[4-(2-fluorobenzyloxy)benzylamino]propanamide (13.59 g); 65.2% yield. The HPLC purity of the product is 97.73% (area %, see Example 25A) and the content of C,O-dialkylated (R,S)-2-[3-(2-fluorobenzyl)-4-(2-fluorobenzyloxy)-benzylamino]propanamide is 0.020% by weight (see Example 25B).

(R,S)ralfinamide thus obtained is shown to be a mixture of enantiomers S:R=52.3:47.7 (area %, see Example 26A) by a chiral HPLC column.

b) A mixture of 2-propanol (102 mL) and (R,S)-2-[4-(2-fluorobenzyloxy)benzylamino]propanamide (10 g, 33 mmol) prepared in Example. 7 a) is heated under stirring to 70° C. and kept under these conditions until a clear solution is obtained.

Anhydrous methanesulfonic acid (3.18 g; 2.15 mL) is added slowly to the previous solution at 60° C.

The heterogeneous mixture is cooled to 20° C. and stirred at this temperature for 2 hours.

The mixture is centrifuged and the solid is washed with 2-propanol to provide, after drying under vacuum, 10.77 g of the product of the title; 92% yield; having HPLC purity 99.50 (area %, see Example 25A) and 0.009% by weight of C,O-dialkylated (R,S)-2-[3-(2-fluorobenzyl)-4-(2-fluorobenzyloxy)-benzylamino]propanamide methanesulfonate (see Example 25B).

(R,S)ralfinamide thus obtained is shown to be a mixture of enantiomers, S:R=52.8:47.2 (area %, see Example 26A) by a chiral HPLC column.

$[\alpha]^{25}_D$ (c 2% in methanol): 0.0473

EXAMPLE 8

Preparation of (S)-2-[3-(2-fluorobenzyl)-4-(2-fluorobenzyloxy)-benzylamino]propanamide methanesulfonate (IId)

a) 3-(2-Fluorobenzyl)-4-(2-fluorobenzyloxy)benzaldehyde (VIb)

In a 5 L round bottomed flask, 4-hydroxybenzaldehyde (293 g, 2.407 mol), potassium carbonate (315.85 g, 2.287 mol), toluene (900 mL) and 2-fluorobenzyl chloride (1392 g, 9.628 mol) are added in sequence.

Water (150 mL) is added under stirring to the reaction mixture.

The mixture is quickly heated to reflux and kept under this condition for three days.

GC analysis reveals the presence of 3.2% by weight (see Example 24B) of 3-(2-fluorobenzyl)-4-(2-fluorobenzyloxy) benzaldehyde (VIb).

The mixture is cooled to 60° C. and water (1000 mL) is added under stirring. The layers are separated. The organic phase is washed with brine (500 mL); then the solvent is distilled under reduced pressure (10 mmHg) at 35° C. until no more solvent passes over.

The residue is distilled at 3 mmHg collecting the fraction at 180-220° C. The cold distillation residue is dissolved in $CH_2Cl_2$, and the solvent is removed under vacuum to provide the residue. GC purity is 89%, while the starting aldehyde is 0.5%.

Chromatography on silica gel using hexane:ethylacetate=95:5 provides the product (15.7 g) with a GC purity higher than 99%. (area %; for GC conditions see Example 24B). The product has m.p. 71° C. (capillary).

$^1$H-NMR: ($CDCl_3$, 300 MHz, 298K) δ (ppm, with respect to TMS): 4.06 (2H, s, $CH_2$); 5.23 (2H, s, $OCH_2$); 6.95-7.40 (9H, m, aromatic H); 7.67 (1H, bd, J=0.9 Hz, aromatic H ortho to C=O and $CH_2$); 7.76 (1H, dd, $J_1$=2.1 Hz, $J_2$=8.3 Hz, aromatic H ortho to C=O and aromatic CH); 9.84 (1 H, s, CHO).

$^{13}$C-NMR: ($CDCl_3$, 75.4 MHz, 298K) δ (ppm): 29.2 ($CH_2$); 64.1 ($OCH_2$); 111.4 (aromatic CH); 115.4 (d, $J_{C-F}$=22.0 Hz, aromatic CH), 115.5 (d, $J_{C-F}$=21.1 Hz, aromatic CH); 123.3 (d, $J_{C-F}$=14.2 Hz, quaternary aromatic C); 124.1 (d, $J_{C-F}$=2.6 Hz, aromatic CH); 124.5 (d, $J_{C-F}$=3.2 Hz, aromatic CH); 126.6 (d, $J_{C-F}$=15.5 Hz, quaternary aromatic C); 128.2 (d, $J_{C-F}$=8.1 Hz, aromatic CH); 129.6 (d, $J_{C-F}$=6.2 Hz, aromatic CH); 129.6 (quaternary aromatic C); 130.0 (quaternary aromatic C); 130.2 (d, $J_{C-F}$=8.3 Hz, aromatic CH); 131.1 (aromatic CH); 131.3 (d, $J_{C-F}$=4.1 Hz, aromatic CH); 131.8 (aromatic CH); 160.5 (d, $J_{C-F}$=246.8 Hz, quaternary aromatic C); 161.2 (d, $J_{C-F}$=245.1 Hz, quaternary aromatic C); 161.3 (quaternary aromatic C); 191.1 (CHO).

b) (S)-2-[3-(2-Fluorobenzyl)-4-(2-fluorobenzyloxy)-benzylamino]propanamide (IIb)

To 3-(2-fluorobenzyl)-4-(2-fluorobenzyloxy)benzaldehyde (3.56 g, 0.0105 mol) in a 50 mL flask, a solution previously prepared by cautiously adding under stirring triethylamine (1.2 g, 0.0119 mol) to a 17 mL methanol solution of L-alaninamide hydrochloride (1.48 g, 0.0119 mol), is added at room temperature.

This reaction mixture is stirred for 1 hour at room temperature (precipitation of the corresponding imine occurs), and then it is transferred to a 0.18 L autoclave and 0.34 g of wet (50% $H_2O$) Pt/C 5% are added to the mixture.

The air is purged from the autoclave with nitrogen and then hydrogen is introduced at 5.0 bar.

The reaction is performed at a temperature of 35° C. for 3-5 hours.

After cooling to room temperature and eliminating the catalyst by filtration, the solvent is distilled off under reduced pressure until a residue of approximately 6.5 g is obtained. To this residue water (22 mL) is added and kept at this temperature under stirring for at least two hours.

The obtained crystals are filtered and washed with water. The title compound is obtained in 83% yield (0.00872 mol); m.p. 161° C. (capillary).

$^1$H-NMR: ($CDCl_3$, 300 MHz, 298K) δ (ppm, with respect to TMS): 1.32 (3H, d, J=6.7 Hz, $CH_3$); 1.97 (1H, bs, NH); 3.22 (1H, q, J=6.7 Hz, CH—CO); 3.67 (2H, ABq, J=12.8 Hz, diastereotopic H of $NCH_2$); 4.03 (2H, s, $CH_2$); 5.12 (2H, s, $OCH_2$); 5.98 (1H, bs, $NH_2$); 6.89 (1H, d, $J_{orto}$=8.3 Hz, aromatic H ortho to $CH_2NH$ and aromatic CH); 6.95-7.40 (10H, m, aromatic H).

$^{13}$C-NMR: ($CDCl_3$, 75.4 MHz, 298K) δ (ppm): 19.6 ($CH_3$); 29.2 ($CH_2$); 52.0 ($NHCH_2$); 57.7 ($H_2NCOCH$); 63.8 ($OCH_2$); 111.7 (aromatic CH); 115.2 (d, $J_{C-F}$=21.9 Hz, aromatic CH), 115.3 (d, $J_{C-F}$=21.3 Hz, aromatic CH); 124.0 (d, $J_{C-F}$=3.5 Hz, aromatic CH); 124.3 (d, $J_{C-F}$=2.9 Hz, aromatic CH); 124.3 (d, $J_{C-F}$=14.4 Hz, quaternary aromatic C); 127.5 (aromatic CH); 127.6 (d, $J_{C-F}$=15.0 Hz, quaternary aromatic C); 127.8 (d, $J_{C-F}$=7.5 Hz, aromatic CH); 128.8 (quaternary aromatic C); 129.0-130.0 (m, 2 aromatic CH); 130.5 (aromatic CH); 131.3 (d, $J_{C-F}$=4.6 Hz, aromatic CH); 131.8 (quaternary aromatic C); 155.6 (quaternary aromatic C); 160.4 (d, $J_{C-F}$=245.8 Hz, quaternary aromatic C); 161.2 (d, $J_{C-F}$=244.6 Hz, quaternary aromatic C); 178.2 ($CONH_2$).

c) (S)-2-[3-(2-Fluorobenzyl)-4-(2-fluorobenzyloxy)-benzylamino]propanamide methanesulfonate (IId)

In a 0.2 L glass reactor 3.59 g (0.00872 mol) of (S)-3-(2-fluorobenzyl)-4-(2-fluorobenzyloxy)-benzylamino]propanamide base are dissolved in 40.0 mL of 2-propanol. The solution is heated under stirring at 55-60° C. and kept at this temperature for one hour. To this solution, methanesulfonic acid (0.00881 mol) is added in 15 min, and the temperature is lowered to 20° C. in 90 min. After one night the solid is collected by filtration, dried at 50° C. under reduced pressure and then crystallized from methanol to obtain (S)-2-[3-(2-fluorobenzyl)-4-(2-fluorobenzyloxy)-benzylamino]propanamide methanesulfonate in 89% yield; m.p. 190° C. (capillary).

$^1$H-NMR: (DMSO-$d_6$, 300 MHz, 298K) δ (ppm, with respect to TMS): 1.42 (3H, d, J=6.8 Hz, CH$_3$CH); 2.33 (3H, s, CH$_3$SO$_3$); 3.50-4.20 (5H, m, CH—CO, CH$_2$, diastereotopic H of NCH$_2$,); 5.19 (2H, s, OCH$_2$); 6.95-8.00 (11H, m, aromatic H); 9.02 (2H, bs, NH$_2^+$).

$^{13}$C-NMR: (DMSO-$d_6$, 75.4 MHz, 298K) δ (ppm): 16.5 (CH$_3$); 28.8 (CH$_2$); 48.6 (NHCH$_2$); 54.9 (H$_2$NCOCH); 64.3 (OCH$_2$); 112.8 (aromatic CH); 115.0-117.0 (2 aromatic CH); 124.2 (d, J$_{C-F}$=14.4 Hz, quaternary aromatic C); 124.4 (quaternary aromatic C); 124.8 (aromatic CH); 125.0 (aromatic CH); 127.3 (d, J$_{C-F}$=16.1 Hz, quaternary aromatic C); 128.6 (quaternary aromatic C); 128.8 (aromatic CH); 129.0-133.0 (m, 5 aromatic CH); 156.9 (quaternary aromatic C); 160.8 (d, J$_{C-F}$=245.2 Hz, quaternary aromatic C); 160.9 (d, J$_{C-F}$=243.5 Hz, quaternary aromatic C); 171.1 (CONH$_2$).

d) Isolation of (IIb) by Preparative HPLC of ralfinamide methanesulfonate (Id) Containing 0.13% by Weight of (IId)

A sample (100 mg) of (S)-2-[3-(2-fluorobenzyl)-4-(2-fluorobenzyloxy)-benzylamino]propanamide (IIb) is isolated also by preparative HPLC from 200 g of ralfinamide methanesulfonate (Id) prepared according to J. Med. Chem., 1998, 41, 579, method A, that contains said impurity (IIb) as methanesulfonate (IId), in 0.13% by weight.

HPLC analysis on chiral column (see Example 27C) shows a ratio between S enantiomer (RT 7.3) on R enantiomer RT 7.6) higher than 99.5/0.5. The separation is performed, in two stages (Stage 1 and Stage2) (see FIG. 1).

Stage 1

The scope of the first stage is to isolate a crude product enriched in IIb/TFA (Trifluoroacetic acid).

Preparative HPLC conditions are reported below:

Preparative HPLC Conditions:
  Instrument: Waters Delta Prep 4000 (reciprocating pump, gradient controller with low pressure mixer)
    Radial Compression Module Prep LC Base (Waters)
    Jasco 7125 UV-Variable detector, o.p. 0.2 mm
    Merk D2000 printer-plotter
  Column: Delta Pak C18, 15 μm, 40×100 mm (Waters)
  Eluent A: 70/30, Water/Acetonitrile+0.1% TFA
  Eluent B: 30/70, Water/Acetonitrile+0.1% TFA
  Flow rate: 27.0 mL/min
  Gradient: 40 min, isocratic 100% A, then to 100% B in 1 min
  Detection: UV 227 nm
  Injection: 5 g in 50 mL of Water (by pump inlet line D)

Stage 2

This stage is needed to eliminate TFA from IIb/TFA and to further purify (IIb).

IIb/TFA is chromatographed using the preparative HPLC conditions given below.

The fraction 4 and 5 are combined together and evaporated at 40° C. under vacuum until complete removal of acetonitrile. The residual water solution is kept in a refrigerator at 4° C. The insoluble is isolated by filtration and dried under vacuum at room temperature to provide (IIb) (100 mg; HPLC purity 100%).

Preparative HPLC Conditions:
  Instrument: Waters Delta Prep 4000 (reciprocating pump, gradient controller with low pressure mixer)
    Jasco 7125 UV-Variable detector, o.p. 0.2 mm
    Merk D2000 printer-plotter
  Column: Symmetry C18, 7 μm, 20×250 mm (Waters)
  Eluent A: 70/30, Water/Acetonitrile
  Eluent B: 30/70, Water/Acetonitrile
  Flow rate: 15.0 mL/min
  Gradient: 20 min, isocratic 100% A, then to 100% B in 10 min
  Detection: UV 227 nm
  Injection: 50 mL of impurity "IIa/TFA" solution (by pump inlet line D)

EXAMPLE 9

Preparation of (R)-2-[3-(2-fluorobenzyl)-4-(2-fluorobenzyloxy)-benzylamino]propanamide methanesulfonate a) 3-(2-Fluorobenzyl)-4-(2-fluorobenzyloxy)benzaldehyde (VIb)

The compound of the title is prepared according to the Example 8a).

b) (R)-2-[3-(2-fluorobenzyl)-4-(2-fluorobenzyloxy)-benzylamino]propanamide

The compound of the title is prepared by reacting 3-(2-fluorobenzyl)-4-(2-fluorobenzyloxy)benzaldehyde (VIb) prepared as in Example 9a) with D-alaninamide hydrochloride according to the procedure of the Example 8b).

c) (R)-2-[3-(2-fluorobenzyl)-4-(2-fluorobenzyloxy)-benzylamino]propanamide methanesulfonate (II'd)

(R)-2-[3-(2-Fluorobenzyl)-4-(2-fluorobenzyloxy)-benzylamino]propanamide, obtained in step b) is converted into the title compound by the same procedure described in Example 8c).

On the basis of $^1$H-NMR, $^{13}$C-NMR data, structure (II'd) is assigned to the methanesulfonate thus obtained. $^1$H-NMR, $^{13}$C-NMR spectra and m.p. 190° C. (capillary) are fully consistent with those of the S-enantiomer (IId) (see Example 8c).

HPLC analysis on chiral column (see Example 27C) shows a ratio between R-enantiomer (RT 7.6) on S-enantiomer (RT 7.3) higher than 99.5/0.5.

EXAMPLE 9 A

Preparation of (R,S)-2-[3-(2-fluorobenzyl)-4-(2-fluorobenzyloxy)-benzylamino]propanamide methanesulfonate (IId, II'd)

(R,S)-2-[3-(2-fluorobenzyl)-4-(2-fluorobenzyloxy)-benzylamino]propanamide is prepared from 3-(2-fluorobenzyl)-4-(2-fluorobenzyloxy)benzaldehyde (VIb) (5. g), prepared according the previous Example 8a), and (R,S) alaninamide hydrochloride as per the procedure given in Example 8b).

The product is converted into the methanesulfonic acid salt by the procedure described in Example 9c). The salt is obtained in 70% yield from (VIb)

Spectroscopic data are fully consistent with those of the R-enantiomer (II'd) (see Example 9c).

HPLC analysis on chiral column (see Ex 27 C) shows a 1:1 ratio between R-enantiomer (RT 7.6) on S-enantiomer (RT 7.3)

$[\alpha]^{25}_D$ (c 1% in methanol) 0° C.

EXAMPLE 10

Preparation of purified 4-(3-fluorobenzyloxy)benzaldehyde (IVa)

a) To a mixture of 4-hydroxybenzaldehyde (2.28 kg, 18.68 mol), potassium carbonate, (2.84 kg, 20.54 mol), potassium iodide (0.33 kg, 1.98 mol) in ethanol (21.0 kg), 3-fluorobenzyl chloride (2.70 kg, 18.68 mol) is added under stirring, at room temperature.

The mixture is gradually heated to reflux and then kept at that temperature for 6 hours.

The reaction mixture is then allowed to cool to 25° C., the suspension is filtered and the solid is washed with ethanol (1.5 kg); the ethanol solutions are combined and then concentrated at reduced pressure until a residue of approximately 6.0 kg is obtained.

To this residue, toluene (10 kg) and water (2.5 kg) are added, the solvent mixture is stirred vigorously for 30 min and, after separation of the aqueous phase, the organic layer is evaporated to dryness under reduced pressure to provide crude 4-(3-fluorobenzyloxy)benzaldehyde.

To this product dissolved in toluene (3 kg) a seed of 4-(3-fluorobenzyloxy)benzaldehyde is added under stirring at 20-25° C., then n-hexane (6.0 kg) is added in 45 min and the mixture is cooled to 0° C. under stirring.

After 3 hours the solid is filtered and washed with n-hexane (2.0 kg). After drying, 3.95 kg (92.0% yield) of the desired product are obtained, with a gas-cromathographic purity of 99.8 (area %, see Example 24A) and a 3-(3-fluorobenzyl)-4-(3-fluorobenzyloxy)benzaldehyde content of 0.01% by weight determined by G.C. (area %, see Example 24B); m.p. 43.1° C. by DSC 5° C./min.

A further preparation of the title compound is carried out as follow:

b) In a 10 L reactor, 2-propanol (5.51 kg), potassium carbonate (793 g, 5.74 mol), potassium iodide (305 g, 1.84 mol) and 4-hydroxybenzaldehyde (700 g, 5.74 mol) are charged. The mixture is stirred at 20-25° C. for 15 min.

3-fluorobenzyl chloride (871 g, 6.03 mol) is charged in the reactor with the aid of a dropping funnel in about 20 min.

The mixture is heated at reflux under stirring for 3 hours.

After this time, the mixture is cooled to about 50° C. and sampled for in process control.

The solvent is removed under vacuum until a volume of about 1.8 l is reached.

Cyclohexane (1.84 kg) and water (2.5 kg) are added, and then the mixture is heated to 65±3° C. and stirred at this temperature for 30 min. Stirring is stopped and the phases are allowed to separate for 20 min; the water phase is discharged.

Water (1.31 kg) is added to the organic phase and the biphasic mixture stirred for 30 min at 65±3° C. The phases are allowed to separate for 20 min. The water phase is discharged and the organic phase is concentrated under vacuum to a volume of about 3 l at a temperature comprised between 40 and 55° C.

The mixture is cooled to about 30° C., seeded and stirred at this temperature for 30 min.

The mixture is cooled to 20±2° C. and stirred at this temperature for at least 3 hours.

The product is filtered under suction and the solid is washed with cyclohexane (3×150 g).

The wet solid (1.5 kg) is dried at 20-25° C. at a pressure below 100 mbar for 12 hours to provide 1.17 kg (5.09 mol); 88% yield with a gas-cromathographic purity of 99.43 (area %, see Example 24A) and a content of 0.063% by weight determined by G.C. (area %, see Example 24B) 3-(3-fluorobenzyl)-4-(3-fluorobenzyloxy)benzaldehyde (VIa). This product is further purified according to the procedure described in Example 11.1 to yield a product wherein the content of the impurity (VIa) is 0.01% by weight determined by GC (see Example 24B).

EXAMPLE 11

Preparation of 4-(3-fluorobenzyloxy)benzaldehyde (IVa) by Phase Transfer Catalysis A mixture of 3-fluorobenzyl chloride (10 kg, 69.16 mol), 4-hydroxy-benzaldehyde (7.8 kg, 63.88 mol), potassium carbonate (9.46 kg, 68.44 mol) and tetradecyl trimethylammonium bromide (1.03 kg, 3.72 mol) in toluene (30.0 kg) is slowly brought to reflux temperature under stirring and under nitrogen atmosphere, and then refluxed for 7 hours.

The solution is concentrated at room pressure and then 6 kg of toluene are added and distilled off. This procedure is repeated once again.

The heterogeneous mixture is then cooled to room temperature and the solid is eliminated by filtration. The residual solvent is eliminated under reduced pressure and then 2.6 kg of toluene are added to the oily residue. The mixture is stirred at 20-25° C. and seeded with a few grams of pure 4-(3-fluorobenzyloxy)benzaldehyde, and then n-hexane (18 kg) is added in 45 min to the stirred mixture kept at 20-25° C.

After cooling to 3-6° C. and stirring for a further hour at this temperature the solid is collected by filtration and dried under reduced pressure to give 13.5 kg with a 86.3% yield, GC purity 99.8 (area %, see Example 24A) and a 3-(3-fluorobenzyl)-4-(3-fluorobenzyloxy)benzaldehyde content of 0.01% by weight (see Example 24B).

11.1 Further Purification of 4-(3-fluorobenzyloxy)benzaldehyde (IVa) by Crystallization One kilogram of 4-(3-fluorobenzyloxy)benzaldehyde prepared according to Example 10 b), is dissolved in 2 kg of diisopropyl ether at reflux under stirring.

The solution is cooled to 50-55° C. in 10-15 min and seeded with a few grams of pure 4-(3-fluorobenzyloxy)benzaldehyde.

The suspension is cooled to 10-15° C. during 45-60 min and stirred for an additional hour.

The precipitate is finally collected by filtration, washed with cool diisopropyl ether (0.2 kg) and dried under reduced pressure to give 0.90 kg of 4-(3-fluorobenzyloxy)benzaldehyde with GC purity of 99.9 (area %, see Example 24A) and a content of 3-(3-fluorobenzyl)-4-(3-fluorobenzyloxy)benzaldehyde of 0.01% by weight determined by GC (see Example 24B).

11.2 Preparation of 4-(3-fluorobenzyloxy)benzaldehyde (IVa) by Phase Transfer Catalysis Using 3-fluorobenzyl bromide 4-(3-Fluorobenzyloxy)benzaldehyde is prepared in 87.0% yield with a content of 3-(3-fluorobenzyl)-4-(3-fluorobenzyloxy)benzaldehyde of 0.05% by weight determined by GC (see Example 24B) by reacting 4-hydroxybenzaldehyde (26.52 g) with 3-fluorobenzyl bromide according to the same procedure of Example 11 but using 3-fluorobenzyl bromide instead of 3-fluorobenzyl chloride.

The so obtained 4-(3-fluorobenzyloxy)benzaldehyde is purified according to Example 11.1 to yield the title product in 95.0% yield with a content of 3-(3-fluorobenzyl)-4-(3-fluorobenzyloxy)benzaldehyde of 0.01% by weight determined by GC (see Example 24B).

11.3 Preparation of 4-(3-fluorobenzyloxy)benzaldehyde (IVa) by Phase Transfer Catalysis Using 3-fluorobenzyl methanesulfonate 4-(3-Fluorobenzyloxy)benzaldehyde is prepared in 97.5% yield with a content of 3-(3-fluorobenzyl)-4-(3-fluorobenzyloxy)benzaldehyde (VIa) of 0.45% by weight, determined by GC (see Example 24B), by reacting 4-hydroxybenzaldehyde (15.6 g) with 3-fluorobenzyl methanesulfonate instead of 3-fluorobenzyl chloride according to the same procedure of Example 11. This product is further purified according to the procedure of the Example 11.1 to lower the content of impurity (VIa) to 0.01% by weight.

EXAMPLE 12

Preparation of (S)-2-[4-(3-fluorobenzyloxy)benzylamino]propanamide methanesulfonate (Ic) of High Purity Degree (One Pot Reaction)

a) Preparation of (S)-2-[4-(3-fluorobenzyloxy)benzylamino]propanamide (Ia)

In a 2l four necked round bottom flask, equipped with mechanical stirrer, thermometer, reflux condenser and under a flow of nitrogen, L-alaninamide hydrochloride (124.6 g, 0.49 mol) and methanol (840 mL) are charged and stirred for 15 min at 20° C. Triethylamine (49.5 g, 0.49 mol) is added at such a rate that the temperature remains below 30° C. The mixture is stirred for 10 min, whereupon solid 4-(3-fluorobenzyloxy)benzaldehyde (100 g), prepared in Es. 10 b), is added portion wise in about 30 min. After stirring for 3 hours at 20° C., the mixture is cooled to 5° C. and solid $NaBH_4$ (16.4 g, 0.44 mol) is added in ten portion with caution over a period of 1.5 hours. After the end of the addition, the mixture is stirred for 30 min at 5° C. The mixture is concentrated at reduced pressure to a volume of 100-150 mL.

To the residue, toluene (550 mL) and water (750 mL) are added and the temperature raised to 75° C. After stirring for 30 min phases are separated and the organic phase is washed with water (140 mL). After phase separation, the organic phase is cooled to 68° C., seeded and stirred at this temperature for 1 hour. The mixture is cooled to 20° C. in about 2 hours and stirred at this temperature for 2 hours. The solid is isolated by filtration, washed with toluene (2×40 mL) and dried under vacuum to yield 118 g of white solid; 90% yield.

The HPLC purity of the obtained product is 99.95 (area %, see Example 25A) and the content of C,O-dialkylated (S)-2-[3-(3-fluorobenzyl)-4-(3-fluorobenzyloxy)-benzylamino]propanamide is 0.008% by weight (see Example 25B).

The enantiomeric purity of safinamide determined with a chiral HPLC column is 100% (area %, see Example 27A).

$^1$H-NMR ($D_2O$) (Bruker A V300) δ (ppm, with respect to $H_2O$ at 4.7 ppm): 1.43 (3H, d, J=7 Hz, $CH_3$); 2.66 (3H, s, $CH_3SO_3H$); 3.87 (1H, q, J=7 Hz, H-2); 3.97 (2H, bs, $CH_2NR$); 4.89 (2H, s, $CH_2OR$); 6.88 and 7.23 (4H, AA'XX' aromatic p-disubstituted system; 6.90÷7.22 (4H, aromatic H)

$^{13}$C-NMR ($D_2O$) (Bruker A V300) δ ppm: 15.68 ($CH_3$); 38.27 ($CH_3SO_3H$); 48.99 ($CH_2NR$); 54.81 (CH); 69.00 ($OCH_2$); 114.15 (d, $J_{C-F}$=21 Hz, aromatic CH); 114.76 (d, $J_{C-F}$=20 Hz, aromatic CH); 115.38 (aromatic CH); 123.06 (d, $J_{C-F}$=24 Hz, aromatic CH); 123.24; 130.29 (d, $J_{C-F}$=6 Hz, aromatic CH); 131.54 (aromatic CH); 138.76 (d, $J_{C-F}$=7 Hz, aromatic CH); 158.52; 162.89 (d, $J_{C-F}$=245 Hz, C—F); 171.92 (CO)

a1) As an alternative procedure, the reduction is carried out by using a methanolic solution of $NaBH_4$, instead of solid $NaBH_4$.

A methanolic solution of $NaBH_4$ is prepared by adding under stirring and under nitrogen at 0-5° C. $NaBH_4$ (16.4 g) to a mixture of methanol (120 mL) and NaOH 30% aqueous solution (5.8 mL).

In a 2 L four necked round bottomed flask, equipped with mechanical stirrer, thermometer, reflux condenser and under a flow of nitrogen, L-alaninamide hydrochloride (124.6 g, 0.49 mol) and methanol (720 mL) are charged and stirred for 15 min at 20° C. Triethylamine (49.5 g, 0.49 mol) is added at such a rate that the temperature remains below 30° C. The mixture is stirred for 10 min, whereupon solid 4-(3-fluorobenzyloxy) benzaldehyde (100 g), prepared in Example 10b)), is added portion wise in about 30 min. After stirring for 3 hours at 20° C., the mixture is cooled to 5° C. and the previously prepared solution of $NaBH_4$ is cautiously added through a dropping funnel over a period of 1.5 hours. After the end of the addition, the mixture is stirred for 30 min at 5° C. The mixture is concentrated at reduced pressure to a volume of 100-150 mL.

To the residue, toluene (550 mL) and water (750 mL) are added and the temperature raised to 75° C. After stirring for 30 min phases are separated and the organic phase is washed with water (140 mL). After phase separation, the organic phase is cooled to 68° C., seeded and stirred at this temperature for 1 hour. The mixture is cooled to 20° C. in about 2 hours and stirred at this temperature for 2 hours. The solid is isolated by filtration, washed with toluene (2×40 mL), dried at 40° C. under vacuum: 116 g of white solid, 88.5% yield.

The HPLC purity of the product is 100.0% (area %, see Example 25A) and the content of C,O-dialkylated (S)-2-[3-(3-fluorobenzyl)-4-(3-fluorobenzyloxy)-benzylamino]propanamide is 0.009% by weight (see Example 25B).

The enantiomeric purity of safinamide determined with a chiral HPLC column is 100% (area %, see. Example 27A).

b) (S)-2-[4-(3-Fluorobenzyloxy)benzylamino]propanamide methanesulfonate (Ic)

A mixture of (S)-2-[4-(3-fluorobenzyloxy)benzylamino] propanamide (20 g, 66 mmol, prepared in Example 12a) and ethyl acetate (510 g) is heated, under stirring up to 65° C. and kept under these conditions until a clear solution is obtained. Methanesulfonic acid (7 g, 72.6 mmol) is added in 40 min to the solution precooled to 55° C. The mixture is gradually cooled to 20° C. in 3 hours, kept at 20° C. for 2 hours. The heterogeneous mixture is filtered, the solid is dried at reduced pressure at 40° C. to yield 26.1 g of title compound as white powder (99% yield).

The HPLC purity of the obtained product is 99.94% (area %, see Example 25A) and the content of C,O-dialkylated (S)-2-[3-(3-fluorobenzyl)-4-(3-fluorobenzyloxy)-benzylamino]propanamide methanesulfonate is 0.005% by weight (see Example 25B).

The enantiomeric purity of safinamide methanesulfonate determined with a chiral HPLC column is 100% (area %, see Example 27A).

b1) (S)-2-[4-(3-Fluorobenzyloxy)benzylamino]propanamide (20 g, 66 mmol), prepared according to Example 12 a1) is converted to the methanesulfonate salt (Ic) by using the procedure given in Example 12b), yielding 26.2 g of title compound 99% yield.

The HPLC purity of the obtained product is 99.95% (area %, see Example 25A) and the content of C,O-dialkylated (S)-2-[3-(3-fluorobenzyl)-4-(3-fluorobenzyloxy)-benzylamino]propanamide methanesulfonate is 0.005% by weight (see Example 25B).

The enantiomeric purity of safinamide methanesulfonate determined with a chiral HPLC column is 100% (area %, see Example 27A).

EXAMPLE 13

Preparation of (S)-2-[4-(3-fluorobenzyloxy)benzylamino]propanamide methanesulfonate (Ic) of High Purity Degree The product of the title is prepared in a 87% yield by following the same procedure of Example 12 a1) with the exception that the 4-(3-fluorobenzyloxy)benzaldehyde is prepared according to Example 11 and converted the thus obtained (S)-2-[4-(3-fluorobenzyloxy)benzylamino]propanamide into the methanesulfonate (Ic), having 99.7 (area %) purity, determined according to the method of Example 25A and the content of the C,O-dialkylated impurity (IIa) is 0.005% by weight, measured by the method of Example 25B.

EXAMPLE 14

Preparation of (R,S)-2-[4-(3-fluorobenzyloxy)benzylamino]propanamide methanesulfonate (Ic, I'c) of High Purity Degree by Using L-alaninamide Base (One Pot Reaction)

a) (R,S)-2-[4-(3-Fluorobenzyloxy)benzylamino]propanamide (Ia, I'a)

In a 1 L four necked round bottom flask, equipped with mechanical stirrer, thermometer and under a flow of nitrogen, L-alaninamide hydrochloride (59 g, 0.47 mol) and ethanol (690 mL) are added and the mixture stirred at 20±3° C. for 20 min. A 30% solution of sodium methylate in methanol (83.9 g, 0.47 mol) is added in about 15 min. The mixture is stirred for 1 hour at 20±3° C., the solid (NaCl) is filtered off and the clear solution is concentrated under reduced pressure.

The residue is taken up with methanol (640 g, about 800 mL) and 4-(3-fluorobenzyloxy)-benzaldehyde (96.5 g, 0.42 mol, prepared in Example 10 b), is added in portion over a period of 30 min. After stirring for 20 hours at room temperature, the clear solution is cooled to 5±2° C. and solid $NaBH_4$ (15.8 g, 0.42 mol) is cautiously added in portion over a period of 1.5 hours, keeping the temperature below 10° C. After the end of the addition, the mixture is stirred for 30 min at 5±2° C. The mixture is concentrated at reduced pressure to a volume of 100-150 mL.

To the residue, toluene (550 mL) and water (750 mL) are added and the temperature raised to 75±2° C. After stirring for 30 min phases are separated and the organic phase is washed with water (140 mL). After phase separation, the organic phase is cooled to 68±2° C., seeded and stirred at this temperature for 1 hour. The mixture is cooled to 20° C. in about 2 hours and stirred at this temperature for 2 hours. The solid is collected by filtration under suction and washed with toluene (2×40 mL).

The wet solid is dried at 40° C. under vacuum for 12 hours, yielding 70 g of (R,S)-2-[4-(3-fluorobenzyloxy)benzylamino]propanamide in 65% yield with a HPLC purity of 99.88 (area %, see Example 25A) and a content of (R,S)-2-[3-(3-fluorobenzyl)-4-(3-fluorobenzyloxy)benzylamino]propanamide 0.008% by weight determined by HPLC (see Example 2513).

The analysis of the product with a chiral HPLC column, according to the Example 27A, shows that the obtained compound has an R:S ratio of 52:48.

A further control of the iminoalkylation reaction course shows that the racemization occurs during said iminoalkylation step.

b) (R,S)-2-[4-(3-Fluorobenzyloxy)benzylamino]propanamide methanesulfonate (Ic,I'c)

The compound prepared according to Example 14a), is converted into the methanesulfonate salt according to the same procedure of Example 4b), in a 85.0% yield with the HPLC purity of 99.8 (see Example 25A).

The content of impurity (R,S)-2-[3-(3-fluorobenzyl)-4-(3-fluorobenzyloxy)-benzylamino]propanamide methanesulfonate (IIc, II'c), measured by HPLC (see Example 25B), is less than 0.005% by weight.

EXAMPLE 15

Preparation of (R)-2-[4-(3-fluorobenzyloxy)benzylamino]propanamide methanesulfonate (I'c) of High Purity Degree by Using D-alaninamide hydrochloride (One Pot Reaction)

a) (R)-2-[4-(3-Fluorobenzyloxy)benzylamino]propanamide (I'a)

The compound is prepared according to Example 12 a1) by substituting L-alaninamide hydrochloride with D-alaninamide hydrochloride to give (R)-2-[4-(3-fluorobenzyloxy)benzylamino]propanamide in 91% yield with a HPLC purity of 99.8 (area %, see Example 25A) and a content of (R)-2-[3-(3-fluorobenzyl)-4-(3-fluorobenzyloxy)benzylamino]propanamide is 0.005% by weight determined by HPLC (see Example 25B).

b) (R)-2-[4-(3-Fluorobenzyloxy)benzylamino]propanamide methanesulfonate (I'c)

The R-enantiomer of safinamide prepared according to Example 15a) is converted into the methanesulfonate salt (I'c) by following the same procedure of Example 12b in a 92.0% yield, HPLC purity 99.9% (see Example 25A).

The content of impurity (R)-2-[3-(3-fluorobenzyl)-4-(3-fluorobenzyloxy)-benzylamino]propanamide methanesulfonate (II'c) measured by HPLC (see Example 25B) is less than 0.005% by weight. The title compound has m.p. 216.8° C. by DSC (5° C./min).

The enantiomeric purity, measured with a chiral HPLC column, is over 99.9 (area %, see Example 27B).

$^1$H-NMR ($D_2O$) (Bruker A V300) δ (ppm, with respect to $H_2O$ at 4.7 ppm): 1.43 (3H, d, J=7 Hz, $CH_3$); 2.66 (3H, s, $CH_3SO_3H$); 3.87 (1H, q, J=7 Hz, H-2); 3.97 (2H, bs, $CH_2NR$); 4.89 (2H, s, $CH_2OR$); 6.88 and 7.23 (4H, AA'XX' aromatic p-disubstituted system; 6.90÷7.22 (4H, aromatic H)

$^{13}$C-NMR ($D_2O$) (Bruker A V300) δ ppm: 15.68 ($CH_3$); 38.27 ($CH_3SO_3H$); 48.99 ($CH_2NR$); 54.81 (CH); 69.00 ($OCH_2$); 114.15 (d, $J_{C-F}$=21 Hz, aromatic CH); 114.76 (d, $J_{C-F}$=20 Hz, aromatic CH); 115.38 (aromatic CH); 123.06 (d, $J_{C-F}$=24 Hz, aromatic CH); 123.24; 130.29 (d, $J_{C-F}$=6 Hz, aromatic CH); 131.54 (aromatic CH); 138.76 (d, $J_{C-F}$=7 Hz, aromatic CH); 158.52; 162.89 (d, $J_{C-F}$=245 Hz, C—F); 171.92 ($CONH_2$)

A further preparation of the compound of this Example 15 has been carried out as follows:

a1) (R)-2-[4-(3-Fluorobenzyloxy)benzylamino]propanamide (I'a)

In a round bottom flask 12.2 g of D-alaninammide hydrochloride is dissolved in 166.8 mL of methanol and added in sequence with 9.9 g of triethylamine while keeping temperature lower than 30° C. and then with 20 g of 4-(3-fluorobenzyloxy) benzaldehyde. The mixture was stirred at room temperature for 3 hours and then cooled at 8±2° C. and added with 3.3 g of solid $NaBH_4$ keeping the temperature around 8° C. The reaction was stirred for at least 1 hour, concentrated to a minimum volume and then added with toluene (110 mL) and water (152 mL).

The biphasic mixture is stirred at 70° C. and the organic layer is separated and washed with water (30 mL) at 70° C.

The resulting solution is cooled to room temperature, filtered and washed with toluene.

The solid is dried at 40° C. under vacuum, yielding 22.6 g of the title product as white powder (86.1% yield)

$[\alpha]^{25}_D$ (c 2% in methanol): +10.63°

300 MHz $^1$H-NMR (DMSO-d6): 7.55-7.48 (1H, m), 7.37-7.30 (5H, m) 7.26-7.19 (1H, m) 7.02-7.01 (3H, m) 5.19 (2H, s), 3.70 (1H, d), 3.57-5.53 (1H, d), 3.10-3.04 (1H, q), 1.21-1.19 (3H, d).

b1) (R)-2-[4-(3-Fluorobenzyloxy)benzylamino]propanamide methanesulfonate (I'c)

In a round bottomed flask 65 g of 2-propanol and 8.25 g of the compound prepared according to step a1) above are added and heated at 70° C. under stirring until a complete solution is obtained.

Keeping the temperature at 70±3° C., 2.6 g of methanesulfonic acid is added drop wise.

After stirring for 30 min at 70° C., the mixture is cooled slowly to 20° C. and then stirred for an hour.

The product is filtered, washed with isopropanol and dried under vacuum at 40° C., yielding 10 g of the title product as white powder (92% yield)

m.p. 218.4° C. (capillary); $[\alpha]^{25}_D$ (c 2% in methanol): +0.6°

The HPLC purity of the obtained product is 99.88% (area %, see Example 25A) and the content of C,O-dialkylated (R)-2-[3-(3-fluorobenzyl)-4-(3-fluorobenzyloxy)-benzylamino]propanamide methanesulfonate is 0.006% by weight (see Example 25B); m.p. 218.4° C. (capillary).

The enantiomeric purity of R-safinamide methanesulfonate determined with a chiral HPLC column is 100% (area %, see Example 27B).

300 MHz $^1$H-NMR (DMSO-d6): 7.97 (1H, bs), 7.70 (1H, bs), 7.56-7.47 (3H, m), 7.38-7.34 (2H, m), 7.27-7.21 (1H, dt), 7.17-7.15 (2H, d), 5.25 (2H, s), 4.10 (2H, bs), 3.81-3.79 (1H, q), 2.39 (3H, s), 1.50-1.48 (3H, d).

EXAMPLE 16

Preparation of (S)-2-[4-(3-fluorobenzyloxy)benzylamino]propanamide methanesulfonate (Ic) of High Purity Degree, with isolation of the Intermediate Schiff Base (S)-2-[4-(3-fluorobenzyloxy)benzylideneamino]propanamide (IIIa)

a) (S)-2-[4-(3-Fluorobenzyloxy)benzylideneamino] propanamide (IIIa)

To a suspension of 4-(3-fluorobenzyloxy)benzaldehyde (192.0 g 0.83 mol), prepared as in the Example 10, and L-alaninamide hydrochloride (114.2 g, 0.93 mol) in methanol (960 mL), triethylamine (93.12 g, 0.93 mol) is added at room temperature with stirring under nitrogen atmosphere. Stirring is maintained for two additional hours.

The solution is then seeded with a few milligrams of (S)-2-[4-(3-fluorobenzyloxy)benzylideneamino]propanamide, the temperature is lowered to 5-10° C. and the stirring continued for 3 hours.

The solid is collected by filtration and washed with methanol at 2° C. After drying it at reduced pressure, 190.4 g (76.0% yield) of the title compound are obtained with m.p. 112.0° C. by DSC (5° C./min).

$^1$H-NMR (DMSO-$d_6$) (Bruker AV300) δ (ppm, with respect to TMS at 2.55 ppm; DMSO solvent at 3.35 ppm): 1.31 (3H, d, J=7 Hz, $CH_3$); 3.86 (1H, q, J=7 Hz, H-2); 5.18 (2H, s, $CH_2OR$); 7.08 and 7.79 (4H, AA'XX' p-disubstituted aromatic system); 7.10-7.50 (4H, m, aromatic H); 8.27 (1H, s, CH=NR).

$^{13}$C-NMR (DMSO-$d_6$) (Bruken AV300) δ (ppm): 20.5 ($CH_3$); 67.6 (CH); 68.4 ($OCH_2$); 114.1 e 114.4 (d, $J_{C-F}$=21 Hz, aromatic) CH; 114.5 e 114.8 (d, $J_{C-F}$=21 Hz; aromatic CH; 114.8 (aromatic CH); 123.5 (d, $J_{C-F}$=2 Hz, aromatic CH); 129.0 and 129.9 (aromatic CH); 130.4 and 130.5 (d, $J_{CF}$=7 Hz, aromatic CH); 139.6 and 139.7 (d, $J_{C-F}$=6 Hz aromatic quaternary C); 160.2; 160.5 and 163.8 (d, $J_{C-F}$=245 Hz C—F); 160.6 (CH=N); 174.8 (CO)

$[\alpha]^{25}_D$(c 1% in chloroform): +68.1° b) (S)-2-[4-(3-Fluorobenzyloxy)benzylamino]propanamide (Ia)

A mixture of (S)-2-[4-(3-fluorobenzyloxy)benzylideneamino]propanamide (III a) (150 g), prepared as described in Example 16a), and methanol (900 mL) is cooled under stirring to 2-5° C. Sodium borohydride (19.0 g) is added in small portions in 2 hours to the previously prepared cold mixture keeping the temperature below 5° C. The mixture is then stirred for additional 20 min at 5° C. The reaction mixture is concentrated under vacuum and worked up as described in Example 2 to give 135 g (89.2% yield) of (5)-2-[4-(3-fluorobenzyloxy)benzylamino]propanamide (Ia) with a HPLC purity of 98.8 (area % determined according to the method of Example 25A and a C,O-dialkylated (S)-2-[3-(3-fluorobenzyl)-4-(3-fluorobenzyloxy)-benzylamino]propanamide content of 0.005% by weight determined by HPLC, according to the method of Example 25B.

c) (S)-2-[4-(3-Fluorobenzyloxy)benzylamino]propanamide methanesulfonate (Ic)

Safinamide prepared according to Example 16b) is converted into the methanesulfonate salt (Ic) by following the same procedure of Example 12b) in a 94.0% yield with HPLC purity 99.9% (see Example 25A).

The content of the impurity (S)-2-[3-(3-fluorobenzyl)-4-(3-fluorobenzyloxy)-benzylamino]propanamide methanesulfonate (IIc) measured by HPLC (see Example 25B) is less than 0.005% by weight.

The enantiomeric purity, measured with a chiral HPLC column, is over 99.9 (area %, see Example 27A).

EXAMPLE 17

Preparation of (R)-2-[4-(3-fluorobenzyloxy)benzylamino]propanamide methanesolfonate (I'c) of High Purity Degree, with isolation of the Intermediate Schiff Base (R)-2-[4-(3-fluorobenzyloxy)benzylideneamino]propanamide (III'a)

a) (R)-2-[4-(3-Fluorobenzyloxy)benzylideneamino] propanamide (III'a)

In a 250 mL, 4 necked round bottom flask, equipped with mechanical stirrer, thermometer, reflux condenser and under a flow of nitrogen, D-alaninamide hydrochloride (6.1 g) and methanol (80 mL) are charged and stirred for 15 min at 20° C. Triethylamine (5 g) is added at such a rate that the temperature remains below 30° C. The mixture is stirred for 10 min, whereupon solid 4-(3-fluorobenzyloxy)benzaldehyde (10 g, Example 10b) is added portion wise in about 30 min. After stirring for 3 hours at 20° C., the mixture is cooled to 5° C. After stirring for 3 hours at this temperature, the solid is filtered and washed with small amount of pre-cooled methanol. The wet solid is dried under vacuum for 12 hours a 25° C., yielding 6.4 g of title compound as white solid, with 46.4% yield; m.p 111.9.

$[\alpha]_D = -67.9°$ (c=1 in chloroform);

$^1$H-NMR (DMSO-$d_6$) (Bruker AV300) δ (ppm, with respect to TMS at 2.55 ppm; DMSO solvent at 3.35 ppm): 1.31 (3H, d, J=7 Hz, $CH_3$); 3.86 (1H, q, J=7 Hz, H-2); 5.18 (2H, s, $CH_{2O}R$); 7.08 and 7.79 (4H, AA'XX' p-disubstituted aromatic system); 7.10-7.50 (4H, m, aromatic H); 8.27 (1H, s, CH=NR).

$^{13}$C-NMR (DMSO-$d_6$) (Bruken AV300) δ (ppm): 20.5 ($CH_3$); 67.6 (CH); 68.4 ($OCH_2$); 114.1 e 114.4 (d, $J_{C-F}$=21 Hz, aromatic) CH; 114.5 e 114.8 (d, $J_{C-F}$=21 Hz; aromatic CH; 114.8 (aromatic CH); 123.5 (d, $J_{C-F}$=2 Hz, aromatic CH); 129.0 and 129.9 (aromatic CH); 130.4 and 130.5 (d, $J_{CF}$=7 Hz, aromatic CH); 139.6 and 139.7 (d, $J_{C-F}$=6 Hz aromatic quaternary C); 160.2; 160.5 and 163.8 (d, $J_{C-F}$=245 Hz C—F); 160.6 (CH=N); 174.8 (CO)

b) (R)-2-[4-(3-fluorobenzyloxy)benzylamino]propanamide (I'a)

The compound is prepared by using the procedure of Example 16b), but using (R)-2-[4-(3-fluorobenzyloxy)benzylideneamino]propanamide (III'a), prepared in Example 17a) instead of its enantiomer (IIIa).

c) (R)-2-[4-(3-Fluorobenzyloxy)benzylamino]propanamide methanesulfonate (I'c)

(R)-2-[4-(3-Fluorobenzyloxy)benzylamino]propanamide prepared according to Example 17b) is converted into the methanesulfonate salt (I'c) by following the same procedure of Example 12b in a 92% yield.

The content of impurity (R)-2-[3-(3-fluorobenzyl)-4-(3-fluorobenzyloxy)-benzylamino]propanamide methanesulfonate (II'c) measured by HPLC (see Example 25B) is less than 0.005% by weight. The title compound has m.p. 216.8° C. by DSC (5° C./min).

The enantiomeric purity, measured with a chiral HPLC column, is over 99.9 (area %, see Example 27B).

EXAMPLE 17 A (R,S)-2-[4-(3-Fluorobenzyloxy)benzylamino]propanamide methanesulfonate (Ic, I'c)

a) Methanol (80 mL) and (R,S)-alaninamide hydrochloride (15.14 g, 123 mmol) are charged to a 1000 mL glass reactor and anhydrous triethylamine (17.04 mL, 144 mmol) are added drop wise at 25° C.

4-(3-fluorobenzyloxy)benzaldehyde (23.99 g, 103.5 mmol) prepared in Example 10b) is added in about 10 min and the mixture is stirred for 10 hours at 25° C. (mixture A).

In a second reactor (100 mL), methanol (30 mL) and sodium hydroxide 30% in water (1.3 g) are mixed under stirring and the temperature is lowered to 0-6° C. Sodium borohydride powder (3.92 g, 103.5 mmol) is added, in portions, to the solution at 1° C. The mixture is stirred for 2 hours at 1-2° C. under nitrogen (mixture B).

Mixture B is added, under stirring and under nitrogen, in about 30 min to the above mixture A, keeping the temperature at 5-10° C.

The reaction mixture is stirred for 30 min at 5-10° C. and concentrated under vacuum to a 20 mL residual volume. Toluene (120 mL) and water (100 mL) are added, under stirring and under nitrogen, to the residue and the mixture is heated up to 60-65° C.

The organic phase is separated and added with water (30 mL) and the mixture stirred at 60-65° C.

The organic phase is separated and cooled gradually to about 7° C. and kept under these conditions for 3 hours.

The mixture is filtered and the solid is washed with toluene (3×10 mL) to provide, after drying at reduced pressure, (R,S)-2-[4-(3-fluorobenzyloxy)benzylamino]propanamide (21.40 g).

b) 2-propanol (65 g) and (R,S)-2-[4-(3-fluorobenzyloxy)benzylamino]propanamide (8.2 g) prepared in Example 17A a) are charged in a reactor.

The mixture is heated under stirring to 70° C. and kept under these conditions until a clear solution is obtained.

Anhydrous methanesulfonic acid (2.6 g) is added slowly to the previous solution at 70° C.

The heterogeneous mixture is cooled to 20° C. and stirred at this temperature for at least 2 hours.

The mixture is centrifuged and the solid is washed with isopropanol to provide, after drying under vacuum, 9.4 g of the product of the title 86.4% yield having HPLC purity 99.9 (area %, see Example 25A) and less than 0.005% by weight of C,O-dialkylated (R,S)-2-[3-(3-fluorobenzyl)-4-(3-fluorobenzyloxy)-benzylamino]propanamide methanesulfonate (see Example 25B).

(R,S)safinamide thus obtained is shown to be a S:R=50.30:49.70 (area %, see Example 27A) mixture of enantiomers by a chiral HPLC column.

EXAMPLE 18

Preparation of (S)-2-[3-(3-fluorobenzyl)-4-(3-fluorobenzyloxy)-benzylamino]propanamide methanesulfonate (IIc)

a) 3-(3-Fluorobenzyl)-4-(3-fluorobenzyloxy)benzaldehyde (VIa)

In a 4 L round bottomed flask kept under nitrogen atmosphere, 4-hydroxy-benzaldehyde (400 g, 3.28 mol), potassium carbonate (453 g, 3.28 mol), toluene (2 L) and 3-fluorobenzyl chloride (1400 g, 9.68 mol) are added in sequence and the mixture is refluxed under stirring for 5 days. At this point a GC analysis reveals that the reaction mixture contains 4-(3-fluorobenzyloxy)benzaldehyde and 3-(3-fluorobenzyl)-4-(3-fluorobenzyloxy)benzaldehyde in a ratio of 91.4:8.6 (area/area, see Example 24A).

The reaction mixture is cooled to room temperature and then 2 L of water are added under stirring. The organic phase is separated and the solvent is distilled under reduced pressure (20 mmHg) at 35° C. until no more solvent passes over. The pressure is then lowered to 3 mmHg and the external temperature is raised up to 300° C. and the fraction that distils between 255° C. and 265° C., (40.6 g), is collected.

A GC analysis shows an area/area ratio of C,O-dibenzylated derivative (VIa) on the monoalkylated (IVa) of 99.6:0.4. (area, for GC conditions, see Example 24B).

$^1$H-NMR (CDCl$_3$) (Bruker AV300) δ (ppm, with respect to TMS): 4.05 (2H, s, CH$_2$); 5.13 (2H, s, OCH$_2$); 6.85-7.40 (9H, m, aromatic H); 7.73-7.79 (2H, m, aromatic H ortho to C=O); 9.88 (s, CHO).

$^{13}$C-NMR (CDCl$_3$) (Bruker AV300) δ (ppm): 36.1 (CH$_2$); 69.4 (CH$_2$O); 111.4 (aromatic CH); 112.9 and 113.2 (d, J$_{C-F}$=20 Hz, aromatic CH); 113.9 and 114.2 (d, J$_{C-F}$=22 Hz, aromatic CH); 114.9 and 115.0 (d, J$_{C-F}$=21 Hz, aromatic CH; 115.7 e 115.9 (d, J$_{C-F}$=25 Hz aromatic CH); 122.6 (d, J$_{C-F}$=3 Hz, aromatic CH); 124.4 (d, J$_{C-F}$=3 Hz, aromatic CH); 129.6 and 129.8 (d, J$_{C-F}$=8 Hz, aromatic CH); (d, J$_{C-F}$=7 Hz, quaternary aromatic C); 129.9 (C quaternary aromatic C); 130.0 (quaternary aromatic C); 130.1 and 130.2 (d, J$_{C-F}$ 7 Hz, CH aromatic); 131.2 (aromatic CH); 131.5 (aromatic CH); 138.3 (d, J$_{C-F}$=7 Hz, quaternary aromatic C); 142.3 (d, J$_{C-F}$=7 Hz, quaternary aromatic C); 161.0, 161.2 and 164.4 (d, J$_{C-F}$=240, 2 C—F overlapping); 190.8 (CHO).

b) (S)-2-[(3-(3-Fluorobenzyl)-4-(3-fluorobenzyloxy)-benzylamino]propanamide (IIa)

To 3-(3-fluorobenzyl)-4-(3-fluorobenzyloxy)benzaldehyde (35.6 g, 0.105 mol) in a 500 mL flask, a solution previously prepared by cautiously adding under stirring triethylamine (12 g, 0.119 mol) to a 170 mL methanol solution of L-alaninamide hydrochloride (14.8 g, 0.119 mol), is added at room temperature.

This reaction mixture is stirred for 1 hour at room temperature and then it is transferred to a 1.8 L autoclave and 3.4 g of wet (50% H$_2$O) Pt/C 5% is added to the mixture.

The air is purged from the autoclave with nitrogen and then hydrogen is introduced at 5.0 bar.

The reaction is performed at a temperature of 35° C. for 3-5 hours.

After cooling to room temperature and eliminating the catalyst by filtration, the solvent is distilled off under reduced pressure until a residue of approximately 65 g is obtained. To this residue a mixture of ethylacetate (340 mL) and water (250 mL) is added and the heterogeneous mixture is warmed to 40° C. and kept at this temperature without stirring, until two clear phases are obtained. The two phases are separated and the organic one is distilled under reduced pressure, until a residue of approximately 50 g is obtained.

This residue is dissolved in 220 mL of ethyl acetate and the solvent is distilled off under reduced pressure with an external temperature of 40° C. This operation is repeated twice and the title compound is obtained as solid residue (42.4 g).

c) (S)-2-[3-(3-Fluorobenzyl)-4-(3-fluorobenzyloxy)-benzylamino]propanamide methanesulfonate (IIc)

In a 2 L glass reactor 42.4 g (0.103 mol) of (S)-3-(3-fluorobenzyl)-4-(3-fluorobenzyloxy)-benzylamino]propanamide, prepared in Example 18b, are dissolved in 950 mL of ethyl acetate. The solution is heated under stirring at 50-55° C. and kept at this temperature for one hour. To this solution, 14.5 g (0.15 mol) of methanesulfonic acid are added in 20 min, and the temperature is lowered to 20° C. in 90 min. After 30 min the solid is collected by filtration, dried at 50° C. under reduced pressure and then crystallized from methanol (methanol:product 1:5 by weight) to obtain 25.1 g of enantiomerically pure (see Example 27D) (S)-2-[3-(3-fluorobenzyl)-4-(3-fluorobenzyloxy)-benzylamino]propanamide methanesulfonate, m.p. 187° C. (capillary).

$^1$H-NMR (DMSO-d$_6$) (Bruker AV300) δ (ppm, with respect to TMS): 1.44 (3H, d, J=7 Hz, CH$_3$); 2.35 (3H, s, CH$_3$SO$_3$); 3.81 (1H, q, J=7 Hz, H-2), 3.99 (2H, bs, CH$_2$ benzylic); 4.02 (2H, AB system, CH$_2$N—); 5.17 (2H, s, CH$_2$OR); 6.98-7.63 (11H, m, aromatic H); 7.62 and 7.75 (2H, bs, NH$_2$ amide); 9.02 (2H, broad, NH2+).

$^{13}$C-NMR (DMSO-d$_6$) (Bruker AV300) δ (ppm): 15.9 (CH$_3$); 35.5 (CH$_2$); 39.7 (CH$_3$SO$_3$H); 48.1 (CH$_2$NR); 54.4 (CH); 68.4 (OCH$_2$); 112.2 (aromatic CH); 112.7 (d, J$_{C-F}$=22 Hz, aromatic CH); 113.8 (d, J$_{C-F}$=22 Hz, aromatic CH); 114.5 (d, J$_{C-F}$=22 Hz, aromatic CH); 115.2 (d, J$_{C-F}$=22 Hz, aromatic CH); 123.2 (aromatic CH); 123.8; 124.6 (aromatic CH); 128.7 and 130.0 (d, JH$_{C-F}$=6 Hz, aromatic CH); 130.04 (aromatic CH); 130.3 (d, J$_{C-F}$=6 Hz, aromatic CH); 132.6 (aromatic CH); 139.8 (d, J$_{C-F}$=7 Hz); 143.4 (d, J$_{C-F}$=7 Hz); 158.1, 160.5 and 163.7 (d, J$_{C-F}$=240, C—F); 160.6 and 163.8 (d, J$_{C-F}$=240, C—F); 170.5 (CONH$_2$).

d) Isolation of (IIa) by Preparative HPLC of safinamide methanesulfonate (Ic) Containing 0.12% by Weight of (IIc)

A sample (90 mg) of (S)-2-[3-(3-fluorobenzyl)-4-(3-fluorobenzyloxy)-benzylamino]propanamide (IIa) is isolated also by preparative HPLC from 200 g of safinamide methanesulfonate (Ic) prepared according to J. Med. Chem., 1998, 41, 579, method A, that contains said impurity (IIa), as methanesulfonate (IIc), in 0.12% by weight.

Figure 2:
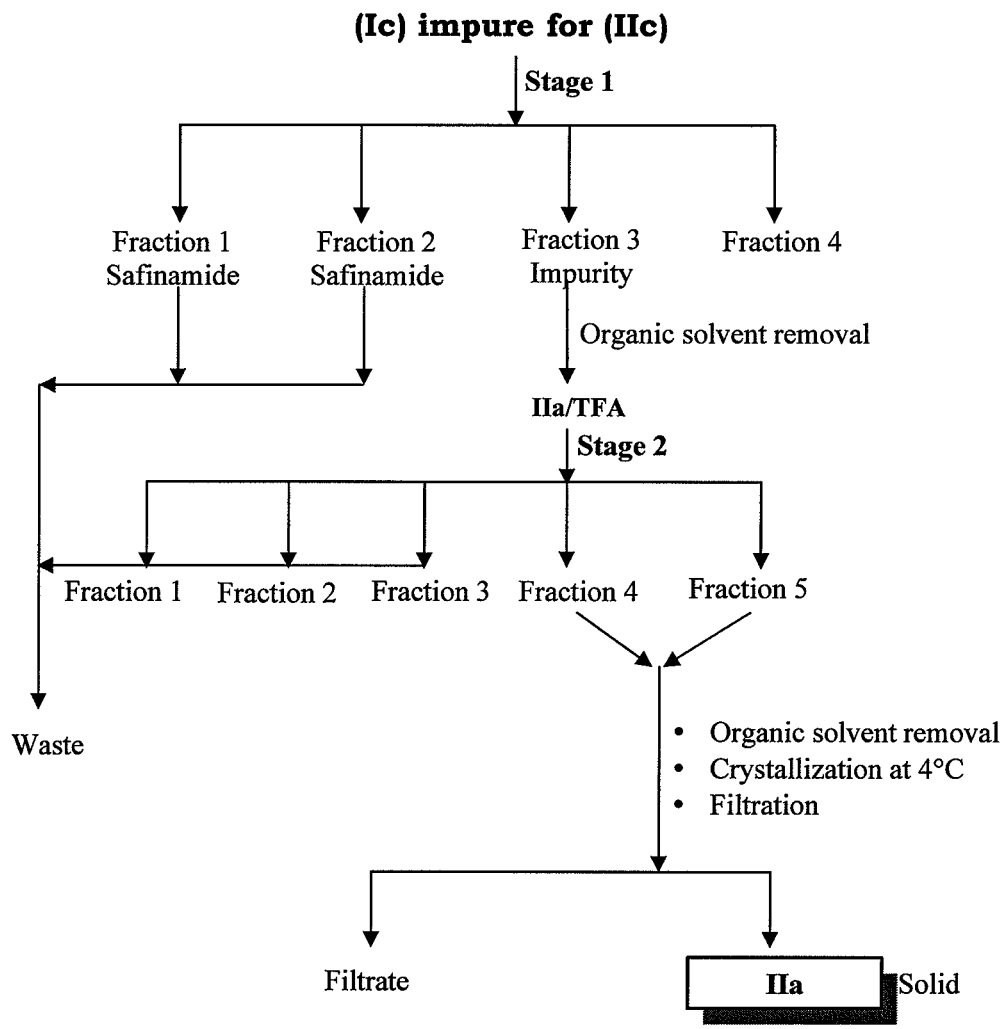
FIG. 2 depicts a two stage isolation procedure of (IIa) as described in Example 18d.

The separation is performed, in two stages (Stage 1 and Stage2) (see FIG. 2).

Stage 1

The scope of the first stage is to isolate a crude product enriched in IIa/TFA (Trifluoroacetic acid).

Preparative HPLC conditions are reported below:
Preparative HPLC conditions:
    Instrument: Waters Delta Prep 4000 (reciprocating pump, gradient controller with low pressure mixer)
    Radial Compression Module Prep LC Base (Waters)
    Jasco 7125 UV-Variable detector, o.p. 0.2 mm
    Merk D2000 printer-plotter
    Column: Delta Pak C18, 15 µm, 40×100 mm (Waters)
    Eluent A: 70/30, Water/Acetonitrile+0.1% TFA
    Eluent B: 30/70, Water/Acetonitrile+0.1% TFA
    Flow rate: 27.0 mL/min
    Gradient: 40 min, isocratic 100% A, then to 100% B in 1 min
    Detection: UV 227 nm
    Injection: 5 g in 50 ml of Water (by pump inlet line D)
Stage 2

This stage is needed to eliminate TFA from IIa/TFA and to further purify (IIa).

IIa/TFA is chromatographed using the preparative HPLC conditions given below.

The fraction 4 and 5 are combined together and evaporated at 40° C. under vacuum until complete removal of acetonitrile. The residual water solution is kept in a refrigerator at 4°

C. The insoluble is isolated by filtration and dried under vacuum at room temperature to provide (IIa) (90 mg; HPLC purity 100%).
Preparative HPLC conditions:
Instrument: Waters Delta Prep 4000 (reciprocating pump, gradient controller with low pressure mixer)
Jasco 7125 UV-Variable detector, o.p. 0.2 mm
Merk D2000 printer-plotter
Column: Symmetry C18, 7 μm, 20×250 mm (Waters)
Eluent A: 70/30, Water/Acetonitrile
Eluent B: 30/70, Water/Acetonitrile
Flow rate: 15.0 mL/min
Gradient: 20 min, isocratic 100% A, then to 100% B in 10 min
Detection: UV 227 nm
Injection: 50 mL of impurity "IIa/TFA" solution (by pump inlet line D)

EXAMPLE 19

Preparation of (R)-2-[3-(3-fluorobenzyl)-4-(3-fluorobenzyloxy)-benzylamino]propanamide methanesulfonate (II'c)

The free base of the above compound is prepared according to the same procedure of the Example 18b but using D-alaninamide hydrochloride instead of L-alaninamide hydrochloride.
(R)-2-[3-(3-fluorobenzyl)-4-(3-fluorobenzyloxy)-benzylamino]propanamide is converted into its methanesulfonate salt according to the procedure of Example 18c.
Thus (II'c) is obtained in 50% yield starting from 3-(3-fluorobenzyl)-4-(3-fluorobenzyloxy)benzaldehyde (VIa).
On the basis of $^1$H-NMR, $^{13}$C-NMR data, the structure (II'c) is assigned to the methanesulfonate thus obtained. $^1$H-NMR, $^{13}$C-NMR spectra and m.p. 196° C. (capillary) are fully consistent with those of the S-enantiomer (IIc) (see Example 18c).

Esempio 19 A

Preparation of (R,S)-2-[3-(3-fluorobenzyl)-4-(2-fluorobenzyloxy)-benzylamino]propanamide methanesulfonate (IIc, II'c)

The title compound is prepared in 75% yield from 2-[3-(3-fluorobenzyl)-4-(3-fluorobenzyloxy)benzaldehyde, prepared in Example 18a) and from racemic alaninamide hydrochloride, by following the procedure given in Example 18b).
The (R,S)-2-[3-(3-fluorobenzyl)-4-(3-fluorobenzyloxy)-benzylamino]propanamide thus obtained is converted in 88% yield into its methanesulfonc acid salt by the procedure given in Example 18c).
HPLC analysis by chiral column (see Example 27D) is fully consistent with the racemic nature of the product.

EXAMPLE 20

Preparation of (S)-2-[4-3-fluorobenzyloxy)benzylamino]propanamide methanesulfonate (Ic) from 4-(3-fluorobenzyloxy)benzaldehyde (IVa) Contaminated by 1% by Weight of Impurity 3-(3-fluorobenzyl)-4-(3-fluorobenzyloxy)benzaldehyde (VIa)

To 4-(3-fluorobenzyloxy)benzaldehyde (10 g; GC purity 98.8, area %), 1% of 3-(3-fluorobenzyl)-4-(3-fluorobenzyloxy)benzaldehyde is added and the mixture is converted into (S)-2-[4-(3-fluorobenzyloxy)benzylamino]propanamide by following the same procedure of Example 12a). The yield is 90% with a content of impurity (IIa) of 0.88% by weight (see Example 25B).
The free base (S)-2-[4-(3-fluorobenzyloxy)benzylamino]propanamide (Ia) is converted into the corresponding methanesulfonate by following the same procedure of Example 12b) to provide the methanesulfonate (Ic) in 96% yield with a content of impurity (S)-2-[3-(3-fluorobenzyl)-4-(3-fluorobenzyloxy)-benzylamino]propanamide methanesulfonate (IIc) of 0.72% by weight determined by HPLC (see Example 25B).

EXAMPLE 21

Crystallization (S)-2-[4-3-fluorobenzyloxy)benzylamino]propanamide methanesulfonate (Ic) Doped with Impurity (IIc)

Samples of safinamide methanesulfonate prepared in the Example 20 are crystallized by using five different(s) solvent systems by dissolving at reflux temperature and cooling at room temperature.
The result are reported in the following Table 6

TABLE 6

| TEST No. | SOLVENT SYSTEM AND AMOUNT (mL/g) | % w/w of (IIc) in (Ic) after crystallization (*) | % Molar Yield |
|---|---|---|---|
| 21a | 2-PrOH/MeOH 2:1, 45 | 0.35 | 42.3 |
| 21b | EtOAc/MeOH 4:1, 50 | 0.20 | 26.6 |
| 21c | EtOH, 10 | 0.37 | 71.2 |
| 21d | Acetone/H$_2$O ~27:1, 40.5 | 0.10 | 18.2 |
| 21e | Acetonitrile/H$_2$O 60:1, 30.5 | 1.1 | 65.0 |

(*) the % (w/w) is evaluated according to Example 25B.

EXAMPLE 22

Preparation of (S)-2-[4-(3-fluorobenzyloxy)benzylamino]propanamide (Ia) methanesulfonate (Ic) According to the Methods Described in the Prior Art 22.1 Preparation of 4-(3-fluorobenzyloxy)benzaldehyde (IVa)

22.1.a) Procedure of Example 1a of U.S. Pat. No. 6,335,354 B2

4-(3-Fluorobenzyloxy)benzaldehyde (IVa) is prepared by the procedure described in Example 1a of U.S. Pat. No. 6,335,354 B2.
Accordingly, a mixture of 3-fluorobenzyl chloride (2.86 g, 19.80 mmol) 4-hydroxybenzaldehyde (3.03 g, 24.80 mmol), K$_2$CO$_3$ (10.30 g, 74.50 mmol), NaI (137.1 mg, 0.91 mmol), and ethanol, (40 mL) is heated to reflux in 70 min and kept at reflux temperature for 4 hours and 15 min.
After working up the reaction mixture, 4-(3-fluorobenzyloxy)benzaldehyde, is isolated as a yellow oil in 95% yield.
The product has GC purity of 97.6 (area %, see Example 25A) and a content of 3-(3-fluorobenzyl)-4-(3-fluorobenzyloxy)benzaldehyde (VIa) of 0.14% by weight determined by GC (see Example 25B)

22.1.b) Procedure of J. Agric. Food Chem, 27, 4, 1979

4-(3-Fluorobenzyloxy)benzaldehyde (IVa) is prepared by the procedure reported in J. Agric. Food Chem, 27, 4, 1979.

Accordingly, 3-fluorobenzyl chloride (14.5 g, 100 mmol) is added under stirring and under nitrogen atmosphere to a solution of 4-hydroxybenzaldehyde (12.2 g, 100 mmol) and of NaOH (4.0 g, 100 mmol) in ethanol (100 mL).

The mixture is gradually heated in 25 min to reflux and stirred at reflux temperature for 6 hours and 20 min. The reaction mixture is filtrated and then concentrated at reduced pressure to obtain 4-(3-fluoro-benzyloxy)benzaldehyde (23.43 g) as a yellow solid residue. Dichloromethane (250 mL) is added to the residue, the insoluble is filtered and the resulting solution is concentrated under reduced pressure to provide 4-(3-fluorobenzyloxy)benzaldehyde as a yellow solid, in 80.4% yield. The product has GC purity of 91.6 (area %, see Example 24A) and a content of 3-(3-fluorobenzyl)-4-(3-fluorobenzyloxy)benzaldehyde (VIa) of 0.13% by weight determined by GC(see Example 25B)

22.2 Preparation of (S)-2-[4-(3-fluorobenzyloxy) benzylamino]propanamide (Ia) and its methanesulfonate salt (Ic)

22.2.a) Procedure of J. Med. Chem., 1998, 41, 579, Method A (S)-2-[4-(3-Fluorobenzyloxy)benzylamino]propanamide (Ia) is prepared by reacting 4-(3-fluorobenzyloxy)benzaldehyde (10 mmol), prepared as described in Example 22.1 a), and L-alaninamide hydrochloride (1.37 g, 11 mmol) followed by reduction with NaBH$_3$CN (0.50 g, 8 mmol). After working up the reaction mixture and purification by flash-chromatography, (S)-2[4-(3-fluorobenzyloxy)benzalamino]propanamide is isolated as white solid in 68.7% yield. The product has HPLC purity of 96.2 (area %, see Example 25A) and a content of (S)-2-[3-(3-fluorobenzyl)-4-(3-fluorobenzyloxy)-benzylamino]propanamide (IIa) of 0.15% by weight (see Example 25B).

A mixture of (S)-2[4-(3-fluorobenzyloxy)benzylamino] propanamide (1.50 g, 4.96 mmol) and ethyl acetate (40.2 mL) is heated to 50° C. until a clear solution is obtained. Methanesulfonic acid (0.53 g, 5.51 mmol) is added under stirring in 15 min to the solution and the resulting heterogeneous mixture is cooled under stirring to 20° C. in 90 min. After 30 min at 20° C. the solid is collected by filtration, washed with ethyl acetate (6 mL) and dried at 50° C. at reduced pressure for 15 hrs to provide (S)-2[4-(3-fluorobenzyloxy)benzylamino]propanamide methanesulfonate (Ic) as a white solid in a 96.1% yield. The product has HPLC purity 98.6 (area %, see Example 25A) and a content of (S)-2-[3-(3-fluorobenzyl)-4-(3-fluorobenzyloxy)-benzylamino]propanamide methanesulfonate (IIc) of 0.10% by weight determined by HPLC (see Example 25B).

22.2.b) Procedure of J. Med. Chem., 1998, 41, 579, Method A (S)-2-[4-(3-Fluorobenzyloxy)benzylamino]propanamide (Ia) is prepared according to Example 22.2.a) from 4-(3-fluorobenzyloxy)benzaldehyde (10 mmol), prepared as described in Example 22.1.b), and L-alaninamide hydrochloride (1.37 g, 1 µmol) followed by reduction with NaBH$_3$CN (0.50 g, 8 mmol).

(S)-2[4-(3-fluorobenzyloxy)benzylamino]propanamide (Ia), is obtained as white solid in 66.5% yield. The product has HPLC purity of 88.5 (area %, see Example 25A) and a content of (S)-2-[3-(3-fluorobenzyl)-4-(3-fluorobenzyloxy)-benzylamino]propanamide (IIa) of 0.064% by weight determined by HPLC (see Example 25B). (S)-2-[4-(3-Fluorobenzyloxy) benzylamino]propanamide (Ia) is converted into the corresponding methanesulfonate (Ic) in a 88.9% yield by treatment with methanesulfonic acid according Example 22.2.a). The product has a HPLC purity of 97.7 (area %, see Example 25A) and a content of (S)-2-[3-(3-fluorobenzyl)-4-(3-fluorobenzyloxy)-benzylamino]propanamide methanesulfonate (IIc) of 0.05% by weight determined by HPLC (see Example 25B).

EXAMPLE 23

Preparation of (S)-2-[4-(2-fluorobenzyloxy)benzylamino]propanamide (ralfinamide, Ib) methanesulfonate (Id) and its R-enantiomers (I'd) According to the Methods Described in the Prior Art

23.1 Preparation of 4-(2-fluorobenzyloxy)benzaldehyde (IVb)

23.1.a) Procedure of Example 1a of U.S. Pat. No. 6,335,354 B2

4-(2-Fluorobenzyloxy)benzaldehyde (IVb) is prepared according to the Example 22.1.a) from 2-fluorobenzyl chloride (14.3 g, 98 mmol), 4-hydroxybenzaldehyde (15.1 g, 123 mmol), K$_2$CO$_3$ (51 g, 369 mmol), NaI (500 mg, 3.3 mmol.) ethanol, 75 mL.

The mixture is kept at reflux for 12 hrs. After working up the reaction mixture, (2-fluorobenzyloxy)benzaldehyde is obtained in 75% yield as a yellow oil. The product has GC purity of 94.21 (area %, see Example 24A) and a content of 3-(2-fluorobenzyl)-4-(2-fluorobenzyloxy)benzaldehyde of 0.39% by weight determined by G.C. (see Example 24B).

23.1.b) Procedure of J. Agric. Food Chem, 27, 4, 1979

4-(2-Fluorobenzyloxy)benzaldehyde (IVb) is prepared according to Example 22.1.b) from 2-fluorobenzyl chloride (18.0 g, 123 mmol), 4-hydroxy-benzaldehyde (15.3 g, 125 mmol), NaOH (5.0 g, 12 mmol) and ethanol (125 mL).

The mixture is heated in 25 min to reflux and kept at reflux temperature under stirring for 12 hours.

After working up the reaction mixture according to Example 22.1.b) 4-(2-fluorobenzyloxy)benzaldehyde is obtained as a yellow solid, in 90.0% yield. The product has GC purity of 90.4 (area %, see Example 24A) and a content of 3-(2-fluorobenzyl)-4-(2-fluorobenzyloxy)benzaldehyde (VIb) of 0.14% by weight determined by G.C. (see Example 24B).

23.2 Preparation of (S)-2-[4-(2-fluorobenzyloxy) benzylamino]propanamide (Ib) and its methanesulfonate salt (Id)

23.2.a) Procedure of J. Med. Chem., 1998, 41, 579, Method A (S)-2-[4-(2-Fluorobenzyloxy)benzylamino]propanamide (Ib) is prepared following the procedure of Example 22.2.a) by using 4-(2-fluorobenzyloxy)benzaldehyde (10 mmol, prepared as in Example 23.1a) instead of 4-(3-fluorobenzyloxy) benzaldehyde.

(S)-2[4-(2-Fluorobenzyloxy)benzalamino]propanamide is obtained in 67.3% yield as a white solid. The product has a HPLC purity of 86.7 (area %, see Example 25A) and a content of (S)-2-[3-(2-fluorobenzyl)-4-(2-fluorobenzyloxy)-benzylamino]propanamide (IIb) of 0.22% by weight determined by HPLC (see Example 25B).

A mixture of (S)-2[4-(2-fluorobenzyloxy)benzylamino]propanamide (1.50 g, 4.96 mmol) and propan-2-ol (10.5 mL) is heated to 50° C. and kept at this temperature until a clear solution is obtained. Methanesulfonic acid, (0.48 g, 5.01 mmol) is added under stirring in 15 min.

The heterogeneous mixture is then cooled under stirring to 20° C. in 2 hours. After 1 hour at 20° C. the solid is collected by filtration, dried at reduced pressure to provide (S)-2[4-(2-fluorobenzyloxy)benzylamino]propanamide methanesulfonate as white solid in 89.1% yield. The product has a HPLC purity of 96.9 (area %, see Example 25A) and a content of (S)-2-[3-(2-fluorobenzyl)-4-(2-fluorobenzyloxy)benzylamino]propanamide methanesulfonate (IId) of 0.14% by weight determined by HPLC (see Example 25B).

23.2.b) Procedure of J. Med. Chem. 1998, 41, 579, Method A (S)-2-[4-(2-Fluorobenzyloxy)benzylamino]propanamide (Ib) is prepared according to Example 22.2.b) by using 4-(2-fluorobenzyloxy)benzaldehyde (10 mmol, prepared according to Example 23.1.b) instead of 4-(3-fluorobenzyloxy)benzaldehyde.

(S)-2-[4-(2-Fluorobenzyloxy)benzylamino]propanamide is obtained as a white solid in 58.8% yield. The product has a HPLC purity 83.8 (area %, see Example 25A) and a content of (S)-2-[3-(2-fluorobenzyl)-4-(2-fluorobenzyloxy)-benzylamino]propanamide (IIb) of 0.15% by weight determined by HPLC (see Example 25B).

(S)-2-[4-(2-fluorobenzyloxy)benzylamino]propanamide (Ib) is converted into the corresponding methanesulfonate (Id) in a 89.4% yield as a white solid. The product has a HPLC purity of 95.2 (area %, see Example 25A) and a content of (S)-2-[3-(2-fluorobenzyl)-4-(2-fluorobenzyloxy)-benzylamino]propanamide methanesulfonate of 0.11% by weight determined by HPLC (see Example 25B).

23.3. Preparation of (R)-2-[4-(2-fluorobenzyloxy) benzylamino]propanamide (I'b) and its methanesulfonate salt (I'd) According to the Procedure of Patent Application WO 2006/027052 a) In a 250 mL glass reactor, dry methanol 109 mL), containing 0.01% water, (pH of the mixture=7.30) D-alaninamide hydrochloride (3 g; 24 mmol) (Nova Biochem A36136821) (pH of the mixture=3.98), (2.43 g; 24 mmol), 4-(2-fluorobenzyloxy)benzaldehyde (5.06 g, 22 mmol) (pH of the mixture=8.60), prepared as described in Example (23.1a) with GC purity 94.21 (area %, see example 24A) and a content of 3-(2-fluorobenzyl)-4-(2-fluorobenzyloxy)benzaldehyde of 0.39% by weigth determined by G.C; see Example 24B, and 3A° molecular sieves (2.19 g) are loaded under stirring and under nitrogen at room temperature. The mixture is heated up to 40° C. and stirred at this temperature for 4 h. The reaction temperature is then lowered to 10° C. (pH of the mixture 8.24) and sodium borohydride (0.42 g, 11 mmol) is added portion wise in 15 min. The reaction mixture is warmed up to room temperature while stirring for additional 6 hours at room temperature. The reaction mixture is filtered and evaporated to dryness under vacuum. The residue is taken up with water (80 mL) and toluene (70 mL) at 60° C., the organic phase is separated and added with water (80 mL). The two phases mixture is warmed up to 60° C. under stirring. The organic phase is separated and added with water (80 mL). The two phases mixture is warmed up to 60° C. under stirring. The organic phase is dried at 60° C. over anhydrous sodium sulphate. The aqueous phases are combined together (solution A, about 240 mL). The toluenic mixture is filtered, and the solution is gradually cooled to 10° C. The mixture is kept under stirring and under nitrogen at 10° C. for 3 hours. The mixture is filtered and the solid is washed with cold (10° C.) toluene (10 mL), dried under vacuum at room temperature to provide 2.13 g (7.1 mmol; 32% yield) of (R)-2-[4-(2-fluorobenzyloxy)benzylamino]propanamide (I'b) as white crystals.

The product has 98.00 (area %, see Example 25A) HPLC purity and a content of (R)-2-[3-(2-fluorobenzyl)-4-(2-fluorobenzyloxy)-benzylamino]propanamide (II'b) of 0.15% by weight determined by HPLC (see Example 25B).

Enantiomeric ratio R:S=99.6:0.4 as determined with a chiral HPLC column (area %, see Example 26B).

The toluenic mother liquor and the toluenic washing are combined together and the solution is concentrated, under vacuum, in a rotary evaporator to provide a yellow residue (1.97 g).

The residue is dissolved in methanol (30 mL) and the known species present in solution are determined quantitatively vs. external standard by HPLC (see Example 25A):
(R)-2-[4-(2-fluorobenzyloxy)benzylamino]propanamide (I'b) (0.81 g; 2.7 mmol);
4-(2-fluorobenzyloxy)benzaldehyde (0.16 g; 0.7 mmol);
4-(2-fluorobenzyloxy)benzyl alcohol (0.53 g: 2.2 mmol) and others non quantified impurities.
(I'b) HPLC purity is 28.65% (area %, see Example 25A)

Aqueous solution A is evaporated in a rotary evaporator, under vacuum, to residue. The residue is suspended in methanol (30 mL), filtered, the solvent evaporated under vacuum to residue (4.5 g). The residue is dissolved in methanol (30 mL) and the known species present in solution are determined quantively vs. external standard by HPLC (see Example 25A): (R)-2-[4-(2-fluorobenzyloxy)benzylamino]propanamide (I'b) (0.69 g; 2.3 mmol);
4-(2-fluorobenzyloxy)benzaldehyde (0.07 g; 0.3 mmol);
4-(2-fluorobenzyloxy)benzylalcohol (0.06 g: 0.2 mmol) and others non quantified impurities.
(I'b) HPLC purity is 53.87% (area %, see Example 25A).

As per above, the overall quantity of (I'b) produced is 3.63 g; 12.1 mmol; 55% yield. The mass balance accounts for about 90% of the charged 4-(2-fluorobenzyloxy)benzaldehyde.

b) To a solution of (R)-2-[4-(2-fluorobenzyloxy)benzylamino]propanamide (1.28 g; 4 mmol) (purity 98.00%, obtained according to step a), content of (R)-2-[3-(2-fluorobenzyl)-4-(2-fluorobenzyloxy)-benzylamino]propanamide (II'b) of 0.15% by weight, in ethyl acetate (21 mL), a solution of methanesulfonic acid (0.27 mL) in ethyl acetate (5 mL) is added drop wise under stirring at room temperature. After 1 hour the white crystals are isolated by filtration, washed with ethyl acetate (3 mL) and dried under vacuum to give 1.40 g (86% yield) of the title compound. The product has a HPLC purity of 99.25 (area %, see Example 25A) and a content of (R)-2-[3-(2-fluorobenzyl)-4-(2-fluorobenzyloxy)benzylamino]propanamide methanesulfonate (II'd) of 0.07% by weight determined by HPLC (see Example 25B).

The preparation described above has been repeated on a larger scale as follows:
a1) In a 50 L glass reactor, dry methanol 21.43 L, containing 0.01% water, D-alaninamide hydrochloride (589.9 g; 4.72 mol), triethylamine (477.8 g; 4.72 mol) 4-(2-fluorobenzyloxy)benzaldheyde (1000 g, 4.33 mol) prepared as described in Example 23.1a) with GC purity 93.20 (area %, see Example 24A) and a content of 3-(2-fluorobenzyl)-4-(2-fluorobenzyloxy)benzaldehyde of 0.43% by weigth determined by GC (see Example 24B), and 3A° molecular sieves (430.62 g) are loaded under stirring and under nitrogen at room temperature. The mixture is heated up to 40° C. and stirred at this temperature for 4 hours. The reaction temperature is then lowered to 10° C. and sodium borohydride (82.58 g, 2.16 mol) is added portion wise in 30 min. The reaction mixture is warmed up to room temperature while stirring for additional 6 hours at 20±2° C. The reaction mixture is filtered and evaporated to dryness under vacuum. The residue is taken up with water (16 L) and toluene (14 L) at 60° C., the organic phase is separated and added with water (16 L). The two phases mixture is warmed up to 60° C.±2 under stirring. The organic phase is separated and added with water (16 L). The two phases mixture is warmed up to 60° C.±2 under stirring. The organic phase is dried by azeotropic distillation at about 60° C. under vacuum. The aqueous phases are combined together (solution A, about 50 L). The toluenic solution is gradually cooled to 10° C. The mixture is kept under stirring and under nitrogen at 10° C.±2 for 4 hours. The mixture is filtered and the cake is washed with cold (10° C.) toluene (2 L), dried under vacuum at room temperature to provide 393.3 g (1.31 mol; 30.3% yield) of (R)-2-[4-(2-fluorobenzyloxy)benzylamino]propanamide (I'b) as white solid. The product has 97.70 (area %, see Example 25A) HPLC purity and a content of (R)-2-[3-(2-fluorobenzyl)-4-(2-fluorobenzyloxy)-benzylamino]propanamide (II'b) of 0.16% by weight determined by HPLC (see Example 25B).

Enantiomeric ratio R:S=99.5:0.5 (area %, see Example 26B) as determined with a chiral HPLC column.

b1) To a solution of (R)-2-[4-(2-fluorobenzyloxy)benzylamino]propanamide 393.3 g (1.31 mol) obtained according to step a1) having GC purity 97.70 (area %, see Example 24A) and a content of (R)-2-[3-(2-fluorobenzyl)-4-(2-fluorobenzyloxy)-benzylamino]propanamide (II'b) of 0.16% by weight determined by CG (see Example 24B), in ethyl acetate (6.5 L), a solution of methanesulfonic acid (83 mL) in ethyl acetate (1.5 L) is added under stirring at room temperature. After 1 hour the white crystals are isolated by filtration, washed with ethyl acetate (3 mL) and dried under vacuum to give 420.1 g (84% yield) of the title compound.

The product has a HPLC purity of 99.15 (area %, see Example 25A) and a content of (R)-2-[3-(2-fluorobenzyl)-4-(2-fluorobenzyloxy)benzylamino]propanamide methanesulfonate (II'd) of 0.08% by weight determined by HPLC (see Example 25B).

The above data show that, even taking into consideration the amount of compound (I'b) which are not recovered as the end product from the process disclosed in WO 2006/027052 (see under step a) above), the yields are not satisfactory for an industrial scale production of compound (I'b).

EXAMPLE 24A

GC Determination of 4-(3-fluorobenzyloxy)benzaldehyde (IVa) and 4-(2-fluorobenzyloxy)benzaldehyde Purity (IVb)

Test Preparation
Dissolve about 100 mg of the sample in 10 mL of methylene chloride.
Chromatographic Conditions
The chromatographic procedure is carried out by using:
a fused silica capillary column 60 m long and 0.32 mm internal diameter. RTX 35 (35% Diphenyl-65% Dimethyl polysiloxane) Film thickness=0.25 µm;
helium as carrier gas at a pressure of 150 kPa;
a split flow of 25 mL/min;
injector temp. 290° C.;
detector (FID) temp. 290° C.;
with the following temperature program:

| Time (min) | Temperature (° C.) | Rate (° C./min) | Comment |
|---|---|---|---|
| 0-5 | 150 | — | isothermal |
| 5-11 | 150→240 | 15 | linear gradient |
| 11-19 | 240 | — | isothermal |
| 19-20.7 | 240→290 | 30 | linear gradient |
| 20.7-40 | 290 | — | isothermal |

Procedure
Inject 1 µL of the Test Preparation. Record the chromatogram and calculate the product purity by area percent calculation.
Impurities Identification
4-(3-Fluorobenzyloxy)benzaldehyde (IVa):
Retention Times:
4-(3-Fluorobenzyloxy)benzaldehyde retention time is about 17.
4-Hydroxybenzaldehyde relative retention time is about 0.52.
4-(2-Fluorobenzyloxy)benzaldehyde relative retention time is about 0.98.
4-(4-Fluorobenzyloxy)benzaldehyde relative retention time is about 1.01.
4-Benzyloxybenzaldehyde relative retention time is about 1.02.
3-(3-Fluorobenzyl)-4-(3-fluorobenzyloxy)benzaldehyde relative retention time is about 1.78.
4-(2-Fluorobenzyloxy)benzaldehyde (IVb):
Retention Times:
4-(2-Fluorobenzyloxy)benzaldehyde retention time is about 17.
4-Hydroxybenzaldehyde relative retention time is about 0.53.
4-(3-Fluorobenzyloxy)benzaldehyde relative retention time is about 1.02.
4-(4-Fluorobenzyloxy)benzaldehyde relative retention time is about 1.03.
4-Benzyloxybenzaldehyde relative retention time is about 1.04.
3-(2-Fluorobenzyl)-4-(2-fluorobenzyloxy)benzaldehyde relative retention time is about 1.81.

EXAMPLE 24B

GC determination of the content of 3-(2-fluorobenzyl)-4-(2-fluorobenzyloxy)benzaldehyde (VIb) in 4-(2-fluorobenzyloxy) benzaldehyde (Mb) and of 3-(3-fluorobenzyl)-4-(3-fluorobenzyloxy) benzaldehyde (VIa) in 4-(3-fluorobenzyloxy)benzaldehyde (IVa)

The known related substance taken into consideration for 4-(2-fluorobenzyloxy)benzaldehyde is the 3-(2-fluorobenzyl)-4-(2-fluorobenzyloxy)benzaldehyde and for 4-(3-fluorobenzyloxy)benzaldehyde is the 3-(3-fluorobenzyl)-4-(3-fluorobenzyloxy)benzaldehyde. The determination is carried out according to the following conditions:

Internal Standard Solution

Prepare a 3,4,5-trimethoxybenzaldehyde solution with concentration 1.5 mg/mL in methylene chloride (IS).

Reference Solution for the 3-(2-fluorobenzyl)-4-(2-fluorobenzyloxy) benzaldehyde Determination in the 4-(2-fluorobenzyloxy)benzaldehyde Accurately weigh about 20 mg of 3-(2-fluorobenzyl)-4-(2-fluorobenzyloxy)benzaldehyde reference standard and 20 mg of 4-(2-fluorobenzyloxy)benzaldehyde reference standard in a 20 mL volumetric flask, dissolve and dilute to volume with diluent; transfer 500 µL of this solution in a 5 mL volumetric flask, add 500 µL of IS solution and dilute to volume with diluent to obtain a solution containing 3-(2-fluorobenzyl)-4-(2-fluorobenzyloxy)benzaldehyde and 4-(2-fluorobenzyloxy)benzaldehyde at about 100 µg/mL (corresponding to about 0.10%).

Reference Solution for the 3-(3-fluorobenzyl)-4-(3-fluorobenzyloxy) benzaldehyde Determination in the 4-(3-fluorobenzyloxy)benzaldehyde Accurately weigh about 20 mg of 3-(3-fluorobenzyl)-4-(3-fluorobenzyloxy)benzaldehyde reference standard and 20 mg of 4-(3-fluorobenzyloxy)benzaldehyde reference standard in a 20 mL volumetric flask, dissolve and dilute to volume with diluent; transfer 500 µL of this solution in a 5 mL volumetric flask, add 500 µL of IS solution and dilute to volume with diluent to obtain a solution containing 3-(3-fluorobenzyl)-4-(3-fluorobenzyloxy)benzaldehyde and 4-(3-fluorobenzyloxy)benzaldehyde at about 100 µg/mL (corresponding to about 0.10%).

Test Solution:

Accurately weigh about 500 mg of test product in a 5 mL volumetric flask, add 500 µL of IS solution, dissolve and dilute to volume with diluent to obtain a solution having known concentration of about 100 mg/mL.

Chromatographic Conditions:

The chromatographic procedure is carried out by using:
- Column: a fused silica capillary column RTX 35 (35% Diphenyl-65% Dimethyl polysiloxane) 60 m long, 0.32 mm I.D., film thickness 0.25 µm;
- Carrier (helium) at pressure of 150 kPa;
- Split flow 25 mL/min;
- Injector temp. 290° C.;
- Detector (FID) temp. 290° C.;
- Temperature program: 0-5 min isothermal at 150° C., 5-11 min linear from 150° C. to 240° C. at a rate of 15° C./min, 11-19 min isothermal at 240° C., 19-21 min linear from 240° C. to 290° C. at a rate of 30° C./min, 21-40 min isothermal at 290° C.;
- diluent: methylene chloride
- injection volume 1 µL.

Procedure:

Inject blank (diluent), reference solution, test solution and record the chromatograms.

In the reference chromatogram verify that:
4-(2-Fluorobenzyloxy)benzaldehyde retention time is about 18 min;
3-(2-Fluorobenzyl)-4-(2-fluorobenzyloxy)benzaldehyde relative retention time is about 1.7 or 4-(3-Fluorobenzyloxy)benzaldehyde retention time is about 18 min;
3-(3-Fluorobenzyl)-4-(3-fluorobenzyloxy)benzaldehyde relative retention time is about 1.7
3,4,5-Trimethoxybenzaldehyde (IS) relative retention time is about 0.7

Calculate the percent content of 3-(2-fluorobenzyl)-4-(2-fluorobenzyloxy)benzaldehyde in the 4-(2-fluorobenzyloxy) benzaldehyde examined or of the 3-(3-fluorobenzyl)-4-(3-fluorobenzyloxy)benzaldehyde in the 4-(3-fluorobenzyloxy) benzaldehyde examined by internal standard calculation.

The value of the limit of quantization (LOQ) for (3-(2-fluorobenzyl)-4-(2-fluorobenzyloxy)benzaldehyde and of 3-(3-fluorobenzyl)-4-(3-fluorobenzyloxy)benzaldehyde is 0.005% by weight. The value of the limit of detection (LOD) for both considered impurities is 0.0025% by weight.

EXAMPLE 25A

HPLC Purity Determination of (S)-2-[4-(3-fluorobenzYloxY) benzylamino]propanamide (Ia), its methanesulfonate (Ic), (S)-2-[4-(2-fluorobenzyloxy) benzylamino]propanamide (Ib) and its methanesulfonate (Id)

The following chromatographic procedure is suitable for both the free base form (Ia) and (Ib) and the methanesulfonate salt (Ic) and (Id) of the products.

Diluent

Mobile phase.

Test Solution

Accurately weigh about 25 mg of product in a 25 mL volumetric flask, dissolve in and dilute to volume with diluent to obtain a solution having known concentration of about 1.0 mg/mL.

Chromatographic Condition

The chromatographic procedure is carried out by using:
- Column: Waters Symmetry C8, 150×4.6 mm, 5 µm size;
- detection: UV 220 nm;
- column temperature: 30° C.
- mobile phase: 40% solvent A+10% solvent B+50% solvent C, containing 1.0 g/L sodium octansuiphonate;
  - solvent A: Buffer solution=$KH_2PO_4$ 0.05M;
  - solvent B: Acetonitrile;
  - solvent C: Methanol;
- isocratic elution, run time: 60 min;
- flow rate: 1.0 mL/min;
- injection volume: 10 µL.

Procedure

Inject the test solution, record the chromatogram and calculate the product purity by area percent calculation.

(S)-2-[4-(3-Fluorobenzyloxy)benzylamino]propanamide (safinamide) and Related Impurities Identification Retention Time:

(S)-2-[4-(3-Fluorobenzyloxy)benzylamino]propanamide retention time is about 5.5 min.

(S)-2-[4-(3-Fluorobenzyloxy)benzylamino]propionic acid relative retention time is about 0.73.

(S)-2-[3-(3-Fluorobenzyl)-4-(3-fluorobenzyloxy)-benzylamino]propanamide relative retention time is about 4.08.

(S)-2-[4-(2-Fluorobenzyloxy)benzylamino]propanamide (ralfinamide) and related impurity identification Retention Time:

(S)-2-[4-(2-Fluorobenzyloxy)benzylamino]propanamide retention time is about 5.5 min.

(S)-2-[4-(2-Fluorobenzyloxy)benzylamino]propionic acid relative retention time is about 0.73.

(S)-2-[3-(2-Fluorobenzyl)-4-(2-fluorobenzyloxy)-benzylamino]propanamide relative retention time is about 4.08.

The same procedure and reference values are used for determining the purity of the R-enantiomers (I'a), (I'b), (I'c), (I'd) and the respective racemic mixtures.

EXAMPLE 25B

HPLC Determination of (S)-2-[3-(2-fluorobenzyl)-4-(2-fluorobenzyloxy) benzylamino]propanamide (free base IIb, and methanesulfonate IId) in (S)-2-[4-(2-fluorobenzyloxy)benzylamino]propanamide (free base Ib, and methanesulfonate Id) and of (S)-2-[3-(3-fluorobenzyl)-4-(3-fluorobenzyloxy)benzylamino] propanamide (free base IIa, and methanesulfonate IIc) in (S)-2-[4-(3-fluorobenzyloxy)benzylamino] propanamide (free base Ia, and methanesulfonate Ic)

The determination of the (S)-2-[3-(2-fluorobenzyl)-4-(2-fluorobenzyloxy)benzylamino]propanamide (free base and methanesulfonate) in (S)-2-[4-(2-fluorobenzyloxy)benzylamino]propanamide (free base and methanesulfonate) samples and of (S)-2-[3-(3-fluorobenzyl)-4-(3-fluorobenzyloxy)benzylamino]propanamide (free base and methanesulfonate) in (S)-2-[4-(3-fluorobenzyloxy)benzylamino]propanamide (free base and methanesulfonate) samples is carried out according to the following conditions:

Reference Solution for the (S)-2-[3-(2-fluorobenzyl)-4-(2-fluorobenzyloxy)benzylamino]propanamide determination in the (S)-2-[4-(2-fluorobenzyloxy) benzylamino]propanamide Accurately weigh about 30 mg of (S)-2-[3-(2-fluorobenzyl)-4-(2-fluorobenzyloxy)benzylamino]propanamide methanesulfonate reference standard and 20 mg of (S)-2-[4-(2-fluorobenzyloxy)benzylamino]propanamide reference standard in a 50 mL volumetric flask, dissolve and dilute to volume with diluent; dilute 1.0 mL of this solution to 20 mL with diluent ($1^{st}$ dilution); dilute 1.0 mL of the last solution to 20 mL with diluent ($2^{nd}$ dilution) to obtain a solution containing 2-[3-(2-fluorobenzyl)-4-(2-fluorobenzyloxy)benzylamino]propanamide (about 0.12%) at about 1.20 µg/mL and (S)-2-[4-(2-fluorobenzyloxy)benzylamino]propanamide methanesulfonate at about 1.00 µg/mL (about 0.10%).

Reference Solution for the (S)-2-[3-(2-fluorobenzyl)-4-(2-fluorobenzyloxy)benzylamino]propanamide methanesulfonate Determination in the (S)-2-[4-(2-fluorobenzyloxy)benzylamino]propanamide methanesulfonate Accurately weigh about 30 mg of (S)-2-[3-(2-fluorobenzyl)-4-(2-fluorobenzyloxy)benzylamino]propanamide methanesulfonate reference standard and 20 mg of (S)-2-[4-(2-fluorobenzyloxy)benzylamino]propanamide methanesulfonate reference standard in a 50 mL volumetric flask, dissolve and dilute to volume with diluent; dilute 1.0 mL of this solution to 20 mL with diluent ($1^{st}$ dilution); dilute 1.0 mL of the last solution to 20 mL with diluent ($2^{nd}$ dilution) to obtain a solution containing 2-[3-(2-fluorobenzyl)-4-(2-fluorobenzyloxy)benzylamino]propanamide (about 0.15% as methanesulfonic salt) at about 1.20 µg/mL and (S)-2-[4-(2-fluorobenzyloxy)benzylamino]propanamide methanesulfonate at about 1.00 µg/mL (about 0.10%).

Reference Solution for the (S)-2-[3-(3-fluorobenzyl)-4-(3-fluorobenzyloxy)benzylamino]propanamide in the (S)-2-[4-(3-fluorobenzyloxy)benzylamino]propanamide Accurately weigh about 24 mg of (S)-2-[3-(3-fluorobenzyl)-4-(3-fluorobenzyloxy)benzylamino]propanamide reference standard and 20 mg of (S)-2-[4-(3-fluorobenzyloxy) benzylamino]propanamide reference standard in a 50 mL volumetric flask, dissolve and dilute to volume with diluent; dilute 1.0 mL of this solution to 20 mL with diluent (1st dilution); dilute 1.0 mL of the last solution to 20 mL with diluent ($2^{nd}$ dilution) to obtain a solution containing 2-[3-(3-fluorobenzyl)-4-(3-fluorobenzyloxy)benzylamino]propanamide (about 0.12%) at about 1.20 µg/mL and (S)-2-[4-(3-fluorobenzyloxy)benzylamino]propanamide methanesulfonate at about 1.00 µg/mL (about 0.10%).

Reference Solution for the (S)-2-[3-(3-fluorobenzyl)-4-(3-fluorobenzyloxy)benzylamino]propanamide methanesulfonate in the (S)-2-[4-(3-fluorobenzyloxy)benzylamino]propanamide methanesulfonate Accurately weigh about 24 mg of (S)-2-[3-(3-fluorobenzyl)-4-(3-fluorobenzyloxy)benzylamino]propanamide reference standard and 20 mg of (S)-2-[4-(3-fluorobenzyloxy) benzylamino]propanamide methanesulfonate reference standard in a 50 mL volumetric flask, dissolve and dilute to volume with diluent; dilute 1.0 mL of this solution to 20 mL with diluent ($1^{st}$ dilution); dilute 1.0 mL of the last solution to 20 mL with diluent ($2^{nd}$ dilution) to obtain a solution containing 2-[3-(3-fluorobenzyl)-4-(3-fluorobenzyloxy)benzylamino]propanamide (about 0.15% as methanesulfonic salt) at about 1.20 µg/mL and (S)-2-[4-(3-fluorobenzyloxy)benzylamino]propanamide methanesulfonate at about 1.00 µg/mL (about 0.10%).

Test Solution:

Accurately weigh about 25 mg of test product in a 25 mL volumetric flask, dissolve and dilute to volume with diluent to obtain a solution having known concentration of about 1.0 mg/mL.

Chromatographic Conditions:
The chromatographic procedure is carried out by using:
- Column: Waters Simmetry C8 150×4.6 mm, 5 μm size, or equivalent
- column temperature: 30° C.
- mobile phase: mixture of 40% solvent A: 10% solvent B: 50% solvent C, containing 1 g/L of sodium octanesulfonate
  - solvent A: buffer solution 0.05M $KH_2PO_4$;
  - solvent B: acetonitrile;
  - solvent C: methanol;
- isocratic elution;
- run time: 60 min;
- flow rate: 1.0 mL/min;
- detection: UV 220 nm;
- injection volume: 100 μL;
- diluent: mobile phase Procedure:

Inject blank (diluent), reference solution, test solution and record the chromatograms.

In the reference chromatogram verify the following system suitability parameters:
- (S)-2-[4-(2-Fluorobenzyloxy)benzylamino]propanamide retention time is about 5.2 min;
- The USP tailing for (S)-2-[4-(2-fluorobenzyloxy)benzylamino]propanamide peak is in the range between 0.8 and 1.5;
- (S)-2-[3-(2-Fluorobenzyl)-4-(2-fluorobenzyloxy)benzylamino]propanamide relative retention time is about 5.1.

or
- (S)-2-[4-(3-Fluorobenzyloxy)benzylamino]propanamide retention time is about 5.5 min;
- The USP tailing for (S)-2-[4-(3-fluorobenzyloxy)benzylamino]propanamide peak is in the range between 0.8 and 1.5;
- (S)-2-[3-(3-Fluorobenzyl)-4-(3-fluorobenzyloxy)benzylamino]propanamide relative retention time is about 4.1.

Adjust the mobile phase in order to obtain the system suitability.

Calculate the Percent Content

S) [3-(2-fluorobenzyl)-4-(2-fluorobenzyloxy)benzylamino]propanamide (free base and methanesulfonate) in the examined (S)-2-[4-(2-fluorobenzyloxy)benzylamino]propanamide (free base and methanesulfonate) samples and of (S)-2-[3-(3-fluorobenzyl)-4-(3-fluorobenzyloxy)benzylamino]propanamide (free base and methanesulfonate) in the examined (S)-2-[4-(3-fluorobenzyloxy)benzylamino]propanamide (free base and methanesulfonate) samples by external standard calculation.

The value of the limit of quantization (LOQ) for (S)-2-[3-(2-fluorobenzyl)-4-(2-fluorobenzyloxy)benzylamino]propanamide and for (S)-2-[3-(3-fluorobenzyl)-4-(3-fluorobenzyloxy)benzylamino]propanamide in the corresponding (S)-2-[4-(2-fluorobenzyloxy)benzylamino]propanamide and (S)-2-[4-(3-fluorobenzyloxy)benzylamino]propanamide is 0.004% by weight. The value of the limit of quantization (LOQ) for (S)-2-[3-(2-fluorobenzyl)-4-(2-fluorobenzyloxy)benzylamino]propanamide methanesulfonate and for (S)-2-[3-(3-fluorobenzyl)-4-(3-fluorobenzyloxy)benzylamino]propanamide methanesulfonate in the corresponding (S)-2-[4-(2-fluorobenzyloxy)benzylamino]propanamide methanesulfonate and (S)-2-[4-(3-fluorobenzyloxy)benzylamino]propanamide methanesulfonate is 0.005% by weight. The value of the limit of detection for all the considered impurities is 0.001% by weight.

The same procedure and reference values are used for the determination of the C,O-dibenzylated impurities (IIa), (II'b), (II'c), (II'd) and the respective racemic mixtures, in the R-enantiomers (I'a), (I'b), (I'c), (I'd) and the respective racemic mixtures.

EXAMPLE 26A

HPLC Enantiomeric Purity Determination of (S)-2-[4-(2-fluorobenzyloxy)benzylamino]propanamide (Ib) and its methanesulfonate (Id)

The enantiomeric purity of the sample is evaluated by HPLC. The determination is carried out according to the following:

Standard Solution 1:

Dissolve about 5.3 mg of (R)-2-[4-(2-fluorobenzyloxy)benzylamino]propanamide methanesulfonate reference standard in 25 mL of mobile phase.

Standard Solution 2:

Dissolve about 8.0 mg of (S)-2-[4-(2-fluorobenzyloxy)benzylamino]propanamide methanesulfonate reference standard and 0.2 mL of standard solution 1 in 50 mL of mobile phase.

The concentration of (R)-2-[4-(2-fluorobenzyloxy)benzylamino]propanamide methanesulfonate is about 0.5% calculated with respect to the concentration of (S)-2-[4-(2-fluorobenzyloxy)benzylamino]propanamide methanesulfonate.

Test Solutions 1 and 2:

In duplicate, dissolve about 8.0 mg of the test product in 50 mL of mobile phase.

Chromatographic Conditions:
- Column: Chiralpak WH 250 mm×4.6 mm, I.D. 5 μm;
- column temperature: 45° C.;
- mobile phase: 0.25 mM $CuSO_4$ (accurately weigh about 40 mg of $CuSO_4$ in 1000 mL of water)/MeOH 60/40;
- isocratic elution;
- flow rate: 1.0 mL/min;
- detection: UV 230 nm;
- injection volume: 10 μL;
- run time: 15 min.

Procedure:

Analyse blank (mobile phase) once, standard solution 2 twice, test solutions 1 and 2 once and verify that:
- for the standard injections, the reference standard determination percent (RSD %) for (R)-2-[4-(2-fluorobenzyloxy)benzylamino]propanamide methanesulfonate percent area is less than 2.0%;
- both for standard and sample solutions, for each injection the main peak percent area is included between the average value±0.1%.

Calculate the (R)-2-[4-(2-fluorobenzyloxy)benzylamino]propanamide methanesulfonate content (percent area) as mean of the two determination.

Retention Times:
- (S)-2-[4-(2-Fluorobenzyloxy)benzylamino]propanamide retention time is about 5.7 min.
- (R)-2-[4-(2-Fluorobenzyloxy)benzylamino]propanamide relative retention time is about 1.7.

This method is employed also for determining the S-isomer ratio of the corresponding racemic (R,S) compounds (Ib, I'b) and (Id, I'd).

EXAMPLE 26B

HPLC Enantiomeric Purity Determination of (R)-2-[4-(2-fluorobenzyloxy)benzylamino]propanamide (I'b) and its methanesulfonate (I'd)

The enantiomeric purity of the sample is evaluated by HPLC. The determination is carried out according to the following:

Standard Solution 1:

Dissolve about 5.3 mg of (S)-2-[4-(2-fluorobenzyloxy)benzylamino]propanamide methanesulfonate reference standard in 25 mL of mobile phase.

Standard Solution 2:

Dissolve about 8.0 mg of (R)-2-[4-(2-fluorobenzyloxy)benzylamino]propanamide methanesulfonate reference standard and 0.2 mL of standard solution 1 in 50 mL of mobile phase.

The concentration of (S)-2-[4-(2-fluorobenzyloxy)benzylamino]propanamide methanesulfonate is about 0.5% calculated with respect to the concentration of (R)-2-[4-(2-fluorobenzyloxy)benzylamino]propanamide methanesulfonate.

Test Solutions 1 and 2:

In duplicate, dissolve about 8.0 mg of the test product in 50 mL of mobile phase.

Chromatographic Conditions:
Column: Chiralpak WH 250 mm×4.6 mm, I.D. 5 µm;
column temperature: 45° C.;
mobile phase: 0.25 mM $CuSO_4$ (accurately weigh about 40 mg of $CuSO_4$ in 1000 mL of water)/MeOH 60/40;
isocratic elution;
flow rate: 1.0 mL/min;
detection: UV 230 nm;
injection volume: 10 µL;
run time: 15 min.

Procedure:

Analyse blank (mobile phase) once, standard solution 2 twice, test solutions 1 and 2 once and verify that:
for the standard injections, the RSD % for (S)-2-[4-(2-fluorobenzyloxy)benzylamino]propanamide methanesulfonate percent area is less than 2.0%;
both for standard and sample solutions, for each injection the main peak percent area is included between the average value±0.1%.

Calculate the (S)-2-[4-(2-fluorobenzyloxy)benzylamino]propanamide methanesulfonate content. (percent area) as mean of the two determination.

Retention Times:

(R)-2-[4-(2-Fluorobenzyloxy)benzylamino]propanamide retention time is about 9.69 min.

(S)-2-[4-(2-Fluorobenzyloxy)benzylamino]propanamide relative retention time is about 0.58.

This method is employed also for determining the R isomer ratio of the corresponding racemic (R,S) compounds (Ib, I'b) and (Id, I'd)

EXAMPLE 27A

HPLC enantiomeric purity determination of (S)-2-[4-(3-fluorobenzyloxy)benzylamino]propanamide (Ia) its methanesulfonate (Ic)

The enantiomeric purity of the sample is evaluated by HPLC. The determination takes place according to the following conditions:

Test Solution:

Dissolve about 10 mg of test sample in 10 mL of mobile phase.

Chromatographic Conditions:
Column: Chiralpak WH 250 mm×4.6 mm, I.D. 10 µm;
column temperature: 50° C.;
mobile phase: 0.25 mM $CuSO_4$
isocratic elution;
flow rate: 1.0 mL/min;
detection: UV 200 nm;
injection volume: 10
run time: 30 min.

Procedure:

Inject the test solution and calculate the enantiomers peak response as area percent.

(S)-2-[4-(3-Fluorobenzyloxy)benzylamino]propanamide retention time is about 9.2 min.

(R)-2-[4-(3-Fluorobenzyloxy)benzylamino]propanamide relative retention time is about 1.9.

This method is employed also for determining the S-isomer ratio of the corresponding racemic (R,S) compounds (Ia, I'a) and (Ic, I'c)

EXAMPLE 27B

HPLC enantiomeric purity determination of (R)-2-[4-(3-fluorobenzyloxy)benzylamino]propanamide (I'a) and its methanesulfonate (I'c)

The enantiomeric purity of the sample is evaluated by HPLC. The determination takes place according to the following conditions:

Test Solution:

Dissolve about 10 mg of test sample in 10 mL of mobile phase.

Chromatographic Conditions:
Column: Chiralpak WH 250 mm×4.6 mm, I.D. 10 µm;
column temperature: 50° C.;
mobile phase: 0.25 mM $CuSO_4$
isocratic elution;
flow rate: 1.0 mL/min;
detection: UV 200 nm;
injection volume: 10 µL;
run time: 30 min.

Procedure:

Inject the test solution and calculate the enantiomers peak response as area percent.

(R)-2-[4-(3-Fluorobenzyloxy)benzylamino]propanamide retention time is about 17.48 min.

(S)-2-[4-(3-Fluorobenzyloxy)benzylamino]propanamide relative retention time is about 0.56.

This method is employed also for determining the R isomer ratio of the corresponding racemic (R,S) compounds (Ia, I'a) and (Ic, I'c)

EXAMPLE 27C

HPLC Enantiomeric Purity Determination of (S) and (R)-2-[3-(2-fluorobenzyl)-4-(2-fluorobenzyloxy)benzylamino]propanamide (free base IIb, and methanesulfonate IId)

Test Solution

In a 20 mL volumetric flask accurately weight about 20.0 mg of the substances to be examined, dissolve and dilute to volume with the mobile phase.

Chromatographc Conditions

The chromatographic procedure is carried out using:
Column:
CHIRALPAK AD-H 25 cm×4.6 mm
Mobile phase:
80% solvent A: n-hexane
20% solvent B: n-ethanol
0.3% Diethylamine (DEA)
Flow rate:
0.8 mL/min Detection:
UV at 240 nm
Injection volume:
10 µL
Run time:
20 min
Procedure
Inject the sample solution and record the chromatogarms.
Calculate the percentage of enantiomers as Area %
Enantiomer S: RT=7.298
Enantiomer R: RT=7.617
RT ratio=1.04

This method is employed also for determining the S/R isomer ratio of the corresponding racemic compounds (IIb, II'b) and (IId, II'd).

EXAMPLE 27D

HPLC Enantiomeric Purity Determination of (S) and (R)-2-[3-(3-fluorobenzyl)-4-(3-fluorobenzyloxy) benzylamino]propanamide (free base IIa, and methanesulfonate IIc)

Test Solution
In a 20 mL volumetric flask accurately weight about 20.0 mg of the substances to be examined, dissolve and dilute to volume with the mobile phase.
Chromatographc Conditions
The chromatographic procedure is carried out using:
Column:
CHIRALPAK AD-H 25 cm×4.6 mm
Mobile phase:
80% solvent A: n-hexane
20% solvent B: n-ethanol
0.3% Diethylamine (DEA)
Flow rate:
0.8 mL/min
Detection:
UV at 240 nm
Injection volume:
10 µL
Run time:
20 min
Procedure
Inject the sample solution and record the chromatogarms.
Calculate the percentage of enantiomers as Area %
Enantiomer S: RT=8.211
Enantiomer R: RT=8.714
RT ratio=1.061

This method is employed also for determining the R/S isomer ratio of the corresponding racemic compounds (IIa, II'a) and (IIc, II'e)

EXAMPLE 28

Cytochrome P450 Assay
Inhibition of the five most important Cytochrome P450 isoforms (CYP1A2, CYP2C9, CYP2C19, CYP2D6 and CYP3A4), involved in drug metabolism, was measured using specific substrates that become fluorescent upon CYP metabolism (Gentest Kit assay).

Compounds were tested in a 96-well plate containing incubation/NADPH regenerating buffer. Specific human recombinant isoenzymes and substrates were added and incubated at 37° C. for 15 min for CYP1A2/CEC, 40 min for CYP2E1/MFC, 45 min for CYP2C9/MFC and 30 min for the others CYP450.

The specific substrates were the following: 3-cyano-7-ethoxycoumarin (CYP2C19 and CYP1A2),
7-methoxy-4-trifluoromethylcoumarin (CYP2C9),
3 [2 (N,N-diethyl-N-methylamino) ethyl]-7-methoxy-4-methylcoumarin (CYP2D6)
benzylphenylcoumarin (CYP3A4)

The plates were read on a Victor plate reader (Perkin Elmer) at the appropriate emission/excitation wavelengths, and the $IC_{50}$ (concentration inhibiting by 50% the enzyme activity) determined. The results are reported in Tables 1 and 2.

EXAMPLE 29

Cytotoxicity Assay in Human Neuroblastoma Cell Line SH-SY-5Y

At time zero, the cells were seeded at $1.10^4/cm^2$ in 96 well plates in DMEM growth medium+10% heat inactivated FBS+2 mM l-Glutamine+100 U/mL-100 µg/mL Penicillin/Streptomycin.

After 72 hours at subconfluent phase of growth, the medium was removed and cells were incubated for 24 hours at 37° C. in 180 µL of neurobasal medium+2 mM 1-Glutamine (Life Techonologies) with or without test compounds (20 µL, at least 5 concentrations in triplicate).

At the end of incubation, 20 µL of Alamar Blue dye (AlamarBlue™ Assay Kit, Promega) were directly added to the cell medium.

Four hours after, the cytotoxicity was assessed by measuring the fluorescence at 530 nm excitation and 595 nm emission using Tecan Spectrafluor plate reader.

Before and at the end of the treatment, the cultures were monitored microscopically by an Olympus IX70 inverted light microscope matched to an Image Analyzer (Image Pro Plus, 5.1) to evaluate the cellular morphology.

Results are epressed in Table 1 as concentration inducing 50% of mortality.

EXAMPLE 30

HERG Current in Transfected CHO Cell Lines
The inhibition of HERG current was tested in CHO cells stably expressing recombinant HERG channel.

To evaluate the effect of the test compounds on HERG currents, cells were clamped at −80 mV, depolarised to 0 mV for 5 seconds allowing activation of HERG current and repolarised to −50 mV during 5 seconds allowing HERG tail current to deactivate. This procedure was repeated at a frequency of 0.06 Hz. The current amplitude upon repolarisation (HERG tail current) was measured before and after exposure to the test compound.

Inhibition of current was calculated as the difference between the amplitude of HERG tail current amplitude measured at the end of external bath perfusion period and HERG tail current measured at the end of test compound perfusion period (when steady-state effect is reached) divided by control HERG tail current.

Drug concentration-inhibition curves were obtained by plotting tonic blocks versus drug concentrations. Dose-response curves were fitted to the tonic block data, according to the logistic equation: $y=A2+(A1-A2)/[1+(x/IC_{50})P]$. A1 and A2 are fixed values of 0 and 1 corresponding to 0 and 100% current inhibition, x is the drug concentration, $IC_{50}$ is the drug concentration resulting in 50% current inhibition and p is the corresponding slope factor. The results are reported in Table 1.

EXAMPLE 31

Maximal Electroshock Test (MES) in Mice

The maximal electroshock test (MES) is used commonly in the screening of anti-epileptic drugs in rodent models.

Animals and Apparatus: Male CD1 mice weighing 25 g were used. The procedure described by White et al. (White H. S., Woodhead J. H., Franklin M. R., Swinyard E. A., and Wolf H. H. Antiepileptic Drugs (1995) $4^{th}$ ed.: 99-110, Raven Press, Ltd., New York) was followed. An Ugo Basile electroconvulsive generator (Model ECT UNIT 7801) was used to deliver an electrical stimulus sufficient to produce a hindlimb tonic extensor response in at least 97% of control animals. The stimulus was delivered intra-aurally through clip electrodes in mice (0.7 seconds of a 40 mA shock, with a pulse train of 80 Hz having a pulse duration of 0.4 ms). The acute effect of compounds administered intraperitoneally or orally 15-60 min before MES induction were examined and compared with a vehicle control group. Ten mice were studied per group. Complete suppression of the hindlimb tonic extensor component of seizures was taken as evidence of anticonvulsant activity.

The compounds of the invention were administered orally or intraperitoneally at the doses of 3-30 mg/kg.

The results are expressed in Tables 3 and 4 as % of protection.

The invention claimed is:

1. A method for treating central nervous system (CNS) disorders selected from the group consisting of epilepsy, Parkinson's disease, Alzheimer's disease, depression, restless legs syndrome, pain and migraine which comprises the step of administering to a patient in need thereof an effective amount of (S)-2-[4-(3-fluorobenzyloxy)benzylamino]propanamide, (Ia)

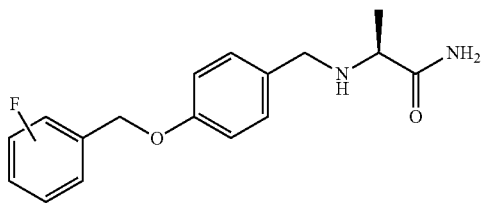

safinamide (Ia): 3-F its R-enantiomer (I'a), their racemic mixture (Ia, I'a) or a pharmaceutically acceptable salt thereof, and, optionally, one or more additional active agents, wherein safinamide (Ia), its R-enantiomer (I'a), their racemic mixture (Ia, I'a) or a pharmaceutically acceptable salt thereof has a content of the impurity (S)-2-[3-(3-fluorobenzyl)-4-(3-fluorobenzyloxy)-benzylamino]propanamide (IIa),

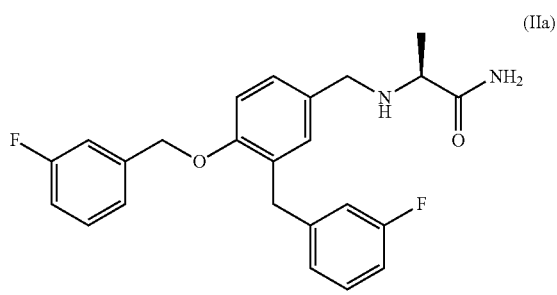 [SMILES: C[C@H](NCc1ccc(OCc2cccc(F)c2)c(Cc2cccc(F)c2)c1)C(N)=O]

its R-enantiomer (II'a), their racemic mixture (IIa, II'a), or a salt thereof with a pharmaceutically acceptable acid which is lower than 0.03% (by weight) and is obtained by a process characterized in that a Schiff base intermediate of formula (IIIa)

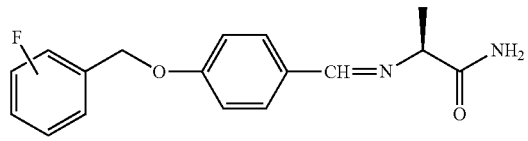

(IIIa): 3-F its R-enantiomer or their racemic mixture (IIIa, III'a), (i) is obtained by an iminoalkylation reaction of 4-(3-fluorobenzyloxy)benzaldehyde with L-alaninamide or D-alaninamide or the racemic mixture thereof, without any addition of molecular sieves, in a solvent selected from ($C_1$-$C_5$) lower alkanols at a temperature between 20° and 30° C. in an amount of such solvent with respect to the aldehyde which allows formation of a suspension of the Schiff base in a saturated solution of the Schiff base in the same solvent, and (ii) after completion of the iminoalkylation reaction, is submitted to a reduction reaction with a reducing agent selected from sodium borohydride and potassium borohydride in an organic solvent selected from one or more ($C_1$-$C_5$) lower alkanols, optionally with water, wherein the ratio of the organic solvent to the Schiff base allows the formation and the presence during a substantial portion of the reduction reaction course of a suspension of the Schiff base into the saturated solution of the Schiff base in the same organic solvent and ranges from 0.5 L to 3.0 L per each mole of Schiff base, (iii) the process being further characterized in that the 4-(3-fluorobenzyloxy)benzaldehyde starting material employed for the preparation of the Schiff base intermediate (IIIa), (III'a), or their racemic mixture (IIIa, III'a) has a content of 3-(3-fluorobenzyl)-4-(3-fluorobenzyloxy)benzaldehyde impurity lower than 0.03% (by weight);

whereby safinamide (Ia), its R-enantiomer (I'a) or their racemic mixture (Ia, I'a) is obtained in a free base form and, optionally, said free base form is converted in a salt thereof with a pharmaceutically acceptable acid.

2. The method according to claim 1, wherein safinamide (Ia), its R-enantiomer (I'a), their racemic mixture (Ia, I'a) or a pharmaceutically acceptable salt thereof has a content of the impurity (S)-2-[3-(3-fluorobenzyl)-4-(3-fluorobenzyloxy)-benzylamino]propanamide (IIa), its R-enantiomer (II'a), their racemic mixture (IIa, II'a) or a salt thereof with a pharmaceutically acceptable acid which is lower than 0.01% (by weight).

3. The method according to claim 1, wherein the CNS disorder is Parkinson's disease and an additional active agent is administered selected from a dopamine agonist, levodopa, catechol-O-methyltransferase (COMT) inhibitor, or a combination thereof.

4. The method according to claim 1, wherein said patient is classified as a poor drug metabolizer (PM) or is concomitantly assimilating other drugs that interfere with CYP 450 cytochromes.

5. The method according to claim 1, wherein the compound which is administrated is safinamide or a pharmaceutically acceptable salt thereof.

6. The method according to claim 5, wherein the pharmaceutically acceptable salt is the salt with methanesulfonic acid.

7. A method for treating a disease where sodium and/or calcium channel mechanism(s) play(s) a pathological role, selected from the group consisting of pain, migraine, bipolar disorders, depression, inflammatory processes, disorders affecting skin and related tissues, disorders of the respiratory system, disorders of the immune and endocrinological system, cardiovascular, metabolic, gastrointestinal, and urogenital disorders, which comprises the step of administering to a patient in need thereof an effective amount of ralfinamide ((S)-2-[4-(2-fluorobenzyloxy)benzylamino]propanamide Ib)

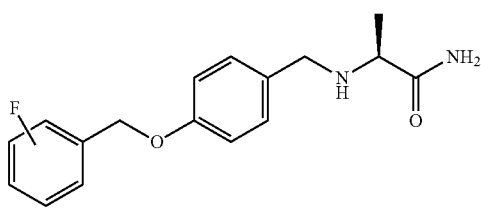

ralfinamide (Ib): 2-F its R-enantiomer (I'b), their racemic mixtures (Ib, I'b) or a pharmaceutically acceptable salt thereof and, optionally, one or more additional active agents wherein ralfinamide (Ib), its R-enantiomer (I'b), their racemic mixture (Ib, I'b) or a pharmaceutically acceptable salt thereof has a content of the impurity (S)-2-[3-(2-fluorobenzyl)-4-(2-fluorobenzyloxy)-benzylamino]propanamide (IIb),

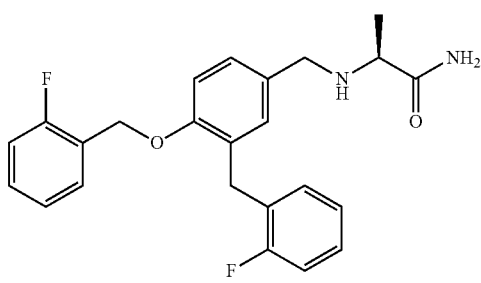

ralfinamide (Ib): 2-F its R-enantiomer (II'b), their racemic mixture (IIb, II'b), or a salt thereof with a pharmaceutically acceptable acid which is lower than 0.03% (by weight) and is obtained by a process characterized in that a Schiff base intermediate of formula (IIIb)

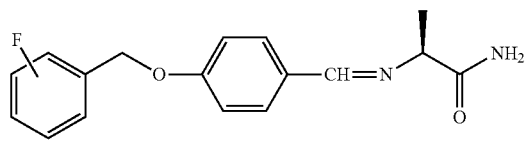

(IIIb): 2-F its R-enantiomer arm* or their racemic mixture (IIIb, III'b), (i) is obtained by an iminoalkylation reaction of 4-(2-fluorobenzyloxy)benzaldehyde with L-alaninamide or D-alaninamide or the racemic mixture thereof, without any addition of molecular sieves, in a solvent selected from ($C_1$-$C_5$) lower alkanols at a temperature between 20° and 30° C. in an amount of such solvent with respect to the aldehyde which allows formation of a suspension of the Schiff base in a saturated solution of the Schiff base in the same solvent, and (ii) after completion of the iminoalkylation reaction, is submitted to a reduction reaction with a reducing agent selected from sodium borohydride and potassium borohydride in an organic solvent selected from one or more ($C_1$-$C_5$) lower alkanols, optionally with water, wherein the ratio of the organic solvent to the Schiff base allows the formation and the presence during a substantial portion of the reduction reaction course of a suspension of the Schiff base into the saturated solution of the Schiff base in the same organic solvent and ranges from 0.5 L to 3.0 L per each mole of Schiff base, (iii) the process being further characterized in that the 4-(2-fluorobenzyloxy)benzaldehyde starting material employed for the preparation of the Schiff base intermediate (IIIb), (III'b), or their racemic mixture (IIIb, III'b) has a content of 3-(2-fluorobenzyl)-4-(2-fluorobenzyloxy)benzaldehyde impurity lower than 0.03% (by weight);

whereby ralfinamide (Ib), its R-enantiomer (I'b) or their racemic mixture (Ib, I'b) is obtained in a free base form and, optionally, said free base form is converted in a salt thereof with a pharmaceutically acceptable acid.

8. The method according to claim 7, wherein ralfinamide (Ib), its R-enantiomer (I'b), their racemic mixture (Ib, I'b) or a pharmaceutically acceptable salt thereof has a content of the impurity (S)-2-[3-(2-fluorobenzyl)-4-(2-fluorobenzyloxy)-benzylamino]propanamide (IIb), its R-enantiomer (II'b), their racemic mixture (IIb, II'b) or a salt thereof with a pharmaceutically acid which is lower than 0.01% (by weight).

9. The method according to claim 7, wherein the disease is pain or migraine.

10. The method according to claim 9, wherein said pain is chronic pain or neuropathic pain.

11. The method according to claim 7, wherein the disease is pain and an additional active agent is administered selected from gabapentin and pregabalin.

12. The method according to claim 7, wherein the compound which is administered is ralfinamide or a pharmaceutically acceptable salt thereof and wherein said patient is classified as a poor drug metabolizer (PM) or is concomitantly assimilating other drugs that interfere with CYP 450 cytochromes.

13. The method according to claim 7, wherein the compound is the R-enantiomer of ralfinamide or a pharmaceutically acceptable salt thereof and wherein said patient is classified as a poor drug metabolizer (PM) or is concomitantly assimilating other drugs that interfere with CYP 450 cytochromes, wherein said compound exhibits significantly reduced MAO inhibitory effects.

14. The method according to claim 7, wherein the pharmaceutically acceptable salt is the salt with methanesulfonic acid.

15. A method for treating central nervous (CNS) disorders selected from the group consisting of epilepsy, Parkinson's disease, Alzheimer's disease, depression, restless legs syndrome, pain and migraine, which comprises the step of administering to a patient in need thereof an effective amount of the R-enantiomer of safinamide, ((R)-2[4-(3-fluorobenzyloxy)benzylamino]propanamide, I'a) or a pharmaceutically acceptable salt thereof and, optionally, one or more additional active agents, wherein the R-enantiomer of safinamide (I'a) or a salt thereof with a pharmaceutically acceptable acid has a content of the impurity (R)-2-[3-(3-fluorobenzyl)-4-(3-fluorobenzyloxy)-benzylamino]propanamide (II'a) or a salt thereof with a pharmaceutically acceptable acid which is lower than 0.03% (by weight).

16. The method according to claim 15, wherein the R-enantiomer of safinamide (I'a) or a salt thereof with a pharmaceutically acceptable acid has a content of the impurity (R)-2-[3-(3-fluorobenzyl)-4-(3-fluorobenzyloxy)-benzylamino]propanamide (II'a) or a salt thereof with a pharmaceutically acceptable acid which is lower than 0.01% by weight.

17. The method according to claim 15, wherein the CNS disorders is Parkinson's disease and an additional active agent is administered selected from a dopamine agonist, levodopa, catechol-O-methyltransferase (COMT) inhibitor, and a combination thereof.

18. The method according to claim 15, wherein said patient is classified as a poor drug metabolizer (PM) or is concomitantly assimilating other drugs that interfere with CYP 450 cytochromes.

19. The method according to claim 15, wherein the pharmaceutically acceptable salt is a salt with methanesulfonic acid.

20. The method according to claim 17, wherein the pharmaceutically acceptable salt is the salt with methanesulfonic acid.

21. A method for treating a disease where sodium and/or calcium channel mechanism(s) play(s) a pathological role, selected from the group consisting of pain, migraine, bipolar disorders, depressions, inflammatory processes, disorders affecting skin and related tissues, disorders of the respiratory system, disorders of the immune and endocrinological system, cardiovascular, metabolic, gastrointestinal, and urogenital disorders, which comprises the step of administering to a patient in need thereof an effective amount of the R-enantiomer of ralfinamide ((R)-2-[4-(2-fluorobenzyloxy)benzylamino]propanamide, I'b) or a pharmaceutically acceptable salt thereof and, optionally, one or more additional active agents, wherein the R-enantiomer of ralfinamide (I'b) has a content of the impurity (R)-2-[3-(2-fluorobenzyl)-4-(2-fluorobenzyloxy)-benzylamino]propanamide (II'b) or a salt thereof with a pharmaceutically acceptable acid which is lower than 0.03% (by weight).

22. The method according to claim 21, wherein the R-enantiomer of ralfinamide (I'b) or a pharmaceutically acceptable salt thereof has a content of the impurity (R)-2-[3-(2-fluorobenzyl)-4-(2-fluorobenzyloxy)-benzylamino]propanamide (II'b) or a salt thereof with a pharmaceutically acceptable acid which is lower than 0.01% (by weight).

23. The method according to claim 21, wherein the disease is pain or migraine.

24. The method according to claim 23, wherein said pain is chronic pain or neuropathic pain.

25. The method according to claim 21, wherein the disease is pain and the additional active agent is selected from gabapentin and pregabalin.

26. The method according to claim 21, wherein said patient is classified as a poor drug metabolizer (PM) or is concomitantly assimilating other drugs that interfere with CYP 450 cytochromes.

27. The method according to claim 21, wherein said patient is classified as a poor drug metabolizer (PM) or is concomitantly assimilating other drugs that interfere with CYP 450 cytochromes, wherein said compound exhibits significantly reduced MAO inhibitory effects.

28. The method according to claim 21, wherein the pharmaceutically acceptable salt is the salt with methanesulfonic acid.

29. The method according to claim 23, wherein the pharmaceutically acceptable salt is a salt with methanesulfonic acid.

30. The method according to claim 25, wherein the pharmaceutically acceptable salt is the salt with methanesulfonic acid.

31. A method for treating pain which comprises the step of administering to a patient in need thereof an effective amount of safinamide ((S)-2-[4-(3-fluorobenzyloxy)benzylamino]propanamide, Ia)

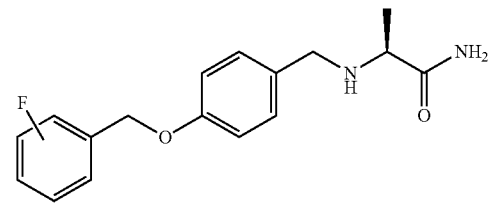

safinamide (Ia): 3-F or a pharmaceutically acceptable salt thereof and, optionally, one or more additional active agents, wherein safinamide (Ia) or a pharmaceutically acceptable salt thereof has a content of the impurity (S)-2-[3-(3-fluorobenzyl)-4-(3-fluorobenzyloxy)benzylamino]propanamide (IIa) or a salt thereof with a pharmaceutically acceptable acid which is lower than 0.03% (by weight).

32. The method according to claim 31, wherein safinamide (Ia) or a pharmaceutically acceptable salt thereof has a content of the impurity (S)-2-[3-(3-fluorobenzyl)-4-(3-fluorobenzyloxy)benzylamino]propanamide (IIa) which is lower than 0.01% (by weight).

33. The method according to claim 31, wherein said pain is chronic pain or neuropathic pain.

34. The method according to claim 31, wherein an additional active agent is administered selected from gabapentin and pregabalin.

35. The method according to claim 31, wherein said patient is classified as a poor drug metabolizer (PM) or is concomitantly assimilating other drugs that interfere with CYP 450 cytochromes.

36. The method according to claim 31, wherein the pharmaceutically acceptable salt is the salt with methanesulfonic acid.

37. The method according to claim 33, wherein the pharmaceutically acceptable salt is the salt with methanesulfonic acid.

38. The method according to claim 34, wherein the pharmaceutically acceptable salt is the salt with methanesulfonic acid.

39. A process for preparing a compound of Formula (I):

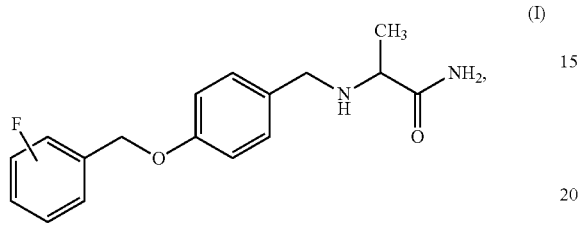

or a salt thereof, obtained by the process comprising the steps of:
(a) treating a compound of formula (III):

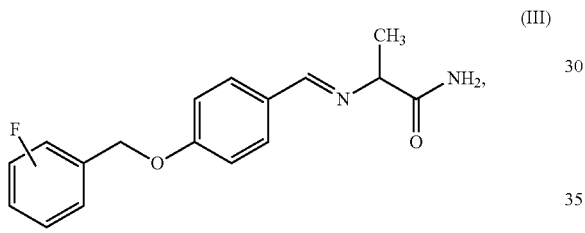

or a salt thereof, with a hydride reducing agent under reducing conditions, wherein the reducing conditions comprise contacting a starting amount of a compound of Formula (III) with a hydride reducing agent and an organic solvent forming a reaction mixture, wherein the volume of organic solvent is from 0.5 to 3.0 liters per mole of the starting amount of the compound of Formula (III);
(b) optionally monitoring the reaction mixture to determine progress of reduction reaction;
(c) isolating the compound of Formula (I) or a salt thereof upon completion or substantial completion of the reduction of compound (III) to compound (I); and
(d) optionally forming a salt of the compound of Formula (I).

40. A process for preparing a compound of Formula (I):

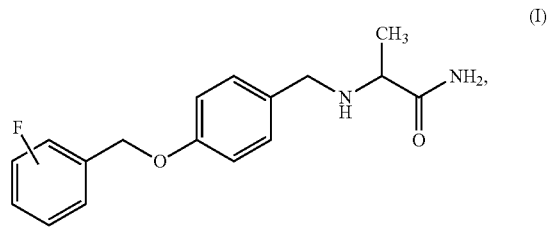

or a salt thereof, obtained by the process comprising the steps of:
(a) treating an aldehyde of formula (IV):

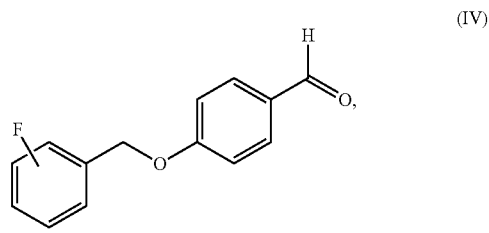

with alaninamide under iminoalkylation conditions, wherein the iminoalkylation conditions comprise contacting a starting amount of an aldehyde of Formula (IV) with alaninamide and an organic solvent to form the iminoalkylation reaction mixture, wherein the volume of organic solvent is from 0.5 to 3.0 liters per mole of the starting amount of the aldehyde of Formula (IV);
(b) allowing the iminoalkylation reaction to go to completion or substantially to completion;
(c) treating the iminoalkylation reaction mixture with a hydride reducing agent under reducing conditions, wherein the reducing conditions comprise contacting the iminoalkylation reaction mixture with a hydride reducing agent and maintaining the volume of organic solvent from 0.5 to 3.0 liters per mole of the starting amount of the aldehdye of Formula (IV);
(d) optionally monitoring the reaction mixture to determine progress;
(e) isolating the compound of Formula (I) or a salt thereof upon completion or substantial completion of the reduction to compound (I); and
(f) optionally forming a salt of the compound of Formula (I).

* * * * *